US011325968B2

(12) United States Patent
Kallunki et al.

(10) Patent No.: US 11,325,968 B2
(45) Date of Patent: May 10, 2022

(54) ALPHA-SYNUCLEIN ANTIBODIES

(71) Applicant: H. Lundbeck A/S, Valby (DK)

(72) Inventors: Pekka Kallunki, Valby (DK); Karina Fog, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/469,482

(22) PCT Filed: Dec. 14, 2017

(86) PCT No.: PCT/EP2017/082749

§ 371 (c)(1),
(2) Date: Jun. 13, 2019

(87) PCT Pub. No.: WO2018/109058

PCT Pub. Date: Jun. 21, 2018

(65) Prior Publication Data

US 2020/0024337 A1 Jan. 23, 2020

(30) Foreign Application Priority Data

Dec. 16, 2016 (DK) ............................. PA201600769

(51) Int. Cl.
*C07K 16/18* (2006.01)
*A61P 25/16* (2006.01)

(52) U.S. Cl.
CPC .............. *C07K 16/18* (2013.01); *A61P 25/16* (2018.01); *C07K 2317/24* (2013.01); *C07K 2317/34* (2013.01); *C07K 2317/56* (2013.01); *C07K 2317/565* (2013.01); *C07K 2317/567* (2013.01); *C07K 2317/92* (2013.01)

(58) Field of Classification Search
CPC ............................ C07K 16/18; A61K 39/3955
See application file for complete search history.

(56) References Cited

U.S. PATENT DOCUMENTS 4,179,337 A 12/1979 Davis et al.
4,495,285 A 1/1985 Shimizu et al.
4,609,546 A 9/1986 Hiratani
4,766,106 A 8/1988 Katre et al.
4,946,778 A 8/1990 Ladner et al.
5,225,539 A 7/1993 Winter
5,530,101 A 6/1996 Queen et al.
5,545,806 A 8/1996 Lonberg et al.
5,545,807 A 8/1996 Surani et al.
5,569,825 A 10/1996 Lonberg et al.
5,585,089 A 12/1996 Queen et al.
5,625,126 A 4/1997 Lonberg et al.
5,633,425 A 5/1997 Lonberg et al.
5,661,016 A 8/1997 Lonberg et al.
5,741,957 A 4/1998 Doboer et al.
5,750,172 A 5/1998 Meade et al.
5,756,687 A 5/1998 Denman et al.
5,770,429 A 6/1998 Lonberg et al.
5,789,650 A 8/1998 Lonberg et al.
5,814,318 A 9/1998 Lonberg et al.
5,827,690 A 10/1998 Meade et al.
5,859,205 A 1/1999 Adair et al.
5,874,299 A 2/1999 Lonberg et al.
5,877,397 A 3/1999 Lonberg et al.
6,407,213 B1 6/2002 Carter et al.
6,881,557 B2 4/2005 Foote
8,632,776 B2 1/2014 Nordström et al.
10,358,482 B2 7/2019 Kallunki et al.
10,358,483 B2 7/2019 Kallunki et al.
10,358,484 B2 7/2019 Kallunki et al.
10,364,285 B2 7/2019 Kallunki et al.
10,364,286 B2 7/2019 Fog et al.
10,800,836 B2 10/2020 Kallunki et al.
10,889,635 B2 1/2021 Kallunki et al.
2002/0197258 A1 12/2002 Ghanbari et al.
2006/0045037 A1 3/2006 Nomura
2006/0205024 A1 9/2006 Rogers et al.
2008/0175838 A1 7/2008 Schenk et al.
2009/0208487 A1 8/2009 Schenk et al.
2012/0308572 A1 12/2012 Nordström et al.
2013/0063516 A1 3/2013 Sakai et al.
2013/0072663 A1 3/2013 Chilcote et al.
2013/0317199 A1 11/2013 Chilcote et al.
2014/0127131 A1 5/2014 Barbour et al.
2014/0186294 A1 7/2014 Gardai et al.
2015/0183855 A1 7/2015 Diamond et al.
2017/0015739 A1 1/2017 Kallunki et al.
2017/0192017 A1 7/2017 Barbour et al.
2018/0127491 A1 5/2018 Kallunki et al.

(Continued)

FOREIGN PATENT DOCUMENTS

CL 2011000739 A1 9/2011
EP 0 071 991 B1 5/1986

(Continued)

OTHER PUBLICATIONS

U.S. Appl. No. 15/207,859, filed Jul. 12, 2016, Published, U.S. Pat. No. 2017-00157391.
U.S. Appl. No. 15/812,251, filed Nov. 14, 2017, Granted, U.S. Pat. No. 10,358,482.
U.S. Appl. No. 15/812,303, filed Nov. 14, 2017, Granted, U.S. Pat. No. 10,358,483.
U.S. Appl. No. 15/812,363, filed Nov. 14, 2017, Granted, U.S. Pat. No. 10,364,285.
U.S. Appl. No. 15/812,410, filed Nov. 14, 2017, Granted, U.S. Pat. No. 10,358,484.
U.S. Appl. No. 15/812,648, filed Nov. 14, 2017, Allowed, U.S. Pat. No. 2018-0194833.
U.S. Appl. No. 15/848,999, filed Dec. 20, 2017, Granted, U.S. Pat. No. 10,364,286.

(Continued)

*Primary Examiner* — Robert C Hayes
(74) *Attorney, Agent, or Firm* — Wolf, Greenfield & Sacks, P.C.

(57) ABSTRACT

The present invention relates to a mouse antibody denoted m2E6, chimeric ch2E6, as well as to 3 humanized forms (2E6-HLD1, 2E6-HLD2 and 2E6-HLD3) and affinity matured forms of HLD1: 7A10, 5A1, 9D7, 9G11, 7C4, L3, 8D9, 9C12 or 6B6 to create higher affinity antibodies.

9 Claims, 27 Drawing Sheets

Specification includes a Sequence Listing.

(56) References Cited

U.S. PATENT DOCUMENTS

| | | | |
|---|---|---|---|
| 2018/0127492 A1 | 5/2018 | Kallunki et al. | |
| 2018/0179270 A1 | 6/2018 | Kallunki et al. | |
| 2018/0179271 A1 | 6/2018 | Kallunki et al. | |
| 2018/0179273 A1 | 6/2018 | Fog et al. | |
| 2018/0194833 A1 | 7/2018 | Kallunki et al. | |
| 2019/0367594 A1 | 12/2019 | Kallunki et al. | |
| 2019/0367595 A1 | 12/2019 | Kallunki et al. | |
| 2019/0382473 A1 | 12/2019 | Kallunki et al. | |
| 2020/0309796 A1 | 10/2020 | Malik et al. | |

FOREIGN PATENT DOCUMENTS

| | | |
|---|---|---|
| EP | 0180492 B2 | 5/1986 |
| EP | 0 314 406 B1 | 5/1989 |
| EP | 0 321 353 A1 | 6/1989 |
| EP | 3067066 A1 | 9/2016 |
| GB | 1 512 203 A | 5/1974 |
| JP | 2008-517928 A | 5/2008 |
| KR | 2012-0090672 A | 8/2012 |
| WO | WO 88/04777 A1 | 6/1988 |
| WO | WO 92/03918 A1 | 3/1992 |
| WO | WO 92/22645 A1 | 12/1992 |
| WO | WO 93/1227 A1 | 1/1993 |
| WO | WO 94/25585 A1 | 11/1994 |
| WO | WO 98/24884 A1 | 6/1998 |
| WO | WO 01/09187 A2 | 2/2001 |
| WO | WO 01/14424 A2 | 3/2001 |
| WO | WO 2002/004482 | 1/2002 |
| WO | WO 02/43478 A2 | 6/2002 |
| WO | WO 2004/041067 | 5/2004 |
| WO | WO 2005/013889 | 2/2005 |
| WO | WO 2006/020581 | 2/2006 |
| WO | WO 2006/045037 | 4/2006 |
| WO | WO 2007/011907 | 1/2007 |
| WO | WO 2007/012061 A2 | 1/2007 |
| WO | WO 2007/059782 A1 | 5/2007 |
| WO | WO 2008/103472 | 8/2008 |
| WO | WO 09/097006 A2 | 8/2009 |
| WO | WO 2009/133521 | 11/2009 |
| WO | WO 2010/039308 A1 | 4/2010 |
| WO | WO 2011/104696 | 9/2011 |
| WO | WO 2011/107544 | 9/2011 |
| WO | WO 2011/147890 A1 | 12/2011 |
| WO | WO 2012/177972 | 12/2012 |
| WO | WO 2013/063516 | 5/2013 |
| WO | WO 2014/132210 A1 | 9/2014 |
| WO | WO 2015/001504 A2 | 1/2015 |
| WO | WO 2015/075011 | 5/2015 |
| WO | WO 2016/061389 A2 | 4/2016 |
| WO | WO 2017/009312 A1 | 1/2017 |
| WO | WO 2017/207739 A1 | 12/2017 |

OTHER PUBLICATIONS

International Search Report and Written Opinion dated Nov. 10, 2016 for Application No. PCT/EP2016/066476.

International Search Report and Written Opinion dated Mar. 6, 2018 in connection with PCT/EP2017/079153.

International Search Report and Written Opinion dated Mar. 26, 2018 in connection with PCT/EP2017/083994.

International Search Report and Written Opinion dated May 2, 2018 in connection with PCT/EP2017/082749.

Ahmed et al. A novel in vivo model of tau propagation with rapid and progressive neurofibrillary tangle pathology: the pattern of spread is determined by connectivity, not proximity. Acta Neuropathol. May 2014;127(5):667-83. doi: 10.1007/s00401-014-1254-6. Epub Feb. 16, 2014.

Allen et al., Abundant tau filaments and nonapoptotic neurodegeneration in transgenic mice expressing human P301S tau protein. J Neurosci. Nov. 1, 2002;22(21):9340-51.

Altschul, Amino acid substitution matrices from an information theoretic perspective. J Mol Biol. Jun. 5, 1991;219(3):555-65.

Aslanidis et al., Ligation-independent cloning of PCR products (LIC-PCR). Nucleic Acids Res. Oct. 25, 1990;18(20):6069-74.

Bae et al., Antibody-aided clearance of extracellular α-synuclein prevents cell-to-cell aggregate transmission. J Neurosci. Sep. 26, 2012;32(39):13454-69.

Barderas et al.,Affinity Maturation Of Antibodies Assisted By In Silico Modeling. Proc. Natl. Acad. Sci. (USA)2008;105(26):9029-9034.

Bassil et al., Reducing C-terminal truncation mitigates synucleinopathy and neurodegeneration in a transgenic model of multiple system atrophy. Proc Natl Acad Sci U S A. Aug. 23, 2016;113(34):9593-8. doi: 10.1073/pnas.1609291113. Epub Aug. 1, 2016.

Besong-Agbo et al., Naturally occurring α-synuclein autoantibody levels are lower in patients with Parkinson disease. Neurology. Jan. 8, 2013;80(2):169-75. doi: 10.1212/WNL.0b013e31827b90d1. Epub Dec. 19, 2012.

Beyer et al., α-Synuclein posttranslational modification and alternative splicing as a trigger for neurodegeneration. Mol Neurobiol. Apr. 2013;47(2):509-24. doi: 10.1007/s12035-012-8330-5. Epub Aug. 25, 2012.

Bird et al., Single-chain antigen-binding proteins. Science. Oct. 21, 1988; 242:423-6.

Bostrom et al., Improving Antibody Binding Affinity And Specificity For Therapeutic Development. Methods Mol. Biol. 2009;525:353-376.

Braak et al., Evolution of the neuropathology of Alzheimer's disease. Acta Neurol Scand Suppl. 1996;165:3-12.

Braak et al., Neuropathology of Alzheimer's disease: what is new since A. Alzheimer? Eur Arch Psychiatry Clin Neurosci. 1999;249 Suppl 3:14-22.

Breteler et al., A community-based study of dementia: the Rotterdam Elderly Study. Neuroepidemiology. 1992;11 Suppl 1:23-8.

Broering et al., Identification and characterization of broadly neutralizing human monoclonal antibodies directed against the E2 envelope glycoprotein of hepatitis C virus. J Virol. Dec. 2009;83(23):12473-82. doi: 10.1128/JVI.01138-09. Epub Sep. 16, 2009.

Carter et al., Humanization Of An Anti-p185her2 Antibody For Human Cancer Therapy. Proc. Natl. Acad. Sci. (U.S.A.) May 1992; 89:4285-4289.

Chen et al., Immunoglobulin gene rearrangement in B cell deficient mice generated by targeted deletion. International Immunology. 1993;5(6):647-656.

Chen et al., B cell development in mice that lack one or both immunoglobulin kappa light chain genes. EMBO J. Mar. 1993;12(3):821-30.

Chen et al., Enhancement and destruction of antibody function by somatic mutation: unequal occurrence is controlled by V gene combinatorial associations. EMBO J. Jun. 15, 1995;14(12):2784-94.

Chothia et al., Canonical structures For The Hypervariable domains Of Immunoglobulins. J. Mol. Biol. (1987) 196, 901-917.

Clackson et al., Making antibody fragments using phage display libraries. Nature. 1991;352: 624-628.

Clavaguera et al., Brain homogenates from human tauopathies induce tau inclusions in mouse brain. Proc Natl Acad Sci U S A. Jun. 4, 2013;110(23):9535-40. doi: 10.1073/pnas.1301175110. Epub May 20, 2013.

Clavaguera et al., Peripheral administration of tau aggregates triggers intracerebral tauopathy in transgenic mice. Acta Neuropathol. Feb. 2014;127(2):299-301. doi: 10.1007/s00401-013-1231-5. Epub Dec. 21, 2013.

Clavaguera et al., Transmission and spreading of tauopathy in transgenic mouse brain. Nat Cell Biol. Jul. 2009;11(7):909-13. doi: 10.1038/ncb1901. Epub Jun. 7, 2009. Author manuscript.

Co et al., Chimeric And Humanized Antibodies With Specificity For The CD33 Antigen. J. Immunol. 1992; 148:1149-1154.

Co et al., Humanized Antibodies For Antiviral Therapy. Proc. Natl. Acad. Sci. (U.S.A.) (1991) 88:2869-2.

Conway et al., Acceleration of oligomerization, not fibrillization, is a shared property of both α-synuclein mutations linked to early-onset Parkinson's disease: Implications for pathogenesis and therapy. Proc Natl Acad Sci USA (2000) 97(2):571-576.

(56) References Cited

OTHER PUBLICATIONS

Crary et al., Primary age-related tauopathy (PART): a common pathology associated with human aging. Acta Neuropathol. Dec. 2014;128(6):755-66. doi: 10.1007/s00401-014-1349-0. Epub Oct. 28, 2014. Author manuscript.

Czapski et al., Extracellular alpha-synuclein induces calpain-dependent overactivation of cyclin-dependent kinase 5 in vitro. FEBS Lett. Sep. 17, 2013;587(18):3135-41.

Daher et al., Leucine-rich Repeat Kinase 2 (LRRK2) Pharmacological Inhibition Abates α-Synuclein Gene-induced Neurodegeneration. J Biol Chem. Aug. 7, 2015;290(32):19433-44. doi: 10.1074/jbc.M115.660001. Epub Jun. 15, 2015.

Derkinderen et al., Gut feelings about smoking and coffee in Parkinson's disease. Mov Disord. Jul. 2014;29(8):976-9.

Di Scala et al., Common molecular mechanism of amyloid pore formation by Alzheimer's β-amyloid peptide and α-synuclein. Sci Rep. Jun. 29, 2016;6:28781. doi: 10.1038/srep28781.

Dufty et al., Calpain-cleavage of alpha-synuclein: connecting proteolytic processing to disease-linked aggregation. Am J Pathol. May 2007;170(5):1725-38.

Dumont et al., Human cell lines for biopharmaceutical manufacturing: history, status, and future perspectives. Crit Rev Biotechnol. Dec. 2016;36(6):1110-1122. Epub Sep. 18, 2015. Review.

Eddy, Where Did The BLOSUM62 Alignment Score Matrix Come From? Nature Biotech. 2004;22(8):1035-1036.

Elgert, Chapter 4:"Antibody Structure and Function." Immunology: Understanding the Immune System. John Wiley & Sons, Inc. 1998; p. 58-78.

Elvang et al., Differential effects of gamma-secretase and BACE1 inhibition on brain Abeta levels in vitro and in vivo. J Neurochem. Sep. 2009;110(5):1377-87. doi: 10.1111/j.1471-4159.2009.06215.x. Epub Jun. 10, 2009.

Emadi et al., Isolation of a human single chain antibody fragment against oligomeric alpha-synuclein that inhibits aggregation and prevents alpha-synuclein-induced toxicity. J Mol Biol. May 11, 2007;368(4):1132-44. Epub Mar. 7, 2007. Author manuscript.

Emanuele et al., Exogenous Alpha-Synuclein Alters Pre- and Post-Synaptic Activity by Fragmenting Lipid Rafts. EBioMedicine. May 2016;7:191-204. doi: 10.1016/j.ebiom.2016.03.038. Epub Apr. 5, 2016.

Evans et al., Rapid expression of an anti-human C5 chimeric Fab utilizing a vector that replicates in COS and 293 cells. J Immunol Methods. Jul. 17, 1995;184(1):123-38.

Finlay et al., Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions. 2009; J. Mol. Biol. 388(3):541-558.

Fishwild et al., High-avidity human IgG kappa monoclonal antibodies from a novel strain of minilocus transgenic mice. Nat Biotechnol. Jul. 1996;14(7):845-51.

Fleming et al., Behavioral phentoypes and pharmacology in genetic mouse models of Parkinsonism. Behav Pharmacol. Sep. 2006;17(5-6):383-91.

Foote et al., Antibody framework residues affecting the conformation of the hypervariable loops. J Mol Biol. Mar. 20, 1992;224(2):487-99.

Galasko et al., Clinical-neuropathological correlations in Alzheimer's disease and related dementias. Arch Neurol. Sep. 1994;51(9):888-95.

Galpern et al., Interface between tauopathies and synucleinopathies: a tale of two proteins. Mar. 2006;59(3):449-58.

Games et al., Axonopathy in an α-synuclein transgenic model of Lewy body disease is associated with extensive accumulation of C-terminal-truncated α-synuclein. Am J Pathol. Mar. 2013;182(3):940-53. doi: 10.1016/j.ajpath.2012.11.018. Epub Jan. 9, 2013.

Games et al., Reducing C-terminal-truncated alpha-synuclein by immunotherapy attenuates neurodegeneration and propagation in Parkinson's disease-like models. J Neurosci. Jul. 9, 2014;34(28):9441-54.

Gardai et al., Elevated alpha-synuclein impairs innate immune cell function and provides a potential peripheral biomarker for Parkinson's disease. PLoS One. Aug. 23, 2013;8(8):e71634. doi: 10.1371/journal.pone.0071634. eCollection 2013.

Giasson et al., Initiation and synergistic fibrillization of tau and alpha-synuclein. Science. Apr. 25, 2003;300(5619):636-40.

Glaser et al. Antibody engineering by codon-based mutagenesis in a filamentous phage vector system. J Immunol. Dec. 15, 1992;149(12):3903-13.

Gonzales et al., SDR Grafting Of A Murine Antibody Using Multiple Human Germline Templates To Minimize Its Immunogenicity. Mol. Immunol. 2004;41:863-872.

Gorman et al., Reshaping A Therapeutic CD4 Antibody. Proc. Natl. Acad. Sci. (U.S.A.) May 1991;88:4181-4185.

Gruden et al., Correlation between protective immunity to α-synuclein aggregates, oxidative stress and inflammation. Neuroimmunomodulation. 2012;19(6):334-42. doi: 10.1159/000341400. Epub Sep. 11, 2012.

Gruden et al., Immunoprotection against toxic biomarkers is retained during Parkinson's disease progression. J Neuroimmunol. Apr. 2011;233(1-2):221-7.

Guerrero-Muñoz et al., Amyloid-β oligomers as a template for secondary amyloidosis in Alzheimer's disease. Neurobiol Dis. Nov. 2014;71:14-23. doi: 10.1016/j.nbd.2014.08.008. Epub Aug. 15, 2014.

Guilliams et al., Nanobodies raised against monomeric α-synuclein distinguish between fibrils at different maturation stages. J Mol Biol. Jul. 24, 2013;425(14):2397-411. doi: 10.1016/j.jmb.2013.01.040. Epub Apr. 1, 2013.

Gunasekaran et al. Enhancing antibody Fc heterodimer formation through electrostatic steering effects. JBC;2010:285(25):19637-46.

Guo el at., Distinct α-synuclein strains differentially promote tau inclusions in neurons. Cell. Jul. 3, 2013;154(1):103-17. doi: 10.1016/j.cell.2013.05.057.

Gustchina et al., Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth. Virology. 2009;393(1):112-119.

Hackel et al., Stability And CDR Composition Biases Enrich Binder Functionality Landscapes. J. Mol. Biol. 2010;401(1):84-96.

Hall et al. Behavioural deficits in transgenic mice expressing human truncated (1-120 amino acid) alpha-synuclein. Exp Neurol. Feb. 2015;264:8-13. doi: 10.1016/j.expneurol.2014.11.003. Epub Nov. 20, 2014.

Hansen et al. α-Synuclein propagates from mouse brain to grafted dopaminergic neurons and seeds aggregation in cultured human cells. J Clin Invest. Feb. 2011;121(2):715-25. doi: 10.1172/JCI43366. Epub Jan. 18, 2011.

Hansen et al., Beyond α-synuclein transfer: pathology propagation in Parkinson's disease. Trends Mol Med. May 2012;18(5):248-55. doi: 10.1016/j.molmed.2012.03.002. Epub Apr. 13, 2012. Review.

Harding et al., Class switching in human immunoglobulin transgenic mice. Ann. N. Y. Acad. Sci. 1995;764:536-546.

He et al., Inhibition of Rho-kinase by Fasudil protects dopamine neurons and attenuates inflammatory response in an intranasal lipopolysaccharide-mediated Parkinson's model. Eur J Neurosci. Jan. 2016;43(1):41-52. doi: 10.1111/ejn.13132. Epub Dec. 28, 2015.

Henikoff et al., Amino acid substitution matrices from protein blocks. Proc. Natl. Acad. Sci. (USA). Nov. 1992;89:10915-10919.

Hepp et al., Distribution and load of amyloid-β pathology in Parkinson disease and dementia with Lewy bodies. J Neuropathol Exp Neurol. Oct. 2016;75(10):936-945.

Holliger et al., "Diabodies": small bivalent and bispecific antibody fragments. Proc Natl Acad Sci U S A. Jul. 15, 1993;90(14):6444-8.

Holmes et al., Proteopathic tau seeding predicts tauopathy in vivo. Proc Natl Acad Sci U S A. Oct. 14, 2014;111(41):E4376-85. doi: 10.1073/pnas.1411649111. Epub Sep. 26, 2014.

Holt et al., Domain antibodies: proteins for therapy. Trends Biotechnol. Nov. 2003;21(11) :484-90.

(56) References Cited

OTHER PUBLICATIONS

Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Jack et al., Tracking pathophysiological processes in Alzheimer's disease: an updated hypothetical model of dynamic biomarkers. Lancet Neurol. Feb. 2013;12(2):207-16. doi: 10.1016/S1474-4422(12)70291-0. Author manuscript.
Jakes et al., Epitope mapping of LB509, a monoclonal antibody directed against human alpha-synuclein. Neurosci Lett. Jul. 2, 1999;269(1):13-6.
Jellinger, Neuropathology of sporadic Parkinson's disease: evaluation and changes of concepts. Mov Disord. Jan. 2012;27(1):8-30.
Kabiraj et al., An 11-mer Amyloid Beta Peptide Fragment Provokes Chemical Mutations and Parkinsonian Biomarker Aggregation in Dopaminergic Cells: A Novel Road Map for "Transfected" Parkinson's. ACS Chem Neurosci. Nov. 16, 2016;7(11):1519-1530. Epub Oct. 3, 2016.
Karlin et al., Methods For Assessing The Statistical Significance Of Molecular Sequence Features By Using General Scoring Schemes. Proc. Natl. Acad. Sci. (USA). 1990;87:2264-2268.
Kellie et al., Quantitative measurement of intact alpha-synuclein proteoforms from postmortem control and Parkinson's disease brain tissue by mass spectrometry. Sci Rep. Jul. 23, 2014;4:5797. doi: 10.1038/srep05797.
Kettleborough et al., Humanization Of A Mouse Monoclonal Antibody By CDR-Grafting: The Importance Of Framework Residues On Loop Conformation. Protein Engineering. 1991;4:773-3783.
Kim et al., Hypoestoxide reduces neuroinflammation and α-synuclein accumulation in a mouse model of Parkinson's disease. J Neuroinflammation. Dec. 18, 2015;12:236. doi: 10.1186/s12974-015-0455-9.
Kim et al., Non-cell-autonomous Neurotoxicity of α-synuclein Through Microglial Toll-like Receptor 2. Exp Neurobiol. Jun. 2016;25(3):113-9. doi: 10.5607/en.2016.25.3.113. Epub Jun. 8, 2016.
Kirik et al., Modeling CNS neurdegeneration by overexpression of disease-causing proteins using viral vectors. Trends Neurosci. Jul. 2003;26(7):386-92.
Kirik et al., Parkinson-like neurodegeneration induced by targeted overexpression of alpha-synuclein in the nigrostriatal system. J Neurosci. Apr. 1, 2002;22(7):2780-91.
Koehler et al., Altered serum IgG levels to α-synuclein in dementia with Lewy bodies and Alzheimer's disease. PLoS One. May 31, 2013;8(5):e64649. doi: 10.1371/journal.pone.0064649. Print 2013.
Köhler et al., Continuous cultures of fused cells secreting antibody of predefined specificity. Nature. Aug. 7, 1975;256(5517):495-7.
Krause et al., An Insertion Mutation That Distorts Antibody Binding Site Architecture Enhances Function Of A Human Antibody. MBio. Feb. 8, 2011;2(1):e00345-10. doi: 10.1128/mBio.00345-10.
Kruger et al., Ala30Pro mutation in the gene encoding alpha-synuclein in Parkinson's disease. Nat Genet. Feb. 1998;18(2):106-8.
Kuan et al., Affinity-matured anti-glycoprotein NMB recombinant immunotoxins targeting malignant gliomas and melanomas. Int J Cancer. Jul. 1, 2011;129(1):111-21. doi: 10.1002/ijc.25645. Epub Nov. 3, 2010.
Labrijn et al., Efficient generation of stable bispecific IgG1 by controlled Fab-arm exchange. Proc Natl Acad Sci U S A. Mar. 26, 2013;110(13):5145-50. doi: 10.1073/pnas.1220145110. Epub Mar. 11, 2013.
Lambert et al., Meta-analysis of 74,046 individuals identifies 11 new susceptibility loci for Alzheimer's disease. Nat Genet. Dec. 2013;45(12):1452-8. doi: 10.1038/ng.2802. Epub Oct. 27, 2013. Author manuscript.
Launer, Overview of incidence studies of dementia conducted in Europe. Neuroepidemiology. 1992;11 Suppl 1:2-13.
Lee et al., Extracellular α—synuclein—a novel and crucial factor in Lewy body diseases. Nat Rev Neurol. Feb. 2014;10(2):92-8. doi: 10.1038/nrneurol.2013.275. Epub Jan. 28, 2014. Review.
Lee et al., Mechanisms of Parkinson's disease linked to pathological alpha-synuclein: new targets for drug discovery. Neuron. Oct. 5, 2006;52(1):33-8. Review.
Lindstrom et al., Immunotherapy targeting α-synuclein protofibrils reduced pathology in (Thy-1)-h[A30P] α-synuclein mice. Neurobiol Dis. Sep. 2014;69:134-43. doi: 10.1016/j.nbd.2014.05.009. Epub May 20, 2014.
Lobuglio et al.,Mouse/Human Chimeric Monoclonal Antibody In Man: Kinetics And Immune Response. Proc. Natl. Acad. Sci. (U.S.A.). 1989 86:4220-4224.
Loiodice et al., Pramipexole induced place preference after L-dopa therapy and nigral dopaminergic loss: linking behavior to transcriptional modifications. Psychopharmacology (Berl). Jan. 2017;234(1):15-27. doi: 10.1007/s00213-016-4430-7. Epub Sep. 10, 2016.
Lonberg et al., Antigen-specific human antibodies from mice comprising four distinct genetic modifications. Nature. Apr. 28, 1994;368(6474):856-9.
Lonberg et al., Human antibodies from transgenic mice. Intern. Rev. Immunol. 1995;13:65-93.
Lorenzo et al. Prediction of Spontaneous Protein Deamidation from Sequence-Derived Secondary Structure and Intrinsic Disorder. PLoS One. Dec. 16, 2015;10(12):e0145186. doi: 10.1371/journal.pone.0145186. eCollection 2015.
Luk et al., Intracerebral inoculation of pathological α-synuclein initiates a rapidly progressive neurodegenerative α-nucleinopathy in mice. J Exp Med. May 7, 2012;209(5):975-86. doi: 10.1084/jem.20112457. Epub Apr. 16, 2012.
Luk et al., Pathological α-Synuclein transmission initiates Parkinson-like neurodegeneration in nontransgenic mice. Science. Nov. 16, 2012;338(6109):949-53.
Luo et al., Effects of pramipexole treatment on the α-synuclein content in serum exosomes of Parkinson's disease patients. Exp Ther Med. Sep. 2016;12(3):1373-1376. Epub Jun. 21, 2016.
Ma et al., Advances with microRNAs in Parkinson's disease research. Drug Des Devel Ther. Oct. 1, 2013;7:1103-13. doi: 10.2147/DDDT.S48500. eCollection 2013.
Mabry et al., Engineering of stable bispecific antibodies targeting IL-17A and IL-23. PEDS. 2010;23(3):115-127.
Maeda et al., Construction Of Reshaped Human Antibodies With HIV-Neutralizing Activity. Human Antibodies Hybridoma. 1991;2:124-34.
Maetzler et al., Comparable autoantibody serum levels against amyloid- and inflammation-associated proteins in Parkinson's disease patients and controls. PLoS One. Feb. 21, 2014;9(2):e88604. doi: 10.1371/journal.pone.0088604. eCollection 2014.
Mahowald et al., When and where do synucleinopathies begin? Neurology (2010) 75:488-489.
Maingay et al., Viral vector mediated overexpression of human alpha-synuclein in the nigrostriatal dopaminergic neurons: a new model for Parkinson's disease. CNS Spectr. Mar. 2005;10(3):235-44. Review.
Mao et al., Pathological α-synuclein transmission initiated by binding lymphocyte-activation gene 3. Science. Sep. 30, 2016;353(6307). pii: aah3374.
Marks et al., By-passing immunization human antibodies from V-gene libraries displayed on phage. J. Mol. Biol. 1991;222: 581-597.
Mazzulli et al., Activation of β-Glucocerebrosidase Reduces Pathological β-Synuclein and Restores Lysosomal Function in Parkinson's Patient Midbrain Neurons. J Neurosci. Jul. 20, 2016;36(29):7693-706. doi: 10.1523/JNEUROSCI.0628-16.2016.
McCafferty et al., Phage antibodies: filamentous phage displaying antibody variable domains. Nature. 1990;348:552-4.
McKeith et al., Consensus guidelines for the clinical and pathologic diagnosis of dementia with Lewy bodies (DLB): Report of the consortium on DLB international workshop. Neurology (1996) 47:1113-24.
Metz et al., Bispecific antibody derivatives with restricted binding functionalities that are activated by proteolytic processing. Protein Eng Des Sel. Oct. 2012;25(10):571-80. Epub Sep. 13, 2012.
Mishizen-Eberz et al., Cleavage of alpha-synuclein by calpain: potential role in degradation of fibrillized and nitrated species of alpha-synuclein. Biochemistry. 2005;44:7818-29.

(56) References Cited

OTHER PUBLICATIONS

Mishizen-Eberz et al., Distinct cleavage patterns of normal and pathologic forms of alpha-synuclein by calpain I in vitro. J Neurochem. Aug. 2003;86(4):836-47.
Montgomery et al., Affinity Maturation And Characterization Of A Human Monoclonal Antibody Against HIV-1 gp41. Mabs. 2009;1(5):462-474.
Moore et al., A novel bispecific antibody format enables simultaneous bivalent and monovalent co-engagement of distinct target antigens. Mabs. 2011;3(6):546-557.
Mukherjee et al., Production and characterization of protective human antibodies against Shiga toxin 1. Infect Immun. Oct. 2002;70(10):5896-9.
Nelson et al., Correlation of Alzheimer disease neuropathologic changes with cognitive status: a review of the literature. J Neuropathol Exp Neurol. May 2012;71(5):362-81. doi: 10.1097/NEN.0b013e31825018f7.
Nemani et al., Increased expression of alpha-synuclein reduces neurotransmitter release by inhibiting synaptic vesicle reclustering after endocytosis. Neuron. Jan. 14, 2010;65(1):66-79. doi: 10.1016/j.neuron.2009.12.023.
Oikawa et al., α-Synuclein Fibrils Exhibit Gain of Toxic Function, Promoting Tau Aggregation and Inhibiting Microtubule Assembly. J Biol Chem. Jul. 15, 2016;291(29):15046-56. doi: 10.1074/jbc.M116.736355. Epub May 19, 2016.
Pacheco et al., Extracellular α-synuclein alters synaptic transmission in brain neurons by perforating the neuronal plasma membrane. J Neurochem. Mar. 2015;132(6):731-41. doi: 10.1111/jnc.13060. Epub Feb. 25, 2015.
Papachroni et al., Autoantibodies to alpha-synuclein in inherited Parkison's disease. J Neurochem. May 2007;101(3):749-56.
Paumier et al., Behavioral characterization of A53T mice reveals early and late stage deficits related to Parkinson's disease. PLoS One. Aug. 1, 2013;8(8):e70274. doi: 10.1371/journal.pone.0070274. Print 2013.
Peelaerts et al., α-Synuclein strains cause distinct synucleinopathies after local and systemic administration. Nature. Jun. 18, 2015;522(7556):340-4. doi: 10.1038/nature14547. Epub Jun. 10, 2015.
Polymeropoulos et al., Mutation in the alpha-synuclein gene identified in families with Parkinson's disease. Science. Jun. 27, 1997;276(5321):2045-7.
Probst et al., Axonopathy and amyotrophy in mice transgenic for human four-repeat tau protein. Acta Neuropathol. May 2000;99(5):469-81.
Recasens et al., Lewy body extracts from Parkinson disease brains trigger α-synuclein pathology and neurodegeneration in mice and monkeys. Ann Neurol. Mar. 2014;75(3):351-62. doi: 10.1002/ana.24066. First published Nov. 16, 2013.
Reglodi et al., Novel tactics for neuroprotection in Parkinson's disease: Role of antibiotics, polyphenols and neuropeptides. Prog Neurobiol. Aug. 2017;155:120-148. doi: 10.1016/j.pneurobio.2015.10.004. Epub Nov. 2, 2015. Review.
Revets et al., Nanobodies as novel agents for cancer therapy. Expert Opin Biol Ther. 2005; 5(1): 111-24. DOI: 10.1517/14712598.5.1.111.
Ridgway et al., 'Knobs-into-holes' engineering of antibody CH3 domains for heavy chain heterodimerization. Protein Eng. Jul. 1996;9(7):617-21.
Riechmann et al., Reshaping Human Antibodies for Therapy. Nature. 1988;332:323-327.
Ritchie et al, Alpha-synuclein truncation and disease. Health. 2012;4(Special Issue):1167-1177.
Rudikoff et al., Single Amino Acid Substitution Altering Antigen-Binding Specificity. Proc. Natl. Acad. Sci. (USA). 1982;79(6):1979-1983.
Sahara et al., Characteristics of TBS-extractable hyperphosphorylated tau species: aggregation intermediates in rTg4510 mouse brain. J Alzheimers Dis. 2013;33(1):249-63. doi: 10.3233/JAD-2012-121093. Author manuscript.
Sato et al., Reshaping a human antibody to inhibit the interleukin 6-dependent tumor cell growth. Cancer Res. Feb. 15, 1993;53(4):851-6.
Schelle et al.,Prevention of tau increase in cerebrospinal fluid of APP transgenic mice suggests downstream effect of BACE1 inhibition. Alzheimers Dement. Jun. 2017;13(6):701-709. doi: 10.1016/j.jalz.2016.09.005. Epub Oct. 14, 2016.
Schier et al., Isolation of picomolar affinity anti-c-erbB-2 single-chain Fv by molecular evolution of the complementarity determining regions in the center of the antibody binding site. J Mol Biol. Nov. 8, 1996;263(4):551-67.
Shahaduzzaman et al., Anti-human α-synuclein N-terminal peptide antibody protects against dopaminergic cell death and ameliorates behavioral deficits in an AAV-α-synuclein rat model of Parkinson's disease. PLoS One. Feb. 6, 2015;10(2):e0116841. doi: 10.1371/journal.pone.0116841. eCollection 2015.
Smith et al., α-Synuclein and anti-α-synuclein antibodies in Parkinson's disease, atypical Parkinson syndromes, REM sleep behavior disorder, and healthy controls. PLoS One. 2012;7(12):e52285. doi:10.1371/journal.pone.0052285. Epub Dec. 17, 2012.
Spencer et al., ESCRT-mediated uptake and degradation of brain-targeted α-synuclein single chain antibody attenuates neuronal degeneration in vivo. Mol Ther. Oct. 2014;22(10):1753-67. doi: 10.1038/mt.2014.129. Epub Jul. 10, 2014.
Spencer et al., Reducing Endogenous α-Synuclein Mitigates the Degeneration of Selective Neuronal Populations in an Alzheimer's Disease Transgenic Mouse Model. J Neurosci. Jul. 27, 2016;36(30):7971-84. doi:10.1523/JNEUROSCI.0775-16.2016.
Spillantini et al., Alpha-synuclein in Lewy bodies. Nature. Aug. 28, 1997;388(6645):839-40.
Spreter Von Kreudenstein et al., Improving biophysical properties of a bispecific antibody scaffold to aid developability. Mabs. 2013;5(5):646-654.
Springer et al., Mechanisms and models of α-synuclein-related neurodegeneration. Curr Neurol Neurosci Rep. Sep. 2006;6(5):432-6.
Steidl et al., In Vitro Affinity Maturation Of Human GM-CSF Antibodies By Targeted CDR-Diversification. 2008 Mol. Immunol. 46(1):135-144.
Strop et al., Generating bispecific human IgG1 and IgG2 antibodies from any antibody pair. JMB. 2012;420:204-219.
Surmeier et al., Calcium and Parkinson's disease. Biochem Biophys Res Commun. Feb. 19, 2017;483(4):1013-1019. doi: 10.1016/j.bbrc.2016.08.168. Epub Aug. 30, 2016. Review.
Takeda et al., Abnormal accumulation of NACP/alpha-synuclein in neurodegenerative disorders. Am J Pathol. Feb. 1998;152(2):367-72.
Tavassoly et al., The use of nanopore analysis for discovering drugs which bind to α-synuclein for treatment of Parkinson's disease. Eur J Med Chem. Dec. 17, 2014;88:42-54. doi: 10.1016/j.ejmech.2014.07.090. Epub Jul. 25, 2014.
Taylor et al., L. et al., Human immunoglobulin transgenes undergo rearrangement, somatic mutation and class switching in mice that lack endogenous IgM. Int Immunol. Apr. 1994;6(4):579-91.
Taylor et al., A transgenic mouse that expresses a diversity of human sequence heavy and light chain immunoglobulins. Nucleic Acids Res. Dec. 11, 1992;20(23):6287-95.
Tempest et al., Reshaping A Human Monoclonal Antibody To Inhibit Human Respiratory Syncytial Virus Infection in vivo. Bio/Technology. 1991; 9:266-271.
Tofaris et al., Pathological changes in dopaminergic nerve cells of the substantia nigra and olfactory bulb in mice transgenic for truncated human alpha-synuclein(1-120): implications for Lewy body disorders. J Neurosci. Apr. 12, 2006;26(15):3942-50.
Tóth et al., Targeting the intrinsically disordered structural ensemble of α-synuclein by small molecules as a potential therapeutic strategy for Parkinson's disease. PLoS One. Feb. 14, 2014;9(2):e87133. doi: 10.1371/journal.pone.0087133. eCollection 2014. Erratum in: PLoS One. 2014;9(5):e99274.
Tran et al., A-synuclein immunotherapy blocks uptake and templated propagation of misfolded α-synuclein and neurodegeneration. Cell Rep. Jun. 26, 2014;7(6):2054-65. doi: 10.1016/j.celrep.2014.05.033. Epub Jun. 12, 2014.

(56) References Cited

OTHER PUBLICATIONS

Tuaillon et al., Biased utilization of DHQ52 and JH4 gene segments in a human Ig transgenic minilocus is independent of antigenic selection. J Immunol. Mar. 15, 1994;152(6):2912-20.
Ulusoy et al., Co-expression of C-terminal truncated alpha-synuclein enhances full-length alpha-synuclein-induced pathology. Eur J Neurosci. Aug. 2010;32(3):409-22. doi: 10.1111/j.1460-9568.2010.07284.x.
Vaikath et al., Generation and characterization of novel conformation-specific monoclonal antibodies for α-synuclein pathology. Neurobiol Dis. Jul. 2015;79:81-99. doi: 10.1016/j.nbd.2015.04.009. Epub Apr. 30, 2015.
Valera et al., Immunotherapy for neurodegenerative diseases: focus on α-synucleinopathies. Pharmacol Ther. Jun. 2013;138(3):311-22. doi: 10.1016/j.pharmthera.2013.01.013. Epub Feb. 4, 2013. Author manuscript.
Vekrellis et al., Pathological roles of α-synuclein in neurological disorders. Lancet Neurol. Nov. 2011;10(11):1015-25.
Verhoeyen et al., Reshaping Human Antibodies: Grafting An Antilysozyme Activity. Science. 1988. 239:1534-1536.
Volles et al., Zeroing in on the pathogenic form of α-synuclein and its mechanism of neurotoxicity in Parkinson's disease. J. Biochem. 42:7871-7878, 2003.
Volpicelli-Daley et al., Exogenous α-synuclein fibrils induce Lewy body pathology leading to synaptic dysfunction and neuron death. Neuron. Oct. 6, 2011;72(1):57-71. doi: 10.1016/j.neuron.2011.08.033.
Wakabayashi et al., NACP, a presynaptic protein, immunoreactivity in Lewy bodies in Parkinson's disease. Neurosci Lett. Dec. 12, 1997;239(1):45-8.
Wakamatsu et al.,Selective loss of nigral dopamine neurons induced by overexpression of truncated human alpha-synuclein in mice. Neurobiol Aging. Apr. 2008;29(4):574-85. Epub Dec. 14, 2006.
Walker et al., Mechanisms of protein seeding in neurodegenerative diseases. JAMA Neurol. Mar. 1, 2013;70(3):304-10.
Wang et al., Caspase-1 causes truncation and aggregation of the Parkinson's disease-associated protein α-synuclein. Proc Natl Acad Sci U S A. Aug. 23, 2016;113(34):9587-92. doi: 10.1073/pnas.1610099113. Epub Aug. 1, 2016.
Ward et al., Binding activities of a repertoire of single immunoglobulin variable domains secreted from *Escherichia coli*. Nature. Oct. 12, 1989;341(6242):544-6.
Waxman et al., Induction of intracellular tau aggregation is promoted by α-synuclein seeds and provides novel insights into the hyperphosphorylation of tau. J Neurosci. May 25, 2011;31(21):7604-18. doi: 10.1523/JNEUROSCI.0297-11.2011.
Weiner et al., Impact of the Alzheimer's Disease Neuroimaging Initiative, 2004 to 2014. Alzheimers Dement. Jul. 2015;11(7):865-84. doi: 10.1016/j.jalz.2015.04.005. Author manuscript.
Westerlund et al., Lrrk2 and alpha-synuclein are co-regulated in rodent striatum. Mol Cell Neurosci. Dec. 2008;39(4):586-91. doi: 10.1016/j.mcn.2008.08.001. Epub Aug. 27, 2008.
Woerman et al., Propagation of prions causing synucleinopathies in cultured cells. Proc Natl Acad Sci U S A. Sep. 1, 2015;112(35):E4949-58. doi: 10.1073/pnas.1513426112. Epub Aug. 18, 2015.
Woulfe et al., Absence of elevated anti-alpha-synuclein and anti-EBV latent membrane protein antibodies in PD. Neurology. May 14, 2002;58(9):1435-6.
Wrasidlo et al., A de novo compound targeting α-synuclein improves deficits in models of Parkinson's disease. Brain. Dec. 2016;139(Pt 12):3217-3236. Epub Sep. 27, 2016.
Wu et al., Stepwise in vitro affinity maturation of Vitaxin, an alphav beta3-specific humanized mAb. Proc Natl Acad Sci U S A. May 26, 1998;95(11):6037-42.
Xu et al., CMV-beta-actin promoter directs higher expression from an adeno-associated viral vector in the liver than the cytomegalovirus or elongation factor 1 alpha promoter and results in therapeutic levels of human factor X in mice. Hum Gene Ther. Mar. 20, 2001; 12(5):563-73.
Xu et al., Epigallocatechin Gallate (EGCG) Inhibits Alpha-Synuclein Aggregation: A Potential Agent for Parkinson's Disease. Neurochem Res. Oct. 2016;41(10):2788-2796. Epub Jun. 30, 2016.
Yamada, Senile dementia of the neurofibrillary tangle type (tangle-only dementia): neuropathological criteria and clinical guidelines for diagnosis. Neuropathology. Dec. 2003;23(4):311-7. Abstract only.
Yanamandra et al., Anti-tau antibodies that block tau aggregate seeding in vitro markedly decrease pathology and improve cognition in vivo. Neuron. Oct. 16, 2013;80(2):402-414. doi: 10.1016/j.neuron.2013.07.046. Epub Sep. 26, 2013.
Yanamandra et al., α-synuclein reactive antibodies as diagnostic biomarkers in blood sera of Parkinson's disease patients. PLoS One. Apr. 25, 2011;6(4):e18513. doi: 10.1371/journal.pone.0018513.
Yap et al., Alpha-synuclein interacts with Glucocerebrosidase providing a molecular link between Parkinson and Gaucher diseases. J Biol Chem. Aug. 12, 2011;286(32):28080-8. doi: 10.1074/jbc.M111.237859. Epub Jun. 8, 2011.
Yap et al., Membrane-bound α-synuclein interacts with glucocerebrosidase and inhibits enzyme activity. Mol Genet Metab. Jan. 2013;108(1):56-64. doi: 10.1016/j.ymgme.2012.11.010. Epub Nov. 28, 2012.
Yelton et al., Affinity maturation of the BR96 anti-carcinoma antibody by codon-based mutagenesis. J Immunol. Aug. 15, 1995;155(4):1994-2004.
Zou et al., Gene targeting in the Ig kappa locus: efficient generation of lambda chain-expressing B cells, independent of gene rearrangements in Ig kappa. EMBO J. Mar. 1993;12(3):811-20.
[No Author Listed] Wikipedia: Parkinson's disease. 2004; last updated Feb. 21, 2020. Retrieved from the Internet under https://en.wikipedia.org/wiki/Parkinson%27s_disease on Jan. 29, 2020. 36 pages.
[No Author Listed] Wikipedia: Pharmacological treatment of Parkinson's disease. 2014; last updated: Oct. 1, 2019. Retrieved from the Internet under https://en.wikipedia.org/wiki/Pharmacological_treatment_of_Parkinson%27s_disease on Sep. 23, 2019. 3 pages.
[No Author Listed] Wikipedia: Synucleinopathy. 2014; last updated: Aug. 25, 2019. Retrieved from the Internet under https://en.wikipedia.org/wiki/Synucleinopathy on Sep. 23, 2019. 3 pages.
International Search Report and Written Opinion dated Mar. 13, 2019 in connection with PCT/EP2018/085898.
Chartier-Harlin et al., Alpha-synuclein locus duplication as a cause of familial Parkinson's disease. Lancet. Sep. 25-Oct. 1, 2004;364(9440):1167-9. doi: 10.1016/S0140-6736(04)17103-1.
Degorce et al., HTRF: A technology tailored for drug discovery—a review of theoretical aspects and recent applications. Curr Chem Genomics. May 28, 2009;3:22-32. doi: 10.2174/1875397300903010022.
Dehay et al., Targeting α-synuclein for treatment of Parkinson's disease: mechanistic and therapeutic considerations. Lancet Neurol. Aug. 2015;14(8):855-866. Epub Jun. 3, 2015.
Goldman et al., Cerebrospinal fluid, plasma, and saliva in the BioFIND study: Relationships among biomarkers and Parkinson's disease Features. Mov Disord. Feb. 2018;33(2):282-288. doi: 10.1002/mds.27232. Epub Dec. 4, 2017.
Majbour et al., Oligomeric and phosphorylated alpha-synuclein as potential CSF biomarkers for Parkinson's disease. Mol Neurodegener. Jan. 19, 2016;11:7. doi: 10.1186/s13024-016-0072-9.
Polymeropoulos et al., Autosomal dominant Parkinson's disease and alpha-synuclein. Ann Neurol. Sep. 1998;44(3 Suppl 1):S63-4. doi: 10.1002/ana.410440710.
Simonsen et al., The utility of α-synuclein as biofluid marker in neurodegenerative diseases: a systematic review of the literature. Biomark Med. 2016;10(1):19-34. Epub Aug. 28, 2015.
Singleton et al., alpha-Synuclein locus triplication causes Parkinson's disease. Science. Oct. 31, 2003;302(5646):841. doi: 10.1126/science.1090278.
Zarranz et al., The new mutation, E46K, of alpha-synuclein causes Parkinson and Lewy body dementia. Ann Neurol. Feb. 2004;55(2):164-73. doi: 10.1002/ana.10795.
Zhao et al., AlphaLISA detection of alpha-synuclein in the cerebrospinal fluid and its potential application in Parkinson's disease diagnosis. Protein Cell. Sep. 2017;8(9):696-700.

a b a

ALPHA-SYNUCLEIN ANTIBODIES

CROSS-REFERENCE TO RELATED APPLICATIONS

This application is a National Stage filing under 35 U.S.C. 371 of International Patent Application No. PCT/EP2017/082749, filed Dec. 14, 2017, which claims foreign priority benefits under 35 U.S.C. § 119(a)-(d) or 35 U.S.C. § 365(b) of Danish Application No. PA201600769, filed Dec. 16, 2016. The entire contents of these applications are incorporated herein by reference in their entirety.

The present invention relates to a novel class of monoclonal antibody that specifically binds to alpha-synuclein, as well as to methods of using these molecules and their alpha-synuclein binding fragments in the treatment and diagnosis of synucleinopathies.

REFERENCE TO SEQUENCE LISTING

This application includes one or more Sequence Listings pursuant to 37 C.F.R. 1.821 et seq., which are disclosed in computer-readable media (file name: 1074-WO-PCT_ST25.txt, created on 11 Dec. 2017, and having a size of 43 kB), which file is herein incorporated by reference in its entirety.

BACKGROUND OF THE INVENTION

Synucleinopathies, also known as Lewy body diseases (LBDs), are characterized by deposition of intracellular protein aggregates microscopically visible as Lewy bodies (LBs) and/or Lewy neurites, where the protein alpha-synuclein is the major component (Jellinger, Mov Disord. 2012 January; 27(1):8-30; McKeith et al., Neurology (1996) 47:1113-24). Synucleinopathies include Parkinson's disease (including idiopathic and inherited forms of Parkinson's disease) and Diffuse Lewy Body (DLB) disease (also known as Dementia with Lewy Bodies (DLB), Lewy body variant of Alzheimer's disease (LBV), Combined Alzheimer's and Parkinson disease (PD), pure autonomic failure and multiple system atrophy (MSA; e.g., Olivopontocerebellar Atrophy, Striatonigral Degeneration and Shy-Drager Syndrome)). Synucleinopathies frequently have degeneration of the dopaminergic nigrostriatal system, responsible for the core motor deficits in Parkinsonism (rigidity, bradykinesia, resting tremor), but there is also widespread occurrence of Lewy bodies and dystrophic Lewy neurites in the central, peripheral and autonomic nervous system and brain regions and other organs associated with non-motor dysfunctions, such as dementia and autonomic nervous system deficits. Several of the non-motor signs and symptoms are thought to precede motor symptoms in Parkinson's disease and other synucleinopathies. Such early signs include, for example, REM sleep behaviour disorder (RBD) and loss of smell and constipation (Mahowald et al., Neurology (2010) 75:488-489). Synucleinopathies continue to be a common cause for movement disorders and cognitive deterioration in the aging population (Galasko et al., Arch. Neurol. (1994) 51:888-95).

Increased firing and altered firing patterns in the subthalamic nucleus (STN) are considered to contribute to the symptoms of PD and STN discharge in the parkinsonian state is strongly synchronized to cortical oscillatory activity (Shimamoto et al., J Neurosci. 2013 Apr. 24; 33(17):7220-33). In PD patients, STN neurons have altered oscillatory firing patterns in the theta (4-8 Hz), alpha (8-12 Hz) and beta (12-30 Hz) ranges (Levy et al., Brain. 2002; 125:1196-

1209), and exaggerated synchronization to neighboring STN units and to STN local field potentials (LFPs) in the beta range (Moran et al., Brain. 2008; 131:3395-3409). Similar to human PD, in animal models for PD significant alterations in firing patterns have been observed in STN, for example in that the percentage of neurons with a regular firing pattern decreased whereas those with irregular, mixed, or burst patterns increased (Ryu et al Neurosci Lett. 2011; Nov. 14; 505(2):113-8). Optogenic drive into STN afferent fibers with High Frequent Stimulation robustly and reversibly ameliorated PD symptoms, measured by rotational behaviors (Gradinaru et al., Science 2009; Apr. 17; 324(5925):354-9). Similarly, deep brain stimulation of STN can reverse PD symptoms in animal models (Li et al., 2012) and human patients (reviewed in Hickey and Stacy Front Neurosci. 2016; Apr. 28; 10:173).

Alpha-synuclein is a member of a family of proteins including beta- and gamma-synuclein and synoretin. Alpha-synuclein is expressed in the normal state associated with synapses and is believed to play a role in regulating synaptic vesicle release and thereby affecting neural communication, plasticity, learning and memory.

Several studies have implicated alpha-synuclein with a central role in PD pathogenesis. The protein can aggregate to form intracellular insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene as well as duplications and triplications of the gene co-segregate with rare familial forms of parkinsonism (Kruger et al., Nature Gen. (1998) 18:106-8; Polymeropoulos, et al., Science (1997) 276:2045-7).

An important finding has been that alpha-synuclein can be secreted into the extracellular fluid and be present in plasma and cerebrospinal fluid (CSF). Several studies, for example by Pacheco et al. (2015) and others (Pacheco et al J Neurochem. 2015 March; 132(6):731-4; Conway et al., Proc Natl Acad Sci USA (2000) 97:571-576; Volles et al., J. Biochem. 42:7871-7878, 2003) have suggested that extracellular-synuclein plays a pathogenic role in the brain. They demonstrated that extracellular alpha-synuclein oligomers possesses neurotoxicity toward brain neuronal plasma membranes. Another intriguing hypothesis based on the data of synuclein secretion is that a prion-like spread of alpha-synuclein underlies the progression of Parkinson's disease and other synucleinopathies (Lee et al. 2014, Nat Rev Neurol. 2014 February; 10(2):92-8; Hansen and Li 2012, Trends Mol Med. 2012 May; 18(5):248-55). These finding have given rise to a hope that extracellular-synuclein could be targeted by immunotherapy (Vekrellis et al. 2011, Lancet Neurol. 2011 November; 10(11):1015-25).

Naturally occurring alpha-synuclein auto-antibodies have been shown to be present in both PD patients and healthy controls. Sometimes no significant differences between these groups (Smith et al. 2012, PLoS One. 2012; 7(12): e52285; Maetzler et al. 2014, PLoS One. 2014 Feb. 21; 9(2):e88604, Papachroni et al. 2007 J Neurochem. 2007 May; 101(3):749-56 and Woulfe et al. 2002, Neurology. 2002 May 14; 58(9):1435-6), sometimes increased levels of auto-antibodies to alpha-synuclein in PD (Gruden et al. 2011, J Neuroimmunol. 2011 April; 233(1-2):221-7, Gruden et al. 2012, Neuroimmuno-modulation. 2012; 19(6):334-42 and Yanamandra 2011, PLoS One. 2011 Apr. 25; 6(4): e18513) or decreased auto-antibodies to alpha-synuclein in PD patients compared to healthy controls have been reported (Besong-Agbo et al 2013, Neurology. 2013 Jan. 8; 80(2):

169-75). The possibility that circulating anti-alpha-synuclein autoantibodies may serve a protective role with respect to alpha-synuclein aggregation was suggested very early on after finding of the auto-antibodies (Woulfe et al. 2002, Neurology. 2002 May 14; 58(9):1435-6).

Over expression of alpha-synuclein in transgenic mice mimics some pathological aspects of Lewy body disease. Several different transgenic lines of mice over-expressing alpha-synuclein have been generated in the last ten years (described in reviews: Koehler et al 2014, PLoS One. 2013 May 31; 8(5):e64649; Fleming and Chesselet, 2006, Behav Pharmacol. 2006 September; 17(5-6):383-91; Springer and Kahle 2006, Curr Neurol Neurosci Rep. 2006 September; 6(5):432-6). Mouse lines with Thy-1 and PDGFbeta promoters develop motor deficits and cognitive deficits and have been used to demonstrate a neuroprotective effect of antibodies directed against alpha-synuclein in vivo. However, none of the transgenic lines have robust degeneration of dopaminergic neurons, and often the motor phenotypes are driven by expression in motor neurons, which do not normally degenerate in Parkinson's disease. Therefore, it is not clear if positive outcome of a potential disease modifying treatment is mediated through effects on dopaminergic neurons or other central nervous system neurons.

One robust finding in the transgenic mouse models has been that chronic overexpression of human alpha-synuclein impairs synaptic function. Using studies in both in vitro and in vivo systems it was shown that overexpression of wild-type (wt) human alpha-synuclein impaired synaptic transmission in hippocampus (Nemani et al. 2010, Neuron. 2010 Jan. 14; 65(1):66-79; Paumier et al. 2013, PLoS One. 2013 Aug. 1; 8(8):e70274). This was shown in the CA1 region of the hippocampus where both studies found reduced basal synaptic transmission. The mechanism behind this was assumed to be intracellular accumulation of alpha-synuclein leading to dysfunctional synaptic release. However, the recent findings about secretion of alpha-synuclein into extracellular space in synapses and the toxic effects of alpha-synuclein oligomers on synapse function opens for the possibility of a role of extracellular alpha-synuclein in synaptic dysfunction, and as such for the ability of therapeutic antibodies to rescue the deficit.

The use of viral vectors to over-express alpha-synuclein represents an important way to model PD in rodents because this approach produces a relative fast progressive degeneration of nigrostriatal neurons, a feature not yet reproduced by genetic mutations in mice or rats (Kirik and Bjorklund, 2003, Trends Neurosci. 2003 July; 26(7):386-92). Furthermore, viral gene delivery revealed the ability of wt alpha-synuclein to induce nigrostriatal pathology (Kirik et al. 2002, J Neurosci. 2002 Apr. 1; 22(7):2780-91), a finding in agreement with evidence in familial forms of PD with alpha-synuclein dublications and triplications (Lee and Trojanowski, 2006, Neuron. 2006 Oct. 5; 52(1):33-8). In one study, it has been shown that goat antibodies against the N-terminus of alpha-synuclein protected against dopaminergic cell death and ameliorated behavioural deficits in a AAV-alpha-synuclein based rat model of Parkinson's disease (Shahaduzzaman et al 2015, PLoS One. 2015 Feb. 6; 10(2):e0116841).

Prion like spreading of alpha-synuclein pathology has recently been shown to develop alpha-synuclein pathology and also develop dopaminergic cell death (Luk et al. 2012, Science. 2012 Nov. 16; 338(6109):949-53). This model has been used to show that alpha-synuclein antibodies are able to ameliorate the pathology (Tran et al. 2014, Cell Rep. 2014 Jun. 26; 7(6):2054-65). In this model antibody treatment was able to reduce accumulation of phosphorylated alpha-synuclein in several brain regions—including dopaminergic neurons in substantia nigra, and reduce development of motor deficit.

In addition to mutations, alternative splicing of the alpha-synuclein gene and post-translational modifications of the protein, such as phosphorylation, ubiquitination, nitration, and truncation can create alpha-synuclein protein forms that have enhanced capacity to form aggregated and/or toxic forms of alpha-synuclein (Beyer and Ariza, Mol Neurobiol. 2013 April; 47(2):509-24). However, the precise pathological species of alpha-synuclein remains unknown. Various misfolded/aggregated/secreted species ranging from oligomers to fibrils, and different post-translational modifications have been associated with toxicity but there is no consensus on which is most important, if indeed there even is a single toxic species. Existence of altered levels of α-syn splice isoforms in patients suffering from PD, DLB and MSA have been recently reported (Cardo et al. Neurosci Lett 2014; 562(6): 45-49, and Brudek et al. J Neurochem 2016. January; 136(1):172-85). Higher aggregation potential of 112-alpha-synuclein isoform (Manda et al. PLoS One 2014 Jun. 3; 9(6)) in conjunction with and increased levels might play a role in the pathophysiology of PD or related pathologies, such as MSA.

Overall the accumulation of alpha-synuclein with similar morphological and neurological alterations in animal models as diverse as humans, mice, and flies suggests that this molecule is central in the pathogenesis of Lewy body diseases.

Several different antibodies to alpha-synuclein have been shown to have therapeutic effect in preclinical animal models. Both an antibody targeting an epitope involving alpha-synuclein residues 91-99 and antibodies targeting an epitope that involves alpha-synuclein residues 118-126 have been shown to have an effect on motor and cognitive deficits in transgenic mice (Games et al. 2014, J Neurosci. 2014 Jul. 9; 34(28):9441-54). The most advanced of these antibodies is a humanized antibody based on the mouse monoclonal antibody 9E4, which targets an epitope that involves alpha-synuclein residues 118-126, and which is now in clinical trials in phase I. A C-terminal antibody 274 which targets an epitope that involves alpha-synuclein residues 120-140 (Bae et al. 2012, J Neurosci. 2012 Sep. 26; 32(39):13454-69) was also shown to have an effect in a preclinical model on spreading of the pathology from cell to cell. In addition to these, antibodies targeting conformational species such as oligomers and fibrils of alpha-synuclein have been shown to be able to at least reduce the levels of these presumably toxic alpha-synuclein species (Lindström et al. 2014, Neurobiol Dis. 2014 September; 69:134-43 and Spencer et al. 2014, Mol Ther. 2014, October; 22(10):1753-67). These conformational antibodies that lower alpha-synuclein oligomer levels in vivo, such as mab47 were also shown to target epitopes in the C-terminus of alpha-synuclein, from amino acid 121-125 (US20120308572). Other conformational, fibril and oligomer specific antibodies also target C-terminal sequences (Vaikath et al. Neurobiol Dis. 2015; 79:81-99).

The present invention relates to a mouse antibody 2E6 (and humanised, chimeric and affinity matured versions) that binds to full length alpha-synuclein. The antibody was superior in a functional screen among 50 monoclonal antibodies against alpha-synuclein and was found to be surprisingly efficient in preventing the cellular accumulation of alpha-synuclein fibrils. It was also found to be surprisingly good in binding to pathological alpha-synuclein from human diseased brain, binding many more truncated or alternatively spliced species of alpha-synuclein than another alpha-synuclein antibody 9E4 (Masliah et al., PLoS One, 2011, Apr. 29; 6(4)—sequence published in U.S. Pat. No. 8,609,820). The antibody 2E6 can prevent alpha-synuclein aggregation in vitro and it can dissolve preformed aggregates of alpha-synuclein. The aggregated forms of alpha-synuclein can form an immune complex with the antibody and the presence of the antibody 2E6 increases the uptake of these immune-complexes via Fc-mediated phagocytosis. The antibody 2E6 binds to fibrils and blocks or neutralizes the fibrils preventing them from seeding of new alpha-synuclein aggregates in a cell model. In vivo, the antibody, after a single peripheral dose, can reverse impairments in neuronal firing in transgenic alpha-synuclein mice, and given chronically for several months, the antibody reduces the effect of alpha-synuclein overexpression on impaired vesicular release. This effect may translate to improved synaptic transmission in human PD patients treated with this antibody.

Finally, we show in a rat alpha-synuclein Parkinson's model, after chronic treatment for two months, that the antibody 2E6 can reverse pathological irregular firing of neurons in STN. As STN pathological activity has a primary role in PD symptoms, reversing pathological changes in the cortico-subthalamic pathway is important for amelioration of motor deficits.

The parent mouse antibody has been humanized and affinity matured to generate a therapeutic antibody for the treatment of alpha-synucleinopathies. The humanized antibody as well as affinity matured forms retains the same binding and cell based functions as the parent antibody.

SUMMARY OF THE INVENTION

The present invention relates to a mouse antibody denoted m2E6, chimeric ch2E6, as well as to 3 humanized forms (2E6-HLD1, 2E6-HLD2 and 2E6-HLD3) and affinity matured forms of HLD1: 7A10, 5A1, 9D7, 9G11, 7C4, L3, 8D9, 9C12 or 6B6 to create higher affinity antibodies.

The invention also relates to monoclonal antibodies able to compete with said antibodies and in particular 2E6 and HLD-1 disclosed herein, for the binding to an epitope on alpha-synuclein.

The specific monoclonal antibodies are disclosed herein.

B) Western Blot of SHSY-5Y cells treated with alpha-synuclein fibrils and antibodies for 24 hours, then washed and lysed. This showed that 2E6-HLD1 reduced the amount of fibrils accumulated in the cells, whereas the B12 antibody did not.

C) Automated fluorescent imaging of accumulation of alpha-synuclein fibrils in SKmel5-cells, co-incubation for 24 hr with fibrils, m2E6 and alpha-synuclein peptides as indicated. This showed that m2E6 reduce the accumulation of fibrils in the cells. This effect is specific as it could be inhibited by the peptide 126-140 covering the epitope of m2E6, but not by a peptide outside the epitope (amino acid 113-120).

D) Accumulation of alpha-synuclein fibrils in SKmel5-cells, 24 hours, dose-response of an affinity maturated 2E6-HLD1 antibody, 2E6_7A10 from 0.1 to 10 μg/ml. Thus, 2E6_7A10 binds to the alpha-synuclein fibrils in solution and reduce their accumulation in the cells in a dose-dependent manner.

Asterisks (***) indicate a p-value lower than 0.0001 in a two-tailed t-test when compared to fibrils only (Example 6).

Figure 8:
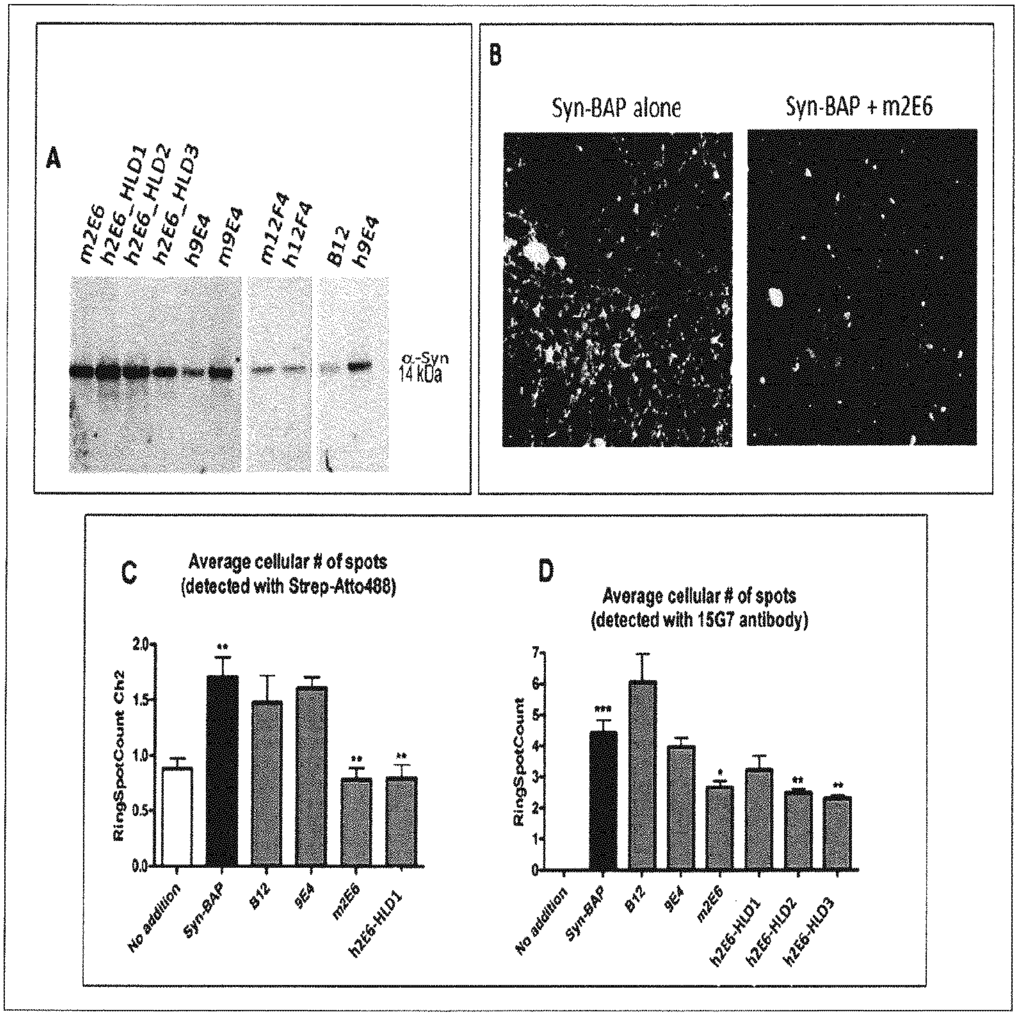

FIG. 8 shows that m2E6 binds fibrillized, mammalian produced alpha-synuclein in media and inhibits its accumulation in primary cortical neurons.

A) shows that all of the 2E6-variants pulled down the alpha-synuclein oligomers from the media, both full-length and some truncated versions (weaker low molecular weight bands). The comparator antibody m9E4 did also pull down the full-length alpha-synuclein, however the humanized version of 9E4 (US patent 20080175838) was much less efficient in immunoprecipitation of both truncated forms and the 14 kDa full length form of alpha-synuclein, indicating less binding to the mammalian protein in media.

Another comparator antibody (12F4 from Biogen, U.S. Pat. No. 8,940,276) gave only a weak band that was not much different from B12 control.

B) shows that incubation with m2E6 antibody leads to reduced accumulation of intracellular alpha-synuclein aggregates in primary cortical neurons.

C) and D) shows (in two readouts from the same experiment) that co-incubation of the Syn-BAP PFFs (preformed fibrils=PFFs—the mammalian alpha-synuclein is made into fibrils, which are sonicated to produce PFFs—precursors or seeds to full fibrils) with either non-reactive B12 or the comparator 9E4 antibody did not change the accumulation of Syn-BAP PFFs in the cells, whereas treatment with m2E6 or 2E6-HLD1 reduced the level of accumulation to background level. Cells treated with Syn-BAP PFFs alone showed around 4.5 spots per cell (FIG. 8D); again B12 or h9E4 did not change this significantly. Treatment with m2E6, h2E6-HLD2 or h2E6-HLD3 reduced the level of accumulation significantly (to around 3 spots per cell) and 2E6-HLD1 showed a trend towards a lower number of spots (Example 6).

Figure 9:
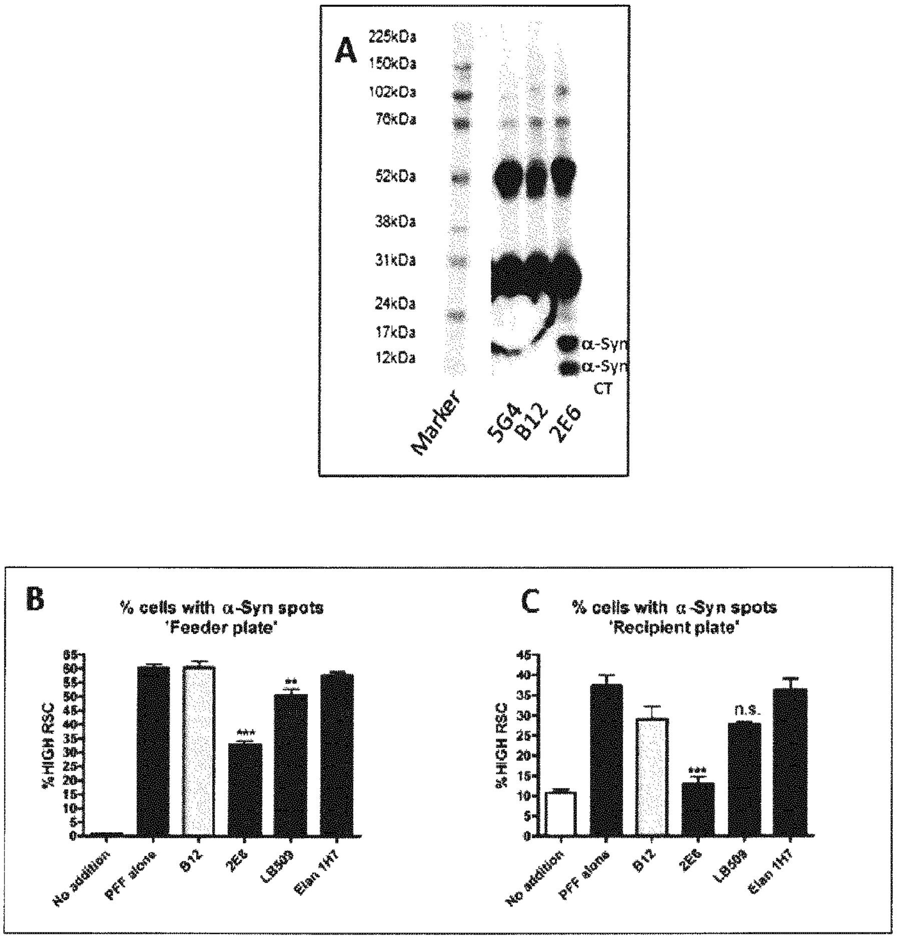

FIG. 9 shows that 2E6 binds to alpha-synuclein fibrils in conditioned media and inhibits transfer from cell-to-cell.

A) Immunoprecipitation of conditioned media from SK-mel5 cells treated with alpha-synuclein fibrils for 24 hours. The media was harvested and used for IP (immunoprecipitation). 2E6 efficiently IP'ed alpha-synuclein.

B) After addition of alpha-synuclein fibrils to the media the percentage of cells that accumulated intracellular alpha-synuclein fibrils was quantified on the 'feeder' plate" as % cells containing alpha-synuclein spots, C) the media from the Feeder cells were transferred to the recipient plate and against the percentage of cells with intracellular alpha-synuclein fibrils were quantified on the 'recipient' plate. B) and C) shows that m2E6 significantly reduces the number of cells with alpha-synuclein aggregates (spots) in both the 'feeder' and the 'recipient' plate. The comparator antibody 1H7 (WO2005047860) had no effect on either plate. A control antibody (B12) did likewise have no effect. (Example 6).

Figure 10:
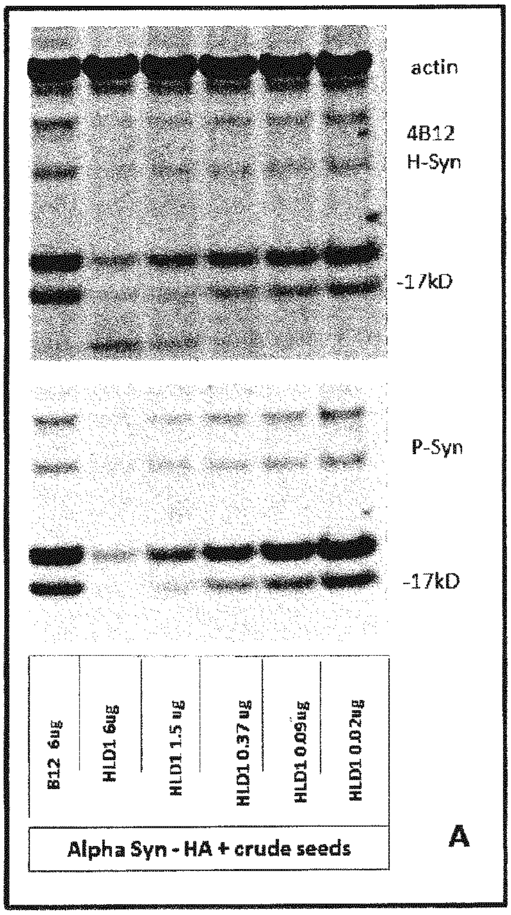
Figure 10:
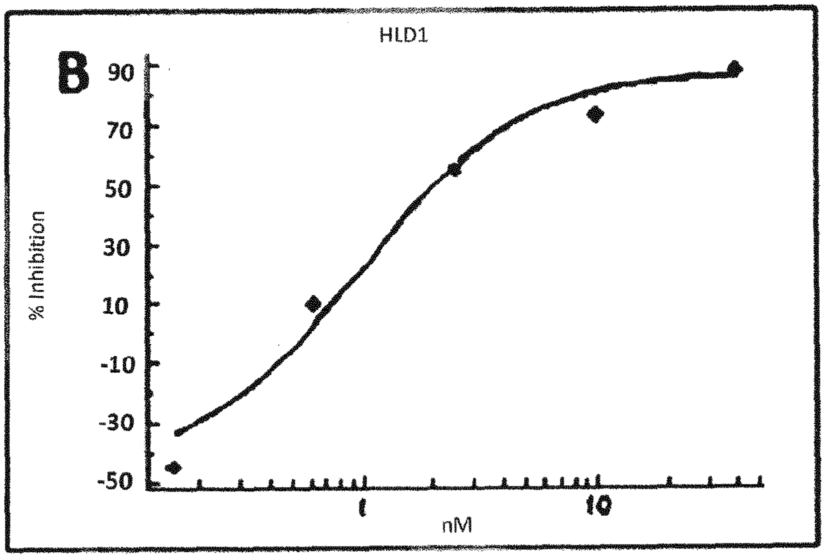

FIG. 10 shows that 2E6-HLD1 dose-dependently inhibit seeding of endogenous alpha-synuclein. HEK293 cells were transfected with an alpha synuclein expressing plasmid with a HA tag, followed by transfection of alpha synuclein fibrils and addition of various concentrations of 2E6-HLD1. After 48 hours cellular lysates were fractionated by ultracentrifugation into Triton and SDS soluble fractions and analysed by immunoblot. Alpha synuclein with HA tag runs higher than 17 KD. The ratio of phospho-synuclein and beta-actin was used for quantification of insoluble alpha-synuclein (SDS soluble fraction).

A. Western Blot of SDS soluble fraction from HEK293 cells. The top image shows an immunoblot using antibody 4B12, that detects human alpha synuclein, and antibody for beta-actin. Bottom image shows immunoblot using antibody Ab51253, that detects phospho-synuclein. Treatment with 2E6-HLD1 shows a dose dependent inhibition of alpha-synuclein aggregation and phosphorylation compared to the control antibody, B12.

B. Quantification of the westenblot on phospho-synuclein from FIG. 10A. 2E6-HLD1 inhibited the conversion of soluble alpha-synuclein into the insoluble fraction in a dose dependent manner (example 6).

Figure 11:
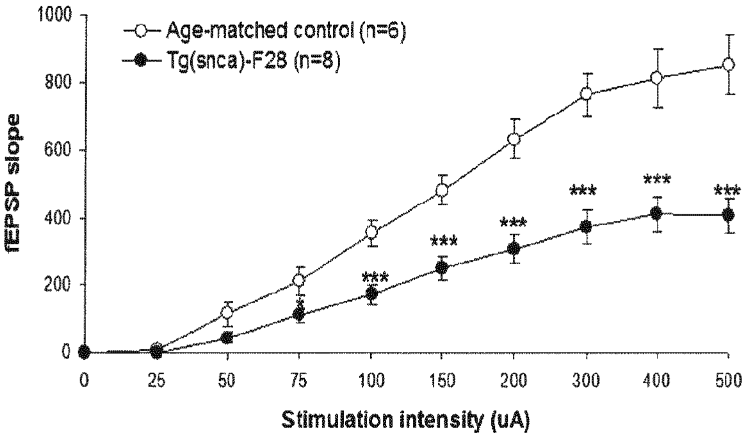
Figure 11:
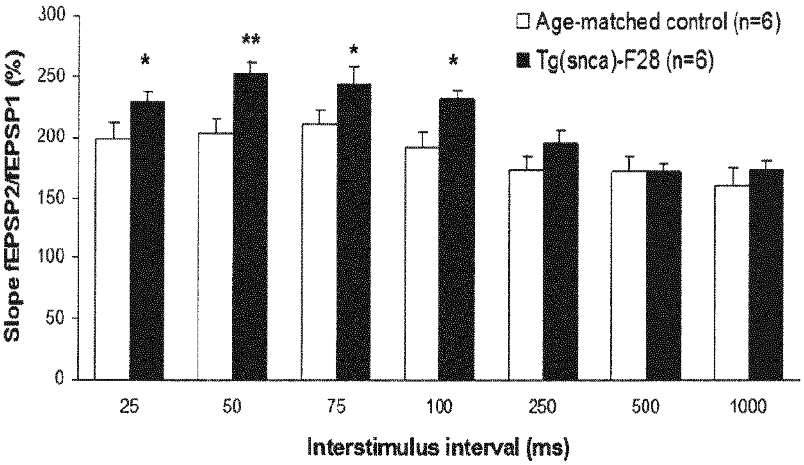

FIG. 11 shows impairments in basal synaptic transmission and paired-pulse facilitation at the Schaffer collateral-CA1 synapse in the hippocampus of F28-snca transgenic and age-matched control mice. Field excitatory post-synaptic potentials (fEPSPs) were evoked by a single stimulus applied to the Schaffer collateral, and basal synaptic transmission was assessed by measuring the fEPSP slope as a function of the stimulation intensity (a). Short-term synaptic plasticity was evaluated by induction of paired-pulse facilitation (b) where a double stimulus with varying inter-stimulus interval was applied, and the ratio between the slope of the second fEPSP and the first fEPSP was measured. All data were analyzed by a two-way ANOVA with repeated measurements followed by Bonferoni t-test (* $p<0.05$;  $p<0.01$; * $p<0.001$) (Example 7).

Figure 12:
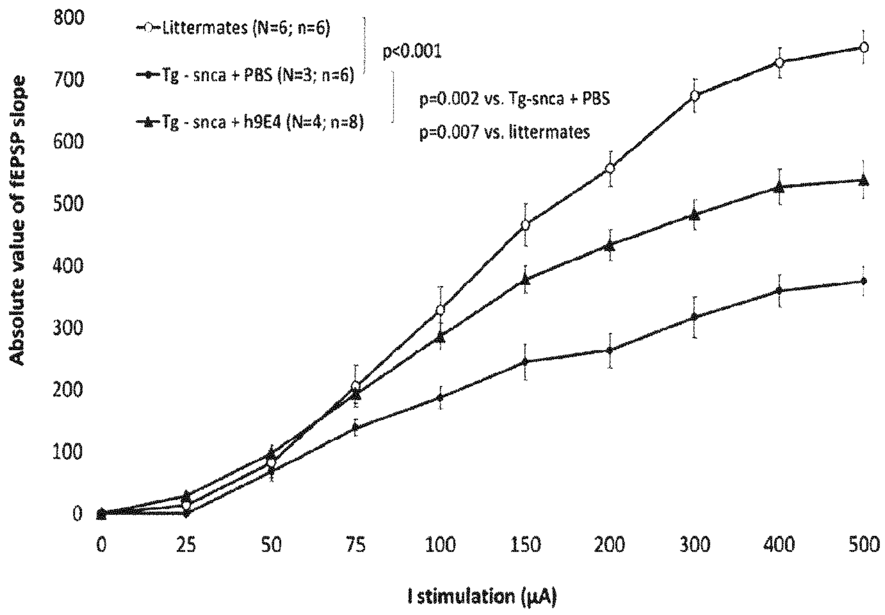
Figure 13:
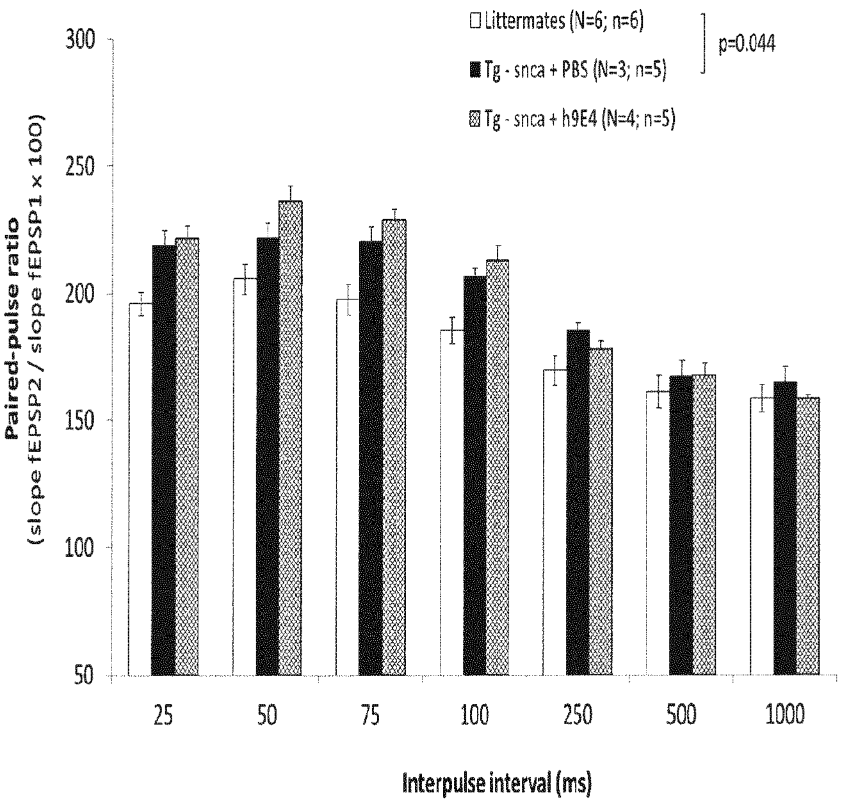

FIGS. 12 and 13 show acute effect of 9E4 (15 mg/kg i.p.) on the impairments in basal synaptic transmission and paired-pulse facilitation at the Schaffer collateral-CA1 synapse in the hippocampus of F28-snca transgenic mice.

In FIG. 12 field excitatory post-synaptic potentials (fEPSPs) were evoked by a single stimulus applied to the Schaffer collateral, and basal synaptic transmission was assessed by measuring the fEPSP slope as a function of the stimulation intensity. 9E4 was able to partially reverse the deficit In FIG. 13 short-term synaptic plasticity was evaluated by induction of paired-pulse facilitation where a double stimulus with varying inter-stimulus interval was applied, and the ratio between the slope of the second fEPSP and the first fEPSP was measured. 9E4 was not able to reverse the deficit.

All data were analyzed by a two-way ANOVA with repeated measurements followed by Bonferoni t-test (Example 7).

Figure 14:
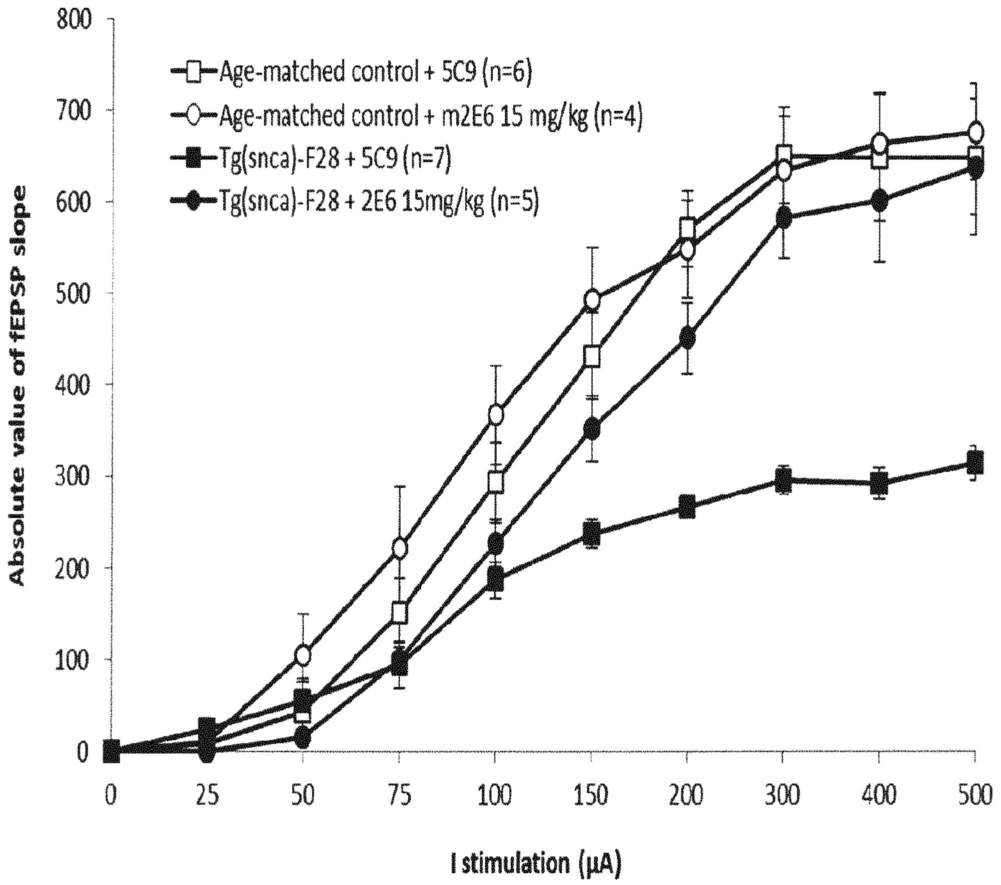

FIG. 14 shows acute beneficial effect of m2E6 (15 mg/kg i.p.) on the impairments in basal synaptic transmission at the Schaffer collateral-CA1 synapse in the hippocampus of F28-snca transgenic mice.

In FIG. 14 field excitatory post-synaptic potentials (fEPSPs) were evoked by a single stimulus applied to the Schaffer collateral, and basal synaptic transmission was assessed by measuring the fEPSP slope as a function of the stimulation intensity. m2E6 was able to fully reverse the deficits.

Figure 15:
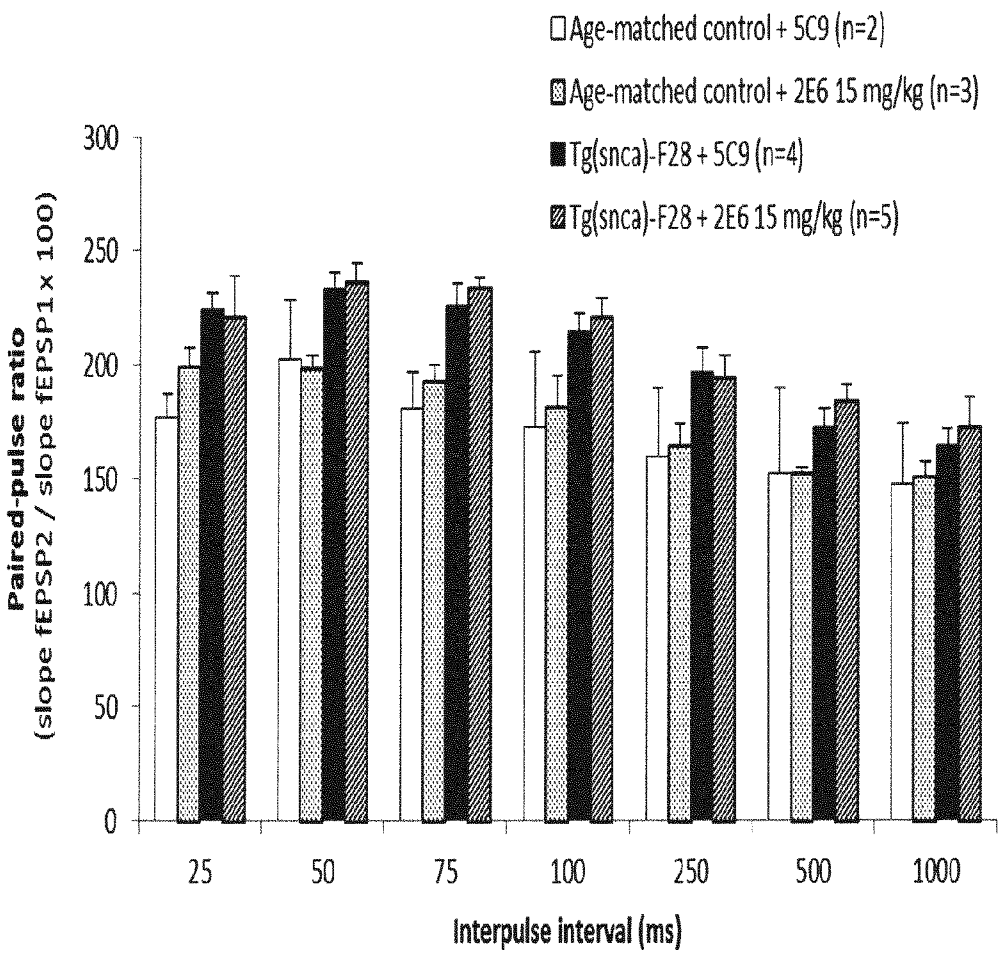

In FIG. 15 short-term synaptic plasticity was evaluated by induction of paired-pulse facilitation where a double stimulus with varying inter-stimulus interval was applied, and the ratio between the slope of the second fEPSP and the first fEPSP was measured. m2E6 had no acute effect on the impaired PPF in F28-snca transgenic mice (however an effect after chronic treatment was observed).

All data were analyzed by a two-way ANOVA with repeated measurements followed by Bonferoni t-test (Example 7).

Figure 16:
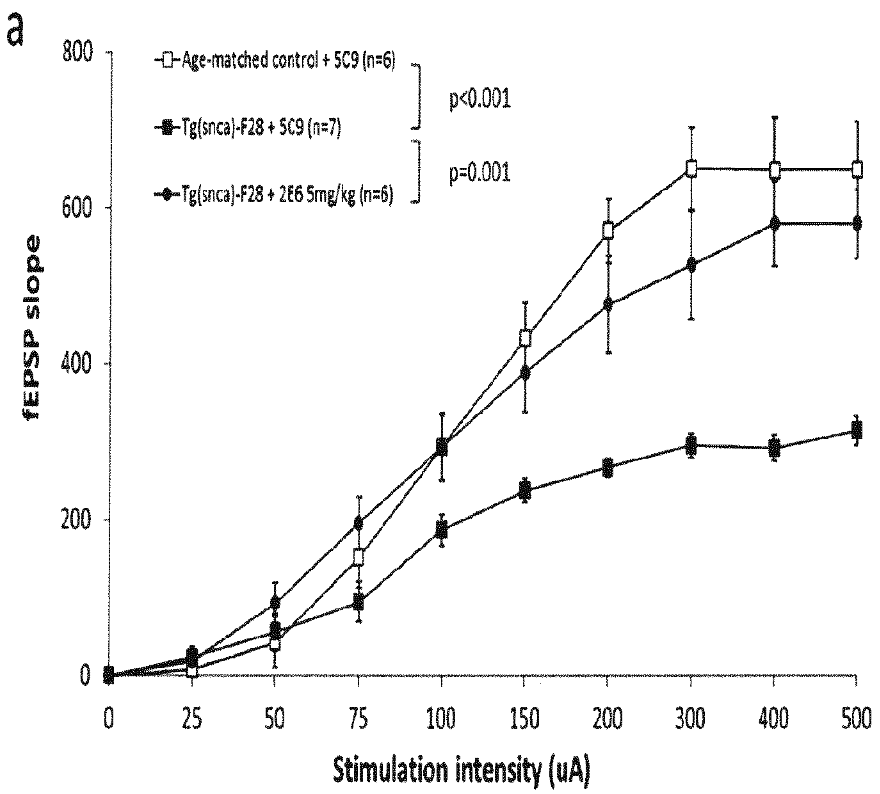
Figure 17:
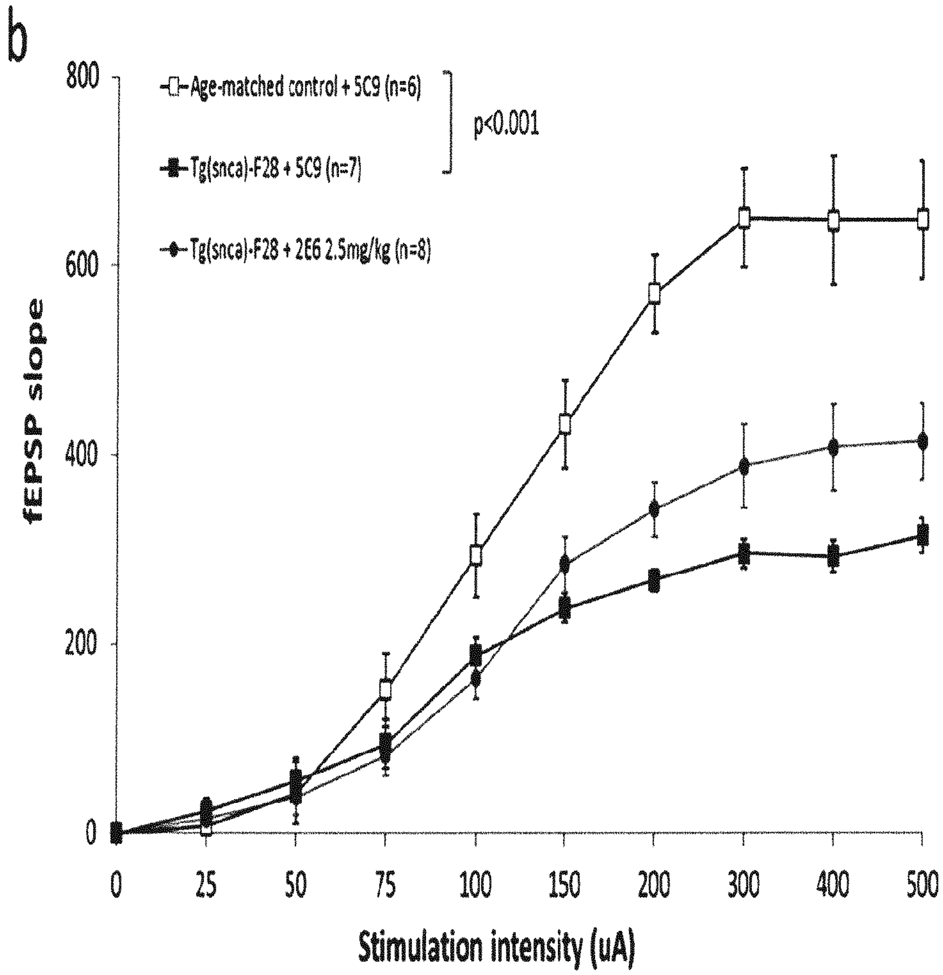

FIGS. 16 and 17 show an acute dose dependent effect of m2E6 in reversing impairment in basal synaptic transmission. The effect of m2E6 at 5 (FIG. 16) and 2.5 (FIG. 17) mg/kg i.p. on the impairments in basal synaptic transmission at the Schaffer collateral-CA1 synapse in the hippocampus of F28-snca transgenic mice. The data show a dose-dependent effect of m2E6 on reversing the deficit.

Field excitatory post-synaptic potentials (fEPSPs) were evoked by a single stimulus applied to the Schaffer collateral, and basal synaptic transmission was assessed by measuring the fEPSP slope as a function of the stimulation intensity.

All data were analyzed by a two-way ANOVA with repeated measurements followed by Bonferoni t-test (Example 7).

Figure 18:
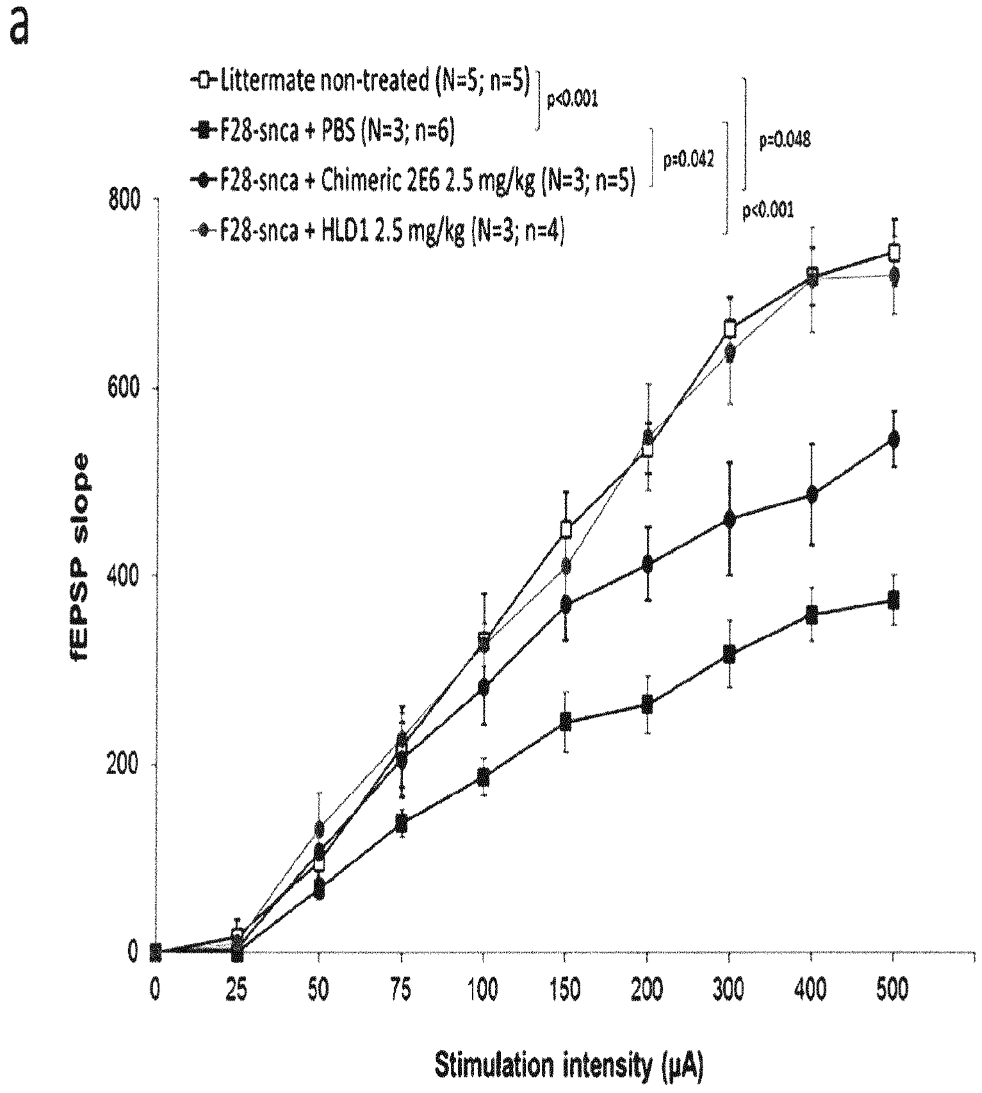

FIG. 18 shows an increased efficacy at low doses of the humanized 2E6; 2E6-HLD1 compared to chimeric, ch2E6 (m2E6 variable domain) in reversing the impairment in basal synaptic transmission.

Acute effect of ch2E6 and 2E6-HLD1, both at 2.5 mg/kg i.p. on the impairments in basal synaptic transmission and paired-pulse facilitation at the Schaffer collateral-CA1 synapse in the hippocampus of F28-snca transgenic mice. Field excitatory post-synaptic potentials (fEPSPs) were evoked by a single stimulus applied to the Schaffer collateral, and basal synaptic transmission was assessed by measuring the fEPSP slope as a function of the stimulation intensity. ch2E6 showed a strong trend towards reversing the impairment whereas same low dose of the humanised form 2E6-HLD1 completely reversed the impairment.

Figure 19:
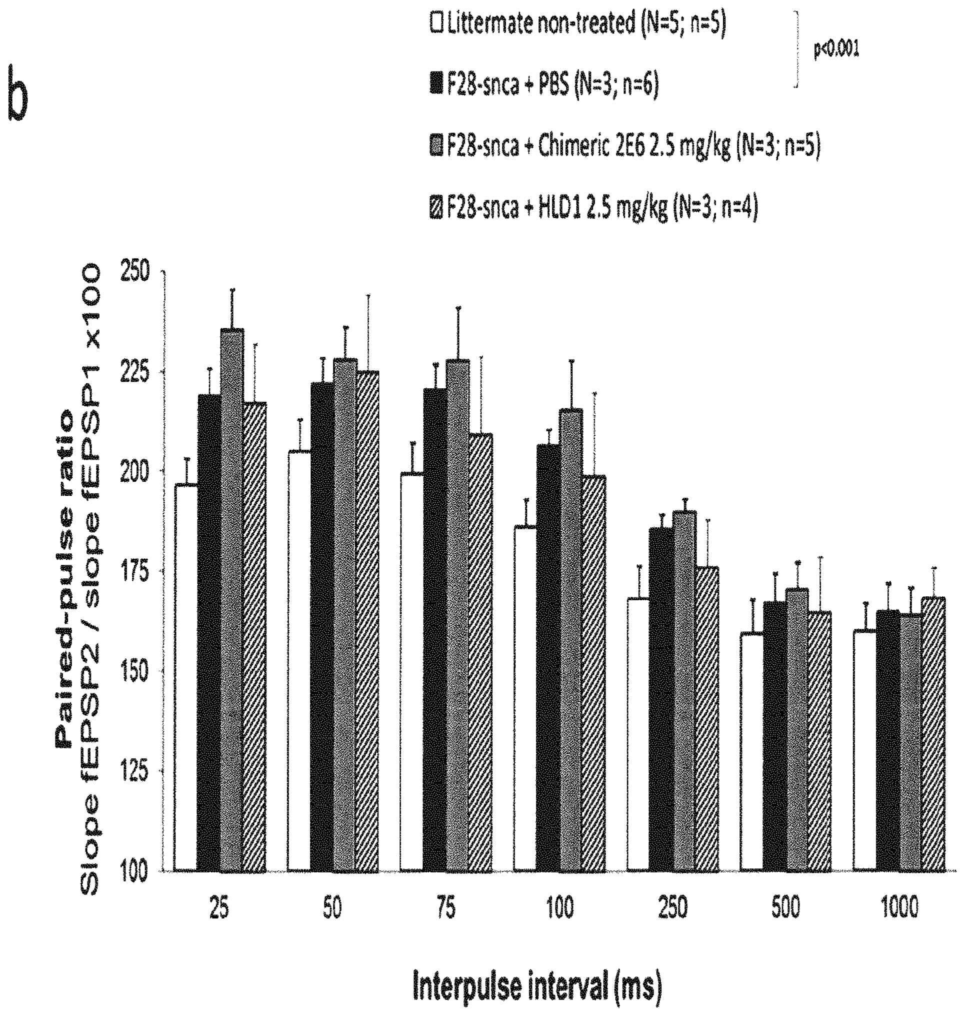

In FIG. 19 short-term synaptic plasticity was evaluated by induction of paired-pulse facilitation where a double stimulus with varying inter-stimulus interval was applied, and the ratio between the slope of the second fEPSP and the first fEPSP was measured. As observed with m2E6, chimeric 2E6 did not have any significant effect on the impaired PPF in F28-snca transgenic mice All data were analyzed by a two-way ANOVA with repeated measurements followed by Bonferoni t-test (Example 7).

Figure 20:
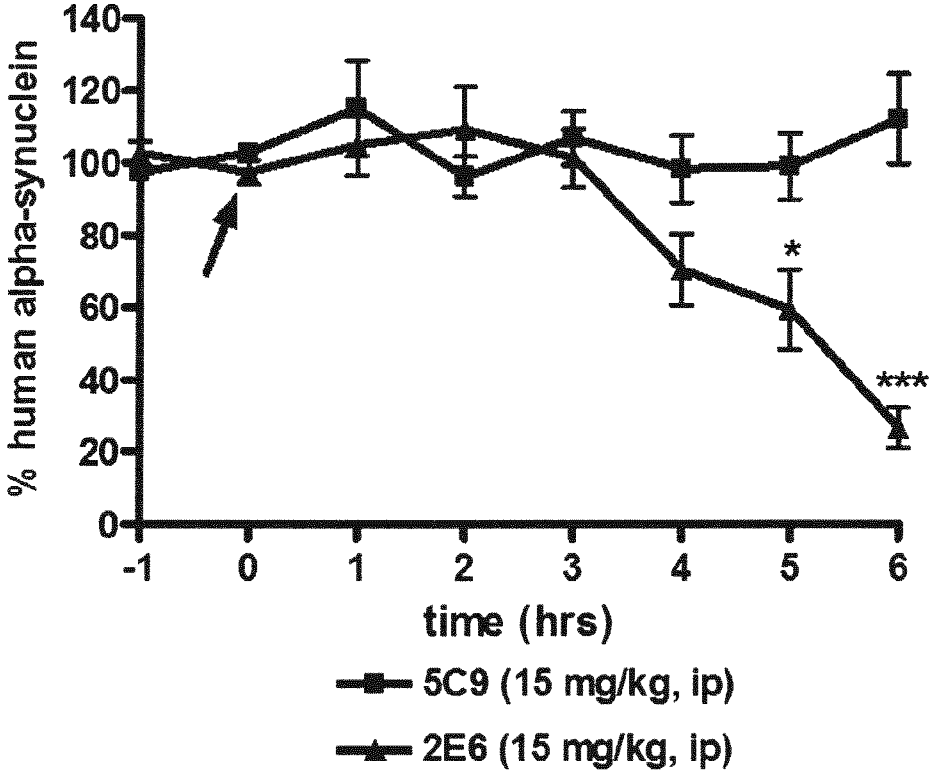
Figure 21:
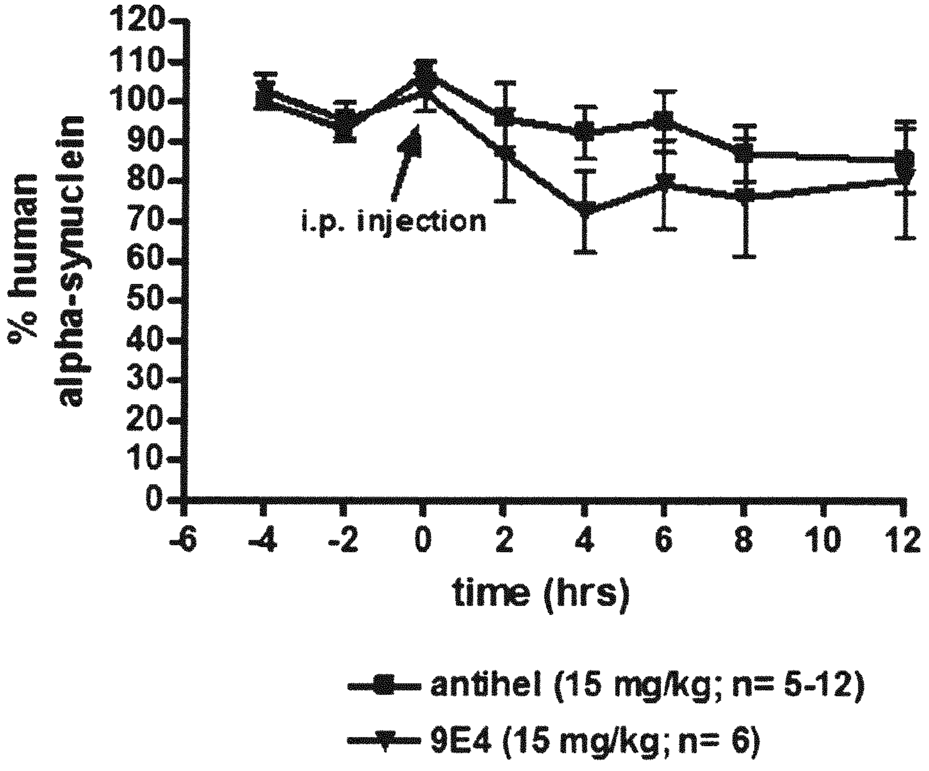

FIGS. 20 and 21 show that m2E6 reduce extracellular levels of alpha-synuclein in freely moving mice whereas 9E4 does not.

FIG. 20 shows effect of systemic administration of 2E6 or control isotype 5C9 (15 mg/kg, i.p.) on the levels of human α-synuclein in the hippocampus of freely moving F28 snca transgenic mice. Basal human α-synuclein was taken as the average of human a-synuclein concentration in two consecutive samples (11.9±2.4 ng/ml) and it was set to 100% within the same animal. *p<0.05, ***p<0.001; 2E6 versus control isotype antibody 5C9

FIG. 21 shows effect of systemic administration of h9E4 or control isotype anti-hel (both 15 mg/kg, i.p.) on the extracellular levels of human α-synuclein in the hippocampus of freely moving F28 snca transgenic mice. Basal human α-synuclein was taken as the average of human α-synuclein concentration in 2-3 consecutive samples (7.8±1.2 ng/ml) and it was set to 100% within the same animal. (Example 8).

Figure 22:
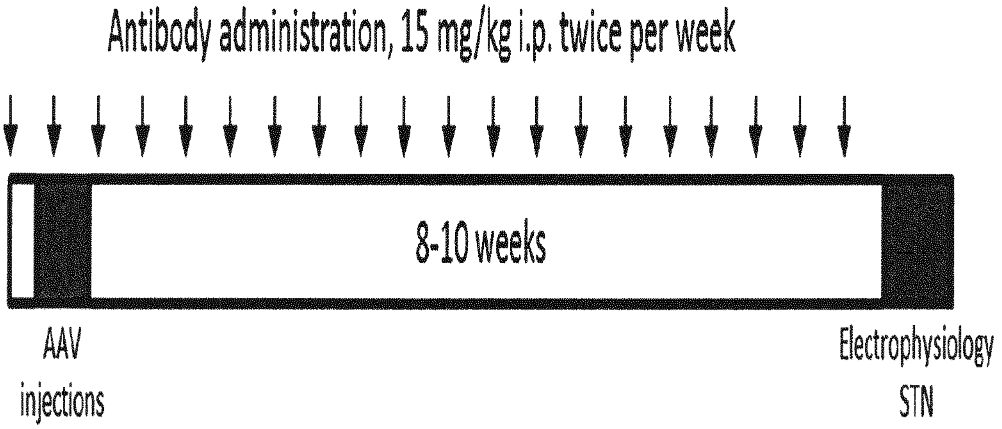

FIG. 22 shows a schematic representation of the timeline for antibody treatment in the rat alpha-synuclein AAV model, viral injections and electrophysiological measurements (Example 9).

Figure 23:
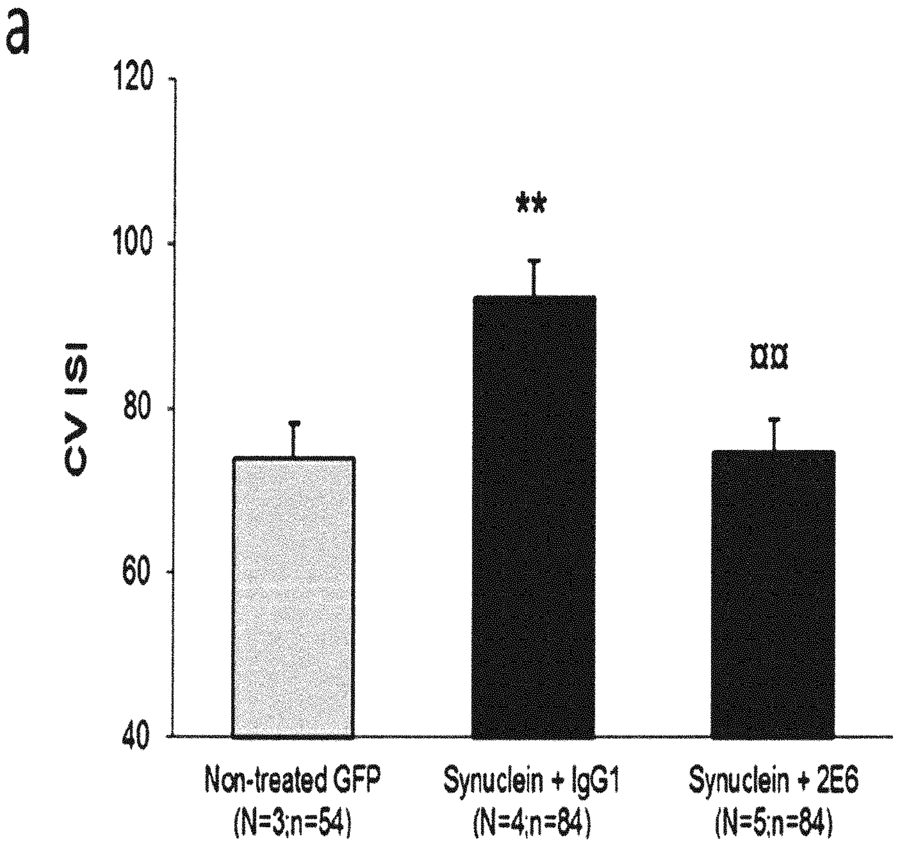
Figure 24:
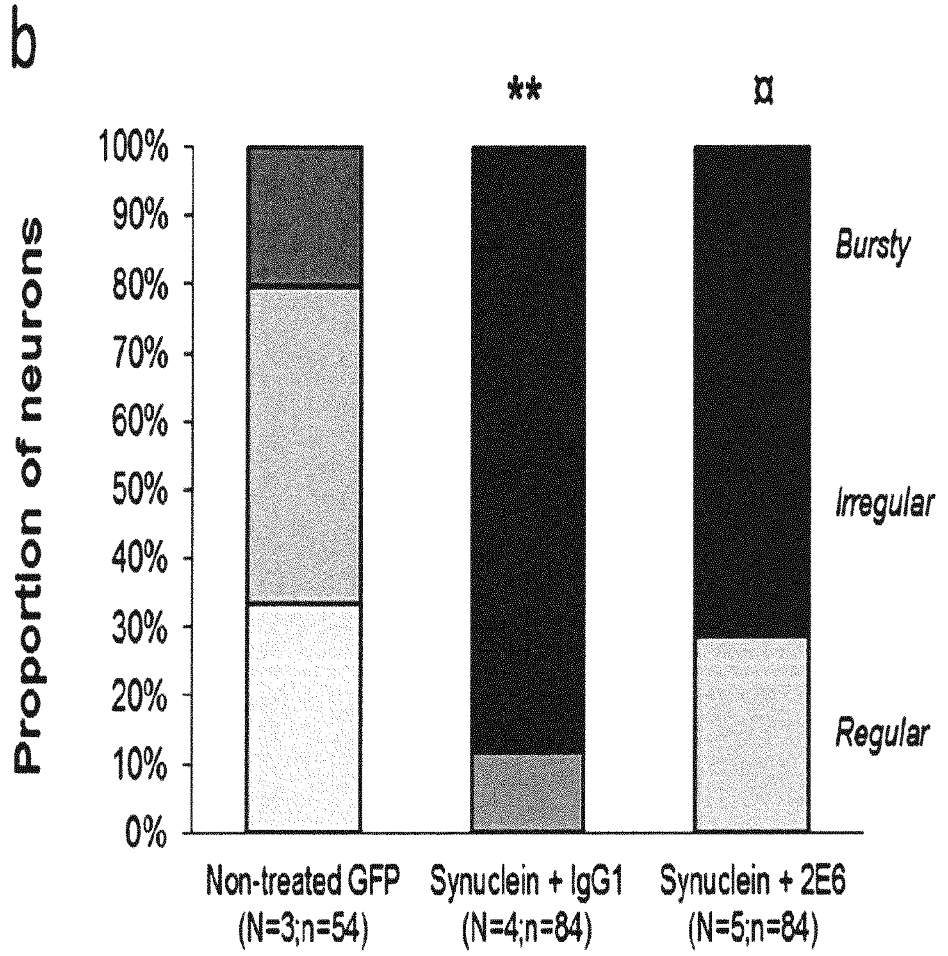

FIGS. 23 and 24 show that the pattern of neuronal activity in one brain area, the Subthalamic Nucleus, is changed in rats where human alpha-synuclein is overexpressed. Treatment with m2E6 normalises the abnormal neuronal firing pattern.

The firing pattern of STN neurons in non-treated GFP overexpressing rats or α-synuclein overexpressing rats treated either with a control mlgG1 or m2E6 (15 mg/kg i.p., twice a week) for 8-10 weeks post-virus injection. In FIG. 23 the coefficient of variation (CV) of the interspike interval was analyzed by a one-way ANOVA followed by Bonferroni post-hoc test. Treatment with m2E6 resulted in a non-significant trend for a decrease in their CV ISI.

In FIG. 24 the proportion of neurons firing in a regular, irregular or bursty firing pattern was analyzed by a Chi-square test. Treatment with m2E6 induced a significant normalisation of the proportion of neurons exhibiting the 3 distinct firing patterns.

N: number of animals; n: number of neurons., PBS-treated α-synuclein rats were compared to non-treated GFP rats,  p<0.01. ¤¤ m2E6 was compared to mlgG1 in α-synuclein overexpressing rats, ¤ p<0.05, ¤¤ p<0.01 (Example 9).

Figure 25:
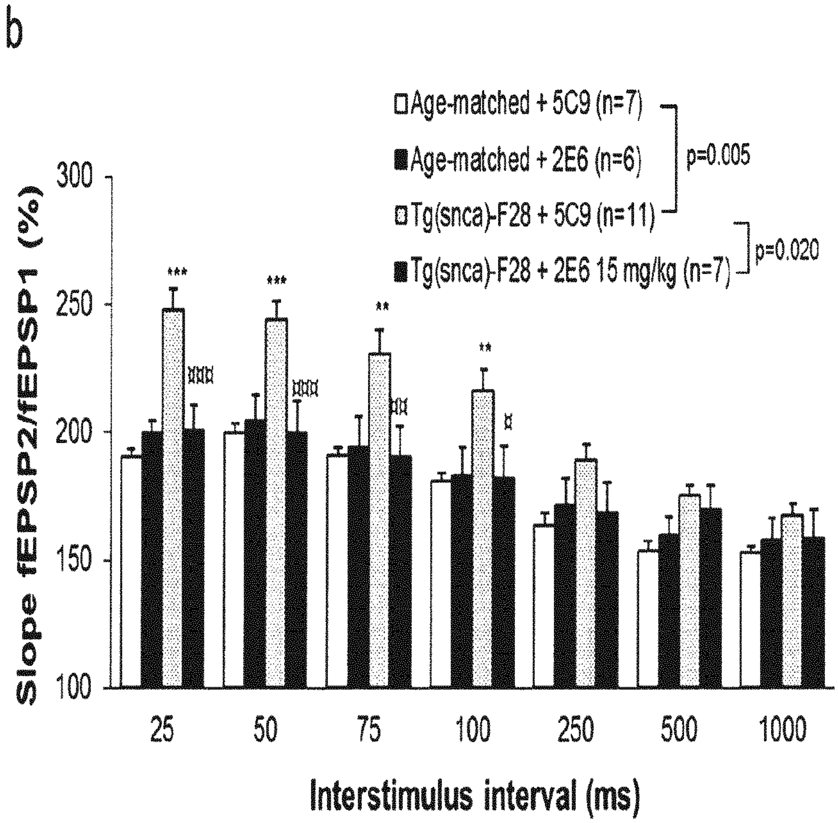

FIG. 25 shows a beneficial effect of m2E6 after chronic treatment (15 mg/kg i.p. in 16-18 weeks) on paired-pulse facilitation at the Schaffer collateral-CA1 synapse in the hippocampus of F28-snca transgenic mice.

Chronic treatment with m2E6 or a control mlgG1 (5C9) on paired-pulse facilitation at the Schaffer collateral-CA1 synapse in the hippocampus of F28-snca transgenic and age-matched control mice. Field excitatory post-synaptic potentials (fEPSPs) were evoked by a single stimulus applied to the Schaffer collateral, and basal synaptic transmission was assessed by measuring the fEPSP slope as a function of the stimulation intensity. Short-term synaptic plasticity was evaluated by induction of paired-pulse facilitation (PPF) where a double stimulus with varying inter-stimulus interval was applied, and the ratio between the slope of the second fEPSP and the first fEPSP was measured. All data were analyzed by a two-way ANOVA with repeated measurements followed by Bonferoni t-test (* p<0.05;  p<0.01; * p<0.001 for Tg-snca+5C9 vs Agedmatched+5C9; ¤ p<0.05, ¤¤ p<0.01, ¤¤¤ p<0.001 for Tg-snca+m2E6 vs Tg-snca+5C9). (Example 9).

DETAILED DESCRIPTION OF THE INVENTION

Definitions

As used herein, the term "alpha-synuclein" is synonym with the alpha-synuclein protein and refers to any of the alpha-synuclein protein isoforms (identified in for example UniProt as P37840, 1-3). The amino acid numbering of alpha-synuclein is given with respect to SEQ ID NO: 1 as shown below, with methionine (M) being amino acid residue 1:

```
SEQ ID NO: 1:
MDVFMKGLSKAKEGVVAAAEKTKQGVAEAAGKTKEGVLYVGSKTKEG

VVHGVATVAEKTKEQVTNVGGAVVTGVTAVAQKTVEGAGSIAAATGF

VKKDQLGKNEEGAPQEGILEDMPVDPDNEAYEMPSEEGYQDYEPEA
```

The present invention relates to antibodies and to fragments of antibodies that are capable of specifically binding to alpha-synuclein, and in particular to human alpha-synuclein. In particular, the antibodies and fragment thereof exhibit the ability to specifically bind to the 126-140 epitope of human alpha-synuclein, SEQ ID NO:2.

The term "antibody" (Ab) in the context of the present invention refers to an immunoglobulin molecule or according to some embodiments of the invention may be a fragment of an immunoglobulin molecule which has the ability to specifically bind to an epitope of a molecule ("antigen"). Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 and CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chains include kappa chains and lambda chains. The heavy and light chain variable region is typically responsible for antigen recognition, while the heavy and light chain constant region may mediate the binding of the immunoglobulin to host tissues or factors, including various cells of the immune system (e.g., effector cells) and the first component (C1q) of the classical complement system. The VH and VL regions can be further subdivided into regions of hypervariability, termed "complementarity determining regions," that are interspersed with regions of more conserved sequence, termed "framework regions" (FR). Each VH and VL is composed of three CDR (complementarity determining region) Domains and four FR Domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their antigen-binding fragments that have been "isolated" so as to exist in a physical milieu distinct from that in which it may occur in nature or that have been modified so as to differ from a naturally occurring antibody in amino acid sequence.

As used herein, the term "antigen-binding fragment of an antibody" means a fragment of an antibody capable of specifically binding to an epitope. An antigen-binding fragment may contain 1, 2, 3, 4, 5 or all 6 of the CDR Domains of such antibody and, although capable of specifically binding to such epitope, may exhibit a specificity, affinity or selectivity toward such epitope that differs from that of such antibody. Preferably, however, an antigen-binding fragment will contain all 6 of the CDR Domains of such antibody. An antigen-binding fragment of an antibody may be a single polypeptide chain (e.g., an scFv), or may comprise two or more polypeptide chains, each having an amino-terminus and a carboxyl terminus (e.g., a diabody, a Fab fragment, a $Fab_2$ fragment, etc.). Fragments of antibodies that exhibit antigen-binding ability can be obtained, for example, by protease cleavage of intact antibodies. More preferably, although the two domains of the Fv fragment, VL and VH, are encoded by separate genes, such gene sequences or their encoding cDNA can be joined, using recombinant methods, by a flexible linker that enables them to be made as a single protein chain in which the VL and VH regions associate to form monovalent antigen-binding molecules (known as single-chain Fv (scFv); see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH regions of a single polypeptide chain to associate together, one can form a bispecific antibody, diabody, or similar molecule (in which two such polypeptide chains associate together to form a bivalent antigen-binding molecule) (see for instance PNAS USA 90(14), 6444-8 (1993) for a description of diabodies). Examples of the antigen-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge region; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i(II):484-90); (vi) camelid or nanobodies (Revets et al; Expert Opin Biol Ther. 2005 January; 5_(I): I II-24) and (vii) an isolated CDR. Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant region genes. Such antibody fragments are obtained using conventional techniques known to those of skill in the art; suitable fragments capable of binding to a desired epitope may be readily screened for utility in the same manner as an intact antibody.

The term "bispecific antibody" refers to an antibody containing two independent binding domains that each target independent targets. These targets can be different proteins or different epitopes on the same target. Bispecific antibody molecules can be made using compensatory amino acid changes in the constant regions of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time (Ridgway et al., Protein Engineering 9, 617-621 (1996), Gunasekaran et al., JBC 285, 19637-19641(2010), Moore et al., MAbs 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAbs 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities. For example, targeting both a therapeutic target and a transcytosing surface receptor for the purpose of delivering a therapeutic antibody across the blood brain barrier to treat a CNS disease.

The term "humanized antibody" as used herein, is intended to refer to forms of non-human (e.g. murine) antibodies that are specifically chimeric immunoglobulins, immunoglobulin chains, or fragments thereof (such as Fv, Fab, Fab', F(ab')2 or other antigen binding subsequences of antibodies) that contain minimal sequence derived from non-human immuno-globulin. For the most part, humanized antibodies are human immunoglobulins (recipient antibody) in which residues from a CDR of the recipient are replaced by the residues from a CDR of a non-human species (donor antibody) such as mouse, rabbit, or rat having the desired specificity, affinity and capacity. In some instances, Fv framework (FR) residues of the human immunoglobulin are replaced by corresponding non-human residues. Furthermore, the humanized antibody will comprise residues that are found neither in the recipient nor in the imported CDR or framework sequences, but are included to further refine and optimize antibody performance. In general, the humanized anti-body will comprise substantially all of at least one, and typically two, variable domains, in which substantially all of the FR regions are those of a human consensus sequence. The humanized antibody optimally also will comprise at least a portion of an immunoglobulin constant region or domain (Fc), typically that of a human immunoglobulin. Antibodies may have modified Fc regions known to those skilled in the art. Other forms of humanized antibodies have one or more CDRs (one, two, three four, five, six) which are altered with respect to the original antibody, which are also termed one or more CDRs "derived from" one or more CDRs from the original antibody.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments a monoclonal antibody can be composed of more than one Fab domain thereby increasing the specificity to more than one target.

The antibody "mouse 2E6 or "m2E6" is intended to mean an antibody consisting of the Light Chain SEQ ID NO 19 and Heavy Chain SEQ ID NO 20.

The antibody ""chimeric 2E6 or "ch2E6" is intended to mean an antibody consisting of the Light Chain SEQ ID NO 21 and Heavy Chain SEQ ID NO 22.

The antibody "'2E6-HLD-1" or "h2E6-HLD-1" or "H2E6-HLD-1" or "2E6-HLD1" is intended to mean an antibody consisting of the Light Chain SEQ ID NO 23 and Heavy Chain SEQ ID NO 24.

The antibody "'2E6-HLD-2" or "h2E6-HLD-2" or H2E6-HLD-2" or "2E6-HLD2" is intended to mean an antibody consisting of the Light Chain SEQ ID NO 25 and Heavy Chain SEQ ID NO 26.

The antibody "'2E6-HLD-3" or "h2E6-HLD-3" or H2E6-HLD-3" or "2E6-HLD3" is intended to mean an antibody consisting of the Light Chain SEQ ID NO 27 and Heavy Chain SEQ ID NO 28.

The antibody "'6B6" is intended to mean an antibody consisting of the Light Chain SEQ ID NO 45 and Heavy Chain SEQ ID NO 46.

The antibody "5A1" is intended to mean an antibody consisting of the Light Chain SEQ ID NO 29 and Heavy Chain SEQ ID NO 30.

The antibody "9D7" is intended to mean an antibody consisting of the Light Chain SEQ ID NO 31 and Heavy Chain SEQ ID NO 32.

The antibody "9G11" is intended to mean an antibody consisting of the Light Chain SEQ ID NO 33 and Heavy Chain SEQ ID NO 34.

The antibody "L3" or "L3-11" (used interchangeably herein) is intended to mean an antibody consisting of the Light Chain SEQ ID NO 37 and Heavy Chain SEQ ID NO 38.

The antibody "7A10" is intended to mean an antibody consisting of the Light Chain SEQ ID NO 39 and Heavy Chain SEQ ID NO 40.

The antibody "8D9" is intended to mean an antibody consisting of the Light Chain SEQ ID NO 41 and Heavy Chain SEQ ID NO 42.

The antibody "9C12" is intended to mean an antibody consisting of the Light Chain SEQ ID NO 43 and Heavy Chain SEQ ID NO 44.

The antibody "6B6" is intended to mean an antibody consisting of the Light Chain SEQ ID NO 45 and Heavy Chain SEQ ID NO 46.

The antibody "7C4" is intended to mean an antibody consisting of the Light Chain SEQ ID NO 35 and Heavy Chain SEQ ID NO 36.

Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

As used herein, an antibody or an antigen-binding fragment thereof is said to "specifically" bind a region of another molecule (i.e., an epitope) if it reacts or associates more frequently, more rapidly, with greater duration and/or with greater affinity or avidity with that epitope relative to alternative epitopes. In one embodiment, the antibody, or antigen-binding fragment thereof, of the invention binds at least 10-fold more strongly to its target (human alpha synuclein) than to another molecule; preferably at least 50-fold more strongly and more preferably at least 100-fold more strongly. Preferably, the antibody, or antigen-binding fragment thereof, binds under physiological conditions, for example, in vivo. Thus, by "specifically binding" to amino acids 126-140 ([SEQ ID NO 2]) of human alpha-synuclein we include the ability of the antibody, or antigen-binding fragment thereof, to bind to amino acids 126-140 with such specificity and/or under such conditions. Methods suitable for determining such binding will be known to those skilled in the art, and exemplary methods are described in the accompanying Examples. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in either a BIAcore 3000 or T200 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000-fold.

The term "kd" (sec−1 or 1/s), as used herein, refers to the dissociation rate constant of a particular antibody-antigen interaction. Said value is also referred to as the koff value.

The term "ka" (M−1×sec−1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M−1 or 1/M), as used herein, refers to the association equilibrium constant of a particular antibody-antigen interaction and is obtained by dividing the ka by the kd.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to alpha-synuclein, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The invention thus contemplates the use of random mutagenesis to identify improved CDRs. In the context of the present invention, conservative substitutions may be defined by substitutions within the classes of amino acids reflected in one or more of the following three tables:

Amino Acid Residue Classes for Conservative Substitutions:

TABLE 2

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Cly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic antigen-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-*1 *gp*41," MAbs 1(5):462-474; Gustchina, E. et al. (2009) "*Affinity Maturation By Targeted Diversification Of The CDR-H*2 *Loop Of A Monoclonal Fab Derived From A Synthetic Naïve Human Antibody Library And Directed Against The Internal Trimeric Coiled-Coil Of Gp*41 *Yields A Set Of Fabs With Improved HIV-*1 *Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "*Affinity Maturation Of Antibodies Assisted By In Silico Modeling*," Proc. Natl. Acad. Sci. (USA) 105(26): 9029-9034.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding and other amino acid residues, which are not directly involved in the binding, such as amino acid residues which are effectively blocked by the specifically antigen binding peptide (in other words, the amino acid residue is within the footprint of the specifically antigen binding peptide).

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody of the invention, refers to an amount sufficient, at dosages and for periods of time necessary, to achieve an intended biological effect or a desired therapeutic result including, without limitation, clinical results. The phrase "therapeutically effective amount" when applied to an antibody of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody in combinations with other compounds. In such instances, the "effective amount" is the amount of the combination sufficient to cause the intended biological effect.

A therapeutically effective amount of an anti-alpha-synuclein antibody may vary according to factors such as the disease state, age, sex, and weight of the individual, and the ability of the anti-alpha-synuclein antibody to elicit a desired response in the individual. A therapeutically effective amount is also one in which any toxic or detrimental effects of the antibody or antibody portion are outweighed by the therapeutically beneficial effects.

The present invention provides a monoclonal antibody competing with the antibody denoted 2E6 herein for binding to an epitope on alpha-synuclein. In particular the antibodies bind specifically to an epitope within amino acids 126-140 (SEQ ID No 2). In a specific embodiment the antibody may bind the epitope comprising or consisting of P138, E139 and A140.

The antibodies are preferably a humanized antibody.

Accordingly, the invention relates to a monoclonal antibody or antigen-binding fragment thereof comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

According to an embodiment the monoclonal antibody or antigen-binding fragment thereof may comprise a light chain variable region of the amino acid sequence of SEQ ID NO:19 and heavy a chain variable region of the amino acid sequence of SEQ ID NO:20.

According to another embodiment the monoclonal antibody or antigen-binding fragment thereof may comprise a light chain variable region the amino acid sequence of SEQ ID NO:21 and heavy a chain variable region of the amino acid sequence of SEQ ID NO:22.

According to another embodiment the monoclonal antibody or antigen-binding fragment thereof may comprise a light chain variable region of the amino acid sequence of SEQ ID NO:23 and heavy a chain variable region of the amino acid sequence of SEQ ID NO:24.

According to another embodiment the monoclonal antibody or antigen-binding fragment thereof may comprise of the amino acid sequence of SEQ ID NO:25 and heavy a chain variable region of the amino acid sequence of SEQ ID NO:26.

According to another embodiment the monoclonal antibody or antigen-binding fragment thereof may comprise a light chain variable region of the amino acid sequence of SEQ ID NO:27 and heavy a chain variable region of the amino acid sequence of SEQ ID NO:28.

According to another embodiment the monoclonal antibody or antigen-binding fragment thereof may comprise a light chain variable region of the amino acid sequence of SEQ ID NO:45 and heavy a chain variable region of the amino acid sequence of SEQ ID NO:46.

In another embodiment the invention relates to a monoclonal antibody or antigen-binding fragment thereof comprising a light chain variable region comprising the following CDRs of:

SEQ ID NO: 9 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment may comprise a heavy chain variable region comprising the following CDRs:

SEQ ID NO: 12 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence of SEQ ID NO:35 and heavy a chain variable region of the amino acid sequence of SEQ ID NO:36.

In another embodiment the invention relates to a monoclonal antibody or antigen-binding fragment comprising a light chain variable region comprising the following CDRs of:

SEQ ID NO: 10 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 18 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region comprising or consisting of the amino acid sequence of SEQ ID NO:39 and heavy a chain variable region of the amino acid sequence of SEQ ID NO:40.

According to another embodiment the monoclonal antibody or antigen-binding fragment thereof may comprise a light chain variable region of the amino acid sequence of SEQ ID NO:41 and heavy a chain variable region of the amino acid sequence of SEQ ID NO:42.

In another embodiment of the invention the invention relates to a monoclonal antibody or antigen-binding fragment thereof comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 11 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence of SEQ ID NO:37 and heavy a chain variable region of the amino acid sequence of SEQ ID NO:38.

According to another embodiment of the invention the invention relates to a monoclonal antibody or antigen-binding fragment thereof comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 13 or an amino acid sequence having no more than 4 amino acid differences, or no more than 3 amino acid differences, or no more than 2 amino acid differences, or no more than 1 amino acid difference; and SEQ ID NO: 16 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence According to another embodiment the monoclonal antibody or antigen-binding fragment thereof may comprise a light chain variable region of the amino acid sequence of SEQ ID NO:29 and heavy a chain variable region of the amino acid sequence of SEQ ID NO:30.

According to another embodiment of the invention the invention relates to a monoclonal antibody or antigen-binding fragment thereof comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 14 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence of SEQ ID NO:33 and heavy a chain variable region of the amino acid sequence of SEQ ID NO:34.

According to an embodiment of the invention the invention relates to a monoclonal antibody or antigen-binding fragment thereof comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 15 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence of SEQ ID NO:43 and heavy a chain variable region comprising or consisting of the amino acid sequence of SEQ ID NO:44.

According to another embodiment of the invention the invention relates to a monoclonal antibody or antigen-binding fragment comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

The monoclonal antibody or antigen-binding fragment thereof may comprise a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 17 or an amino acid sequence having no more than 4 amino acid differences, or no more than 3 amino acid differences, or no more than 2 amino acid differences, or no more than 1 amino acid difference.

According to another embodiment the monoclonal antibody or antigen-binding fragment thereof may comprise a light chain variable region of the amino acid sequence of SEQ ID NO:31 and heavy a chain variable region comprising or consisting of the amino acid sequence of SEQ ID NO:32

The antibody may according to one embodiment be unable to elicit an immune response via known immunoglobulin receptors. The antibody can be altered as to limit or reduce its ability to interact with known immunoglobulin receptors. For example, the antibody could be deglycosylated, contain amino acid changes in the heavy chain constant region or both.

The present invention also provides a method of reducing alpha-synuclein aggregate formation in a patient, comprising administering to the patient in need of such treatment, a therapeutically effective amount of an antibody of the invention.

Further the antibodies may be in a composition together with a pharmaceutically acceptable carrier, diluent and/or stabilizer. The antibodies of the invention may be used in therapy. In particular the antibodies of the invention may be used in treating synucleinopathies such as Parkinson's disease (including idiopathic and inherited forms of Parkinson's disease), Gaucher's Disease, Diffuse Lewy Body Disease (DLBD), Lewy body variant of Alzheimer's disease (LBV), Combined Alzheimer's and Parkinson disease, pure autonomic failure and multiple system atrophy. The antibodies of the invention may also be able to treat people at risk of developing PD based on their genetic profile and/or non-PD core-symptoms that will make them likely to develop PD in the future.

The treatment may be chronic and the patient may be treated at least 2 weeks, such as at least for 1 month, 6, months, 1 year or more.

The antibodies of the present invention may for example be monoclonal antibodies produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or from non-human mammals such as rats, rabbits, dogs, sheep, goats, primates, etc.

In one embodiment, the antibody of the invention is a human antibody. Human monoclonal antibodies directed against alpha-synuclein may be generated using transgenic or transchromosomal mice carrying parts of the human immune system and with a partially inactivated mouse repetoir. Such transgenic and transchromosomic mice include mice referred to herein as HuMAb mice and KM mice, respectively.

The HuMAb mouse contains a human immunoglobulin gene minilocus that encodes unrearranged human heavy variable and constant (p and Y) and light variable and constant (K) chain immunoglobulin sequences, together with targeted mutations that inactivate the endogenous p and K chain loci (Lonberg, N. et al., Nature 368, 856-859 (1994)). Accordingly, such mice exhibit reduced expression of mouse IgM or IgK and in response to immunization, the introduced human heavy and light chain transgenes, undergo class switching and somatic mutation to generate high affinity human IgG, K monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5[J/K](Balb) as described in WO 09/097006.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-alpha-synuclein antibody of the present invention may be switched by known methods. For example, an antibody of the present invention that was originally IgM may be class switched to an IgG antibody of the present invention. Further, class switching techniques may be used to convert one IgG subclass to another, for instance from IgGI to IgG2. Thus, the effector function of the antibodies of the present invention may be changed by isotype switching to, e.g., an IgG1, IgG2, IgG3 or IgG4 antibody for various therapeutic uses. In one embodiment an antibody of the present invention is an IgG1 antibody, for instance an IgG1, K.

In one embodiment, the antibody of the invention is a full-length antibody, preferably an IgG antibody, in particular an IgG1, K antibody. In another embodiment, the antibody of the invention is an antibody fragment or a single-chain antibody.

In certain embodiments, a chimeric antibody is engineered to become a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat 'IUSA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Antibodies fragments may e.g. be obtained by fragmentation using conventional techniques, and the fragments screened for utility in the same manner as described herein for whole antibodies. For example, F(ab')2 fragments may be generated by treating antibody with pepsin. The resulting F(ab')2 fragment may be treated to reduce disulfide bridges to produce Fab' fragments. Fab fragments may be obtained by treating an IgG antibody with papain; Fab'-fragments may be obtained with pepsin digestion of IgG antibody. An F(ab')2 fragment may also be produced by binding Fab' described below via a thioether bond or a disulfide bond. A Fab'-fragment is an antibody fragment obtained by cutting a disulfide bond of the hinge region of the F(ab')2. A Fab'-fragment may be obtained by treating an F(ab')2 fragment with a reducing agent, such as dithiothreitol. Antibody fragment may also be generated by expression of nucleic acids encoding such fragments in recombinant cells (see for instance Evans et al., J. Immunol. Meth. 184, 123-38 (1995)). For example, a chimeric gene encoding a portion of an F(ab')2 fragment could include DNA sequences encoding the CH1 domain and hinge region of the H chain, followed by a translational stop codon to yield such a truncated antibody fragment molecule.

In one embodiment, the anti-alpha-synuclein antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-alpha-synuclein antibody is constructed by a method comprising: i) providing a nucleic acid construct encoding the light chain of said monovalent antibody, said construct comprising a nucleotide sequence encoding the VL region of a selected antigen specific anti-alpha-synuclein antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-alpha-synuclein antibody is a monovalent antibody, which comprises:

(i) a variable region of an antibody of the invention as described herein or an antigen binding part of the said region, and (ii) a CH region of an immunoglobulin or a antigen-binding fragment thereof comprising the CH2 and CH3 regions, wherein the CH region or antigen-binding fragment thereof has been modified such that the region corresponding to the hinge region and, if the immunoglobulin is not an IgG4 subtype, other regions of the CH region, such as the CH3 region, do not comprise any amino acid residues, which are capable of forming disulfide bonds with an identical CH region or other covalent or stable non-covalent inter-heavy chain bonds with an identical CH region in the presence of polyclonal human IgG.

In a further embodiment, the heavy chain of the monovalent anti-alpha-synuclein antibody has been modified such that the entire hinge has been deleted.

In another further embodiment, the sequence of said monovalent antibody has been modified so that it does not comprise any acceptor sites for N-linked glycosylation.

In another further embodiment, the monovalent Fab of synuclein antibody is joined to an additional Fab or scfv that targets a different protein to generate a bispecific antibody. A bispecific antibody can have a dual function, for example a therapeutic function imparted by an anti-synuclein binding domain and a transport function that can bind to a receptor molecule to enhance transfer cross a biological barrier, such as the blood brain barrier.

Anti-alpha-synuclein antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of an anti-alpha-synuclein antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

In general, anti-alpha-synuclein antibodies described herein may be modified by inclusion of any suitable number of modified amino acids and/or associations with such conjugated substituents. Suitability in this context is generally determined by the ability to at least substantially retain alpha-synuclein selectivity and/or the anti-alpha-synuclein specificity associated with the non-derivatized parent anti-alpha-synuclein antibody. The inclusion of one or more modified amino acids may be advantageous in, for example, increasing polypeptide serum half-life, reducing polypeptide antigenicity, or increasing polypeptide storage stability. Amino acid(s) are modified, for example, cotranslationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

Anti-alpha-synuclein antibodies may also be chemically modified by covalent conjugation to a polymer to for instance increase their circulating half-life. Exemplary polymers, and methods to attach them to peptides, are illustrated in for instance U.S. Pat. Nos. 4,766,106, 4,179,337, 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies may further be used in a diagnostic method or as a diagnostic imagining ligand.

In one embodiment, anti-alpha-synuclein antibodies comprising one or more radiolabeled amino acids are provided. A radiolabeled anti-alpha-synuclein antibody may be used for both diagnostic and therapeutic purposes (conjugation to radiolabeled molecules is another possible feature). Non-limiting examples of such labels include, but are not limited to bismuth ($^{213}Bi$), carbon ($^{11}C$, $^{13}C$, $^{14}C$), chromium ($^{51}Cr$), cobalt ($^{57}Co$, $^{60}Co$), copper ($^{64}Cu$), dysprosium ($^{165}Dy$), erbium ($^{169}Er$), fluorine ($^{18}F$), gadolinium ($^{153}Gd$, $^{159}Gd$), gallium ($^{68}Ga$, $^{67}Ga$), germanium ($^{68}Ge$), gold ($^{198}Au$), holmium ($^{166}Ho$), hydrogen ($^{3}H$), indium ($^{111}n$, $^{112}In$, $^{113}In$, $^{115}In$), iodine ($^{121}I$ $^{123}I$, $^{125}I$, $^{131}I$), iridium ($^{192}1r$), iron ($^{59}Fe$), krypton ($^{81m}Kr$), lanthanium ($^{140}La$), lutelium ($^{177}Lu$), manganese ($^{54}Mn$), molybdenum ($^{99}Mo$), nitrogen ($^{13}N$, $^{15}N$), oxygen ($^{15}O$), palladium ($^{103}Pd$), phosphorus ($^{32}P$), potassium ($^{42}K$), praseodymium ($^{142}Pr$), promethium ($^{149}Pm$), rhenium ($^{186}Re$, $^{188}Re$), rhodium ($^{105}Rh$), rubidium ($^{81}Rb$, $^{82}Rb$), ruthenium ($^{82}Ru$, $^{97}Ru$), samarium ($^{153}Sm$), scandium ($^{47}Sc$), selenium ($^{75}Se$), sodium ($^{24}Na$), strontium ($^{85}Sr$, $^{89}Sr$, $^{92}Sr$), sulfur ($^{35}S$), technetium ($^{99}Tc$), thallium ($^{201}Tl$), tin ($^{113}Sn$, $^{117}Sn$), xenon ($^{133}Xe$), ytterbium ($^{169}Yb$, $^{175}Yb$, $^{177}Yb$), yttrium ($^{90}Y$) and zinc ($^{65}Zn$). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl*-3-(Trimethylstannyl) *Benzoate As An Intermediate*," Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radioiodinated antibody for targeting tumors," Cancer Res. 50(3 Suppl):857s-861 s).

The invention also provides anti-alpha-synuclein antibodies that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus, in one embodiment the anti-alpha-synuclein antibody of the invention may be labelled with a fluorescent label, a chemiluminescent label, a paramagnetic label, a radioisotopic label or an enzyme label. The labelled antibody may be used in detecting or measuring the presence or amount of said alpha-synuclein in the brain of a subject. This method may comprise the detection or measurement of in vivo imaging of anti-alpha-synuclein antibody bound to said alpha-synuclein and may comprises ex vivo imaging of said anti-alpha-synuclein antibody bound to said alpha-synuclein.

In a further aspect, the invention relates to an expression vector encoding one or more polypeptide chains of an antibody of the invention or an antigen-binding fragment thereof. Such expression vectors may be used for recombinant production of antibodies of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-alpha-synuclein antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a $CaPO_4$-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of an anti-alpha-synuclein antibody or an anti-alpha-synuclein binding antigen-binding fragment thereof in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

In an expression vector of the invention, anti-alpha-synuclein antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-alpha-synuclein antibody of the present invention or an alpha-synuclein binding antigen-binding fragment thereof. In another embodiment, the present invention provides a cell comprising a non-integrated nucleic acid, such as a plasmid, cosmid, phagemid, or linear expression element, which comprises a sequence coding for expression of an anti-alpha-synuclein antibody of the invention.

In a further aspect, the invention relates to a method for producing an anti-alpha-synuclein antibody of the invention, said method comprising the steps of a) culturing a hybridoma or a host cell of the invention as described herein above, and b) purifying the antibody of the invention from the culture media.

In an even further aspect, the invention relates to a pharmaceutical composition comprising:

an anti-alpha-synuclein antibody as defined herein, and
a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22th Edition, Gennaro, Ed., Mack Publishing Co., Easton, Pa., 2013.

Pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include i.a. intravenous, intramuscular, intraarterial, intrathecal, intradermal, intraperitoneal, subcutaneous, subcuticular, intraarticular, subarachnoid, intraspinal injection and infusion.

Additional suitable routes of administering a compound of the present invention in vivo and in vitro are well known in the art and may be selected by those of ordinary skill in the art.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems.

Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the anti alpha-synuclein antibodies depend on the disease or condition to be treated and may be determined by the persons skilled in the art. On any given day that a dosage is given, the dosage may range from about 0.01 to about 10 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight.

A physician having ordinary skill in the art may readily determine and prescribe the effective amount of the pharmaceutical composition required. For example, the physician could start doses of the anti-alpha-synuclein antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above. Labelled antibodies of the invention can be used for diagnostic purposes to detect, diagnose, or monitor diseases or disorders. The invention provides for the detection or diagnosis of a neurodegenerative or cognitive disease or disorder, including but not limited to Alzheimer's Disease, comprising: (a) assaying the existence of pyroglutamated Aβ fragments in cells or tissue samples of a subject using one or more antibodies that specifically bind to alpha-synuclein; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

Antibodies of the invention can be used to assay alpha-synuclein monomer, oligomers, fibrillary forms or fragments of alpha-synuclein in a biological sample using immunohistochemical methods well-known in the art. Other antibody-based methods useful for detecting protein include immunoassays such as the enzyme linked immunoassay (ELISA), radioimmunoassay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}I$, $^{131}I$), carbon ($^{14}C$), sulfur ($^{35}S$), tritium ($^{3}H$), indium ($^{121}In$), and technetium ($^{99m}Tc$); and luminescent labels, such as luminol and luciferase; and fluorescent labels, such as fluorescein and rhodamine.

The presence of labeled anti-alpha-synuclein antibodies or their alpha-synuclein-binding fragments may be detected in vivo for diagnosis purposes. In one embodiment, diagnosis comprises: a) administering to a subject an effective amount of such labeled molecule; b) waiting for a time interval following administration to allow the labeled molecule to concentrate at sites (if any) of Aβ deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention relates to an antibody, or antigen-binding fragment thereof, of the invention, for use in medicine.

In a further aspect, the invention relates to an antibody, or antigen-binding fragment thereof, of the invention, for use in treating, diagnosing or imaging synucleinopathies In one embodiment, the monoclonal antibody, or antigen-binding fragment thereof, is for use in treating Parkinson's disease, idiopathic Parkinson's disease, Diffuse Lewy Body Disease (DLBD), Lewy body variant of Alzheimer's disease (LBV), Combined Alzheimer's and Parkinson's disease, pure autonomic failure or multiple system atrophy.

In a further aspect, the invention relates to the use of the antibody, or antigen-binding fragment thereof, of the invention, in the manufacture of a medicament for treating, diagnosing or imaging synucleinopathies.

In a further aspect, the invention relates to a treating, diagnosing or imaging Parkinson's disease or other synucleinopathies, comprising administering an effective dosage of an antibody, or an antigen-binding fragment thereof, of the invention.

Preferably, in the uses and methods of those aspects of the invention, the treatment is chronic, and is preferably for at least 2 weeks, such as at least for 1 month, 6, months, 1 year or more.

In a further aspect, the invention provides a kit comprising the antibody, or antigen-binding fragment thereof, of the invention.

| Sequences | | | |
|---|---|---|---|
| SEQ ID NO | Description | | |
| 1 | α-synuclein | | |
| 2 | Epitope 126-140 | | |
| 3 | CDR1 | VL | |
| 4 | CDR2 | VL | |
| 5 | CDR3 | VL | |
| 6 | CDR1 | VH | |
| 7 | CDR2 | VH | |
| 8 | CDR3 | VH | |
| 9 | CDR1 | VL | 7C4 |
| 10 | CDR1 | VL | 7A10 & 8D9 |
| 11 | CDR3 | VL | L3 |
| 12 | CDR1 | VH | 7C4 |
| 13 | CDR2 | VH | 5A1 |
| 14 | CDR2 | VH | 9G11 |
| 15 | CDR2 | VH | 9C12 |
| 16 | CDR3 | VH | 5A1 |
| 17 | CDR3 | VH | 9D7 |
| 18 | CDR3 | VH | 7A10 & 8D9 |
| 19 | Full length | VL | m2E6 |
| 20 | Full length | VH | m2E6 |
| 21 | Full length | VL | ch2E6 |
| 22 | Full length | VH | ch2E6 |
| 23 | Full length | VL | 2E6-HLD1 |
| 24 | Full length | VH | 2E6-HLD1 |
| 25 | Full length | VL | 2E6-HLD2 |
| 26 | Full length | VH | 2E6-HLD2 |
| 27 | Full length | VL | 2E6-HLD3 |
| 28 | Full length | VH | 2E6-HLD3 |
| 29 | Full length | VL | 5A1 |
| 30 | Full length | VH | 5A1 |
| 31 | Full length | VL | 9D7 |
| 32 | Full length | VH | 9D7 |
| 33 | Full length | VL | 9G11 |
| 34 | Full length | VH | 9G11 |
| 35 | Full length | VL | 7C4 |
| 36 | Full length | VH | 7C4 |
| 37 | Full length | VL | L3 |
| 38 | Full length | VH | L3 |
| 39 | Full length | VL | 7A10 |
| 40 | Full length | VH | 7A10 |
| 41 | Full length | VL | 8D9 |
| 42 | Full length | VH | 8D9 |
| 43 | Full length | VL | 9C12 |
| 44 | Full length | VH | 9C12 |
| 45 | Full length | VL | 6B6 |
| 46 | Full length | VH | 6B6 |
| 47 | Full length | VH | 9E4 |
| 48 | Full length | VL | 9E4 |

Embodiments of the Invention

As would be apparent from the text and the Examples the invention further relates to the below embodiments

EMBODIMENTS

1. A monoclonal antibody, or antigen-binding fragment thereof, capable of specifically binding to an epitope within amino acids 126-140 on alpha-synuclein (SEQ ID NO. 2).
2. The monoclonal antibody, or antigen-binding fragment thereof, according to embodiment 1 which competes with any of the antibodies m2E6, ch2E6, 2E6-HLD1, 2E6-HLD2 or 2E6-HLD3, 7A10, 5A1, 9D7, 9G11, 7C4, L3, 8D9, 9C12 or 6B6 for binding to said epitope.
3. The monoclonal antibody or antigen-binding fragment thereof according to embodiment 1 or 2 wherein the antibody comprises or consists of an intact antibody.
4. The monoclonal antibody, or antigen-binding fragment thereof, according to embodiment 1 or 2 comprising or consisting of an antigen-binding fragment selected from the group consisting of Fv fragments (e.g. single chain Fv and disulphide-bonded Fv), Fab-like fragments (e.g. Fab fragments, Fab' fragments and $F(ab)_2$ fragments) and domain antibodies (e.g. single $V_H$ variable domains or $V_L$ variable domains).
5. The monoclonal antibody, or antigen-binding fragment thereof, according to any one of the preceding embodiments wherein the monoclonal antibody is selected from the group consisting of antibodies of subtype IgG1, IgG2, IgG3 and IgG4.
6. The monoclonal antibody, or antigen-binding fragment thereof, according to any one of the preceding embodiments wherein the antibody or antigen-binding fragment exhibits one or more of the following properties:
   - a binding affinity (KD) for alpha-synuclein between 0.5-10 nM, such as 1-5 nM or 1-2 nM;
   - capability of inhibiting accumulations of alpha-synuclein fibrils in neuronal cells;
   - capability of inhibiting transfer of alpha-synuclein fibrils from cell to cell;
   - capability of inhibiting intracellular seeding of alpha-synuclein;
   - capability of reversing impairment in basal synaptic transmission in F28-snca transgenic mice;
   - capability of reducing levels of alpha-synuclein in the mouse hippocampus as measured by in vivo microdialysis;
   - capability, when administered chronically, to normalize the pathological irregular and bursty firing pattern in the subthalamic nuclei (STN) in a rat model of Parkinson's disease; and/or
   - capability, when dosed chronically reverse impairment in PPF in hippocampus in transgenic alpha-synuclein mice.
7. The monoclonal antibody or antigen-binding fragment thereof according to any one of the preceding embodiments that is human or humanized.
8. The monoclonal antibody or antigen-binding fragment thereof according to any one of the preceding embodiments comprising a light chain variable region comprising the following CDRs of:
   - SEQ ID NO: 3 or an amino acid sequence having no more than 4 amino acid differences, or no more than 3 amino acid differences, or no more than 2 amino acid differences, or no more than 1 amino acid difference;
   - SEQ ID NO: 4 or an amino acid sequence having no more than 4 amino acid differences, or no more than 3 amino acid differences, or no more than 2 amino acid differences, or no more than 1 amino acid difference; and
   - SEQ ID NO: 5 or an amino acid sequence having with no more than 4 amino acid differences, or no more than 3 amino acid differences, or no more than 2 amino acid differences, or no more than 1 amino acid difference.
9. The monoclonal antibody or antigen-binding fragment thereof according to Embodiment 8 comprising a light chain variable region comprising the CDRs of SEQ ID NOs 3, 4 and 5.
10. The monoclonal antibody or antigen-binding fragment thereof according to any one of the preceding embodiments comprising a heavy chain variable region comprising the following CDRs:
   - SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

11. The monoclonal antibody or antigen-binding fragment thereof according to Embodiment 10 comprising a heavy chain variable region comprising the CDRs of SEQ ID NOs 6, 7 and 8.

12. The monoclonal antibody or antigen-binding fragment thereof according to Embodiments 8 or 9 comprising a light chain variable region comprising or consisting of the amino acid sequence of SEQ ID NO: 19.

13. An antibody or antigen-binding fragment thereof according to Embodiments 10 or 11 comprising a heavy chain variable region comprising or consisting of the amino acid sequence of SEQ ID NO:20.

14. The monoclonal antibody or antigen-binding fragment thereof according to Embodiments 12 and 13 comprising a light chain variable region comprising or consisting of the amino acid sequence of SEQ ID NO:19 and heavy a chain variable region comprising or consisting of the amino acid sequence of SEQ ID NO:20.

15. The monoclonal antibody or antigen-binding fragment thereof according to Embodiments 8 or 9 comprising a light chain variable region comprising or consisting of the amino acid sequence of SEQ ID NO: 21.

16. An antibody or antigen-binding fragment thereof according to Embodiments 10 or 11 comprising a heavy chain variable region comprising or consisting of the amino acid sequence of SEQ ID NO:22.

17. The monoclonal antibody or antigen-binding fragment thereof according to Embodiments 15 and 16 comprising a light chain variable region comprising or consisting of the amino acid sequence of SEQ ID NO:21 and heavy a chain variable region comprising or consisting of the amino acid sequence of SEQ ID NO:22.

18. The monoclonal antibody or antigen-binding fragment thereof according to Embodiments 8 or 9 comprising a light chain variable region comprising or consisting of the amino acid sequence of SEQ ID NO: 23.

19. An antibody or antigen-binding fragment thereof according to Embodiments 10 or 11 comprising a heavy chain variable region comprising or consisting of the amino acid sequence of SEQ ID NO:24.

20. The monoclonal antibody or antigen-binding fragment thereof according embodiments 18 and 19 comprising a light chain variable region comprising or consisting of the amino acid sequence of SEQ ID NO:23 and heavy a chain variable region comprising or consisting of the amino acid sequence of SEQ ID NO:24.

21. The monoclonal antibody or antigen-binding fragment thereof according to Embodiments 8 or 9 comprising a light chain variable region comprising or consisting of the amino acid sequence of SEQ ID NO: 25.

22. An antibody or antigen-binding fragment thereof according to Embodiments 10 or 11 comprising a heavy chain variable region comprising or consisting of the amino acid sequence of SEQ ID NO: 26.

23. The monoclonal antibody or antigen-binding fragment thereof according to embodiments 21 and 22 comprising a light chain variable region comprising or consisting of the amino acid sequence of SEQ ID NO:25 and heavy a chain variable region comprising or consisting of the amino acid sequence of SEQ ID NO:26.

24. The monoclonal antibody or antigen-binding fragment thereof according to Embodiments 8 or 9 comprising a light chain variable region comprising or consisting of the amino acid sequence of SEQ ID NO: 27.

25. An antibody or antigen-binding fragment thereof according to Embodiments 10 or 11 comprising a heavy chain variable region comprising or consisting of the amino acid sequence of SEQ ID NO: 28.

26. The monoclonal antibody or antigen-binding fragment thereof according to embodiments 24 and 25 comprising a light chain variable region comprising or consisting of the amino acid sequence of SEQ ID NO:27 and heavy a chain variable region comprising or consisting of the amino acid sequence of SEQ ID NO:28.

27. The monoclonal antibody or antigen-binding fragment thereof according to Embodiments 8 or 9 comprising a light chain variable region comprising or consisting of the amino acid sequence of SEQ ID NO: 45.

28. An antibody or antigen-binding fragment thereof according to Embodiments 10 or 11 comprising a heavy chain variable region comprising or consisting of the amino acid sequence of SEQ ID NO: 46.

29. The monoclonal antibody or antigen-binding fragment thereof according embodiments 27 and 28 comprising a light chain variable region comprising or consisting of the amino acid sequence of SEQ ID NO:45 and heavy a chain variable region comprising or consisting of the amino acid sequence of SEQ ID NO:46.

30. The monoclonal antibody or antigen-binding fragment thereof according to any one of embodiments 1-7 comprising a light chain variable region comprising the following CDRs of:

SEQ ID NO: 9 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

31. The monoclonal antibody or antigen-binding fragment thereof according to Embodiment 30 comprising a light chain variable region comprising the CDRs of SEQ ID NOs 9, 4 and 5.

32. The monoclonal antibody or antigen-binding fragment thereof according to any one of the embodiments 30 or 31 comprising a heavy chain variable region comprising the following CDRs:

SEQ ID NO: 12 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

33. The monoclonal antibody or antigen-binding fragment thereof according to Embodiment 32 comprising a heavy chain variable region comprising the CDRs of SEQ ID NOs 12, 7 and 8.

34. The monoclonal antibody or antigen-binding fragment thereof according to Embodiments 30 or 31 comprising a light chain variable region comprising or consisting of the amino acid sequence of SEQ ID NO: 35.

35. An antibody or antigen-binding fragment thereof according to Embodiments 32 or 33 comprising a heavy chain variable region comprising or consisting of the amino acid sequence of SEQ ID NO:36.

36. The monoclonal antibody or antigen-binding fragment thereof according embodiments 34 and 35 comprising a light chain variable region comprising or consisting of the amino acid sequence of SEQ ID NO:35 and heavy a chain variable region comprising or consisting of the amino acid sequence of SEQ ID NO:36.

37. The monoclonal antibody or antigen-binding fragment thereof according to any one of embodiments 1-7 comprising a light chain variable region comprising the following CDRs of:

SEQ ID NO: 10 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

38. The monoclonal antibody or antigen-binding fragment thereof according to Embodiment 37 comprising a light chain variable region comprising the CDRs of SEQ ID NOs 10, 4 and 5.

39. The monoclonal antibody or antigen-binding fragment thereof according the preceding embodiments 37 or 38 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 18 or an amino acid sequence having no more than 4 amino acid differences, or no more than 3 amino acid differences, or no more than 2 amino acid differences, or no more than 1 amino acid difference.

40. The monoclonal antibody or antigen-binding fragment thereof according to Embodiment 39 comprising a heavy chain variable region comprising the CDRs of SEQ ID NOs 6, 7 and 18.

41. The monoclonal antibody or antigen-binding fragment thereof according to Embodiments 37 or 38 comprising a light chain variable region comprising or consisting of the amino acid sequence of SEQ ID NO: 39.

42. An antibody or antigen-binding fragment thereof according to Embodiments 39 or 40 comprising a heavy chain variable region comprising or consisting of the amino acid sequence of SEQ ID NO:40.

43. The monoclonal antibody or antigen-binding fragment thereof according embodiments 41 and 42 comprising a light chain variable region comprising or consisting of the amino acid sequence of SEQ ID NO:39 and heavy a chain variable region comprising or consisting of the amino acid sequence of SEQ ID NO:40.

44. The monoclonal antibody or antigen-binding fragment thereof according to Embodiments 37 or 38 comprising a light chain variable region comprising or consisting of the amino acid sequence of SEQ ID NO: 41.

45. An antibody or antigen-binding fragment thereof according to Embodiments 39 and 40 comprising a heavy chain variable region comprising or consisting of the amino acid sequence of SEQ ID NO:42.

46. The monoclonal antibody or antigen-binding fragment thereof according embodiments 44 and 45 comprising a light chain variable region comprising or consisting of the amino acid sequence of SEQ ID NO:41 and heavy a chain variable region comprising or consisting of the amino acid sequence of SEQ ID NO:42.

47. The monoclonal antibody or antigen-binding fragment thereof according to any one of embodiments 1-7 comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 11 or an amino acid sequence having with no more than 4 amino acid differences, or no more than 3 amino acid differences, or no more than 2 amino acid differences, or no more than 1 amino acid difference.

48. The monoclonal antibody or antigen-binding fragment thereof according to Embodiment 47 comprising a light chain variable region comprising the CDRs of SEQ ID NOs 3, 4 and 11.

49. The monoclonal antibody or antigen-binding fragment thereof according the preceding embodiments 47 or 49 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

50. The monoclonal antibody or antigen-binding fragment thereof according to Embodiment 49 comprising a heavy chain variable region comprising the CDRs of SEQ ID NOs 6, 7 and 8.

51. The monoclonal antibody or antigen-binding fragment thereof according to Embodiments 47 or 48 comprising a light chain variable region comprising or consisting of the amino acid sequence of SEQ ID NO: 37.

52. The antibody or antigen-binding fragment thereof according to Embodiments 49 or 50 comprising a heavy chain variable region comprising or consisting of the amino acid sequence of SEQ ID NO:38.

53. The monoclonal antibody or antigen-binding fragment thereof according embodiments 51 and 52 comprising a light chain variable region comprising or consisting of the amino acid sequence of SEQ ID NO:37 and heavy a chain variable region comprising or consisting of the amino acid sequence of SEQ ID NO:38.

54. The monoclonal antibody or antigen-binding fragment thereof according to any one of embodiments 1-7 comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

55. The monoclonal antibody or antigen-binding fragment thereof according to Embodiment 54 comprising a light chain variable region comprising the CDRs of SEQ ID NOs 3, 4 and 5.

56. The monoclonal antibody or antigen-binding fragment thereof according the preceding embodiments 54 or 55 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 13 or an amino acid sequence having no more than 4 amino acid differences, or no more than 3 amino acid differences, or no more than 2 amino acid differences, or no more than 1 amino acid difference; and SEQ ID NO: 16 or an amino acid sequence having no more than 4 amino acid differences, or no more than 3 amino acid differences, or no more than 2 amino acid differences, or no more than 1 amino acid difference.

57. The monoclonal antibody or antigen-binding fragment thereof according to Embodiment 56 comprising a heavy chain variable region comprising the CDRs of SEQ ID NOs 6, 13 and 16.

58. The monoclonal antibody or antigen-binding fragment thereof according to Embodiments 54 or 55 comprising a light chain variable region comprising or consisting of the amino acid sequence of SEQ ID NO: 29.

59. The antibody or antigen-binding fragment thereof according to Embodiments 56 or 57 comprising a heavy chain variable region comprising or consisting of the amino acid sequence of SEQ ID NO:30.

60. The monoclonal antibody or antigen-binding fragment thereof according embodiments 58 and 59 comprising a light chain variable region comprising or consisting of the amino acid sequence of SEQ ID NO:29 and heavy a chain variable region comprising or consisting of the amino acid sequence of SEQ ID NO:30.

61. The monoclonal antibody or antigen-binding fragment thereof according to any one of embodiments 1-7 comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

62. The monoclonal antibody or antigen-binding fragment thereof according to Embodiment 61 comprising a light chain variable region comprising the CDRs of SEQ ID NOs 3, 4 and 5.

63. The monoclonal antibody or antigen-binding fragment thereof according the preceding embodiments 61 or 62 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 14 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

64. The monoclonal antibody or antigen-binding fragment thereof according to Embodiment 63 comprising a heavy chain variable region comprising the CDRs of SEQ ID NOs 6, 14 and 8.

65. The monoclonal antibody or antigen-binding fragment thereof according to Embodiments 61 or 62 comprising a light chain variable region comprising or consisting of the amino acid sequence of SEQ ID NO: 33.

66. The antibody or antigen-binding fragment thereof according to Embodiments 63 or 64 comprising a heavy chain variable region comprising or consisting of the amino acid sequence of SEQ ID NO:34.

67. The monoclonal antibody or antigen-binding fragment thereof according embodiments 65 and 66 comprising a light chain variable region comprising or consisting of the amino acid sequence of SEQ ID NO:33 and heavy a chain variable region comprising or consisting of the amino acid sequence of SEQ ID NO:34.

68. The monoclonal antibody or antigen-binding fragment thereof according to any one of embodiments 1-7 comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

69. The monoclonal antibody or antigen-binding fragment thereof according to Embodiment 68 comprising a light chain variable region comprising the CDRs of SEQ ID NOs 3, 4 and 5.

70. The monoclonal antibody or antigen-binding fragment thereof according the preceding embodiments 68 or 69 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 15 or an amino acid sequence having no more than 4 amino acid differences, or no more than 3 amino acid differences, or no more than 2 amino acid differences, or no more than 1 amino acid difference; and SEQ ID NO: 8 or an amino acid sequence having no more than 4 amino acid differences, or no more than 3 amino acid differences, or no more than 2 amino acid differences, or no more than 1 amino acid difference.

71. The monoclonal antibody or antigen-binding fragment thereof according to Embodiment 70 comprising a heavy chain variable region comprising the CDRs of SEQ ID NOs 6, 15 and 8.

72. The monoclonal antibody or antigen-binding fragment thereof according to Embodiments 68 or 69 comprising a light chain variable region comprising or consisting of the amino acid sequence of SEQ ID NO: 43.

73. The antibody or antigen-binding fragment thereof according to Embodiments 70 or 71 comprising a heavy chain variable region comprising or consisting of the amino acid sequence of SEQ ID NO:44.

74. The monoclonal antibody or antigen-binding fragment thereof according to any one of the preceding embodiments 72 and 73 comprising a light chain variable region comprising or consisting of the amino acid sequence of SEQ ID NO:43 and heavy a chain variable region comprising or consisting of the amino acid sequence of SEQ ID NO:44.

75. The monoclonal antibody or antigen-binding fragment thereof according to any one of embodiments 1-7 comprising a light chain variable region comprising the following CDRs of:

SEQ ID NO: 3 or an amino acid sequence having no more than 4 amino acid differences, or no more than 3 amino acid differences, or no more than 2 amino acid differences, or no more than 1 amino acid difference;

SEQ ID NO: 4 or an amino acid sequence having no more than 4 amino acid differences, or no more than 3 amino acid differences, or no more than 2 amino acid differences, or no more than 1 amino acid difference; and SEQ ID NO: 5 or an amino acid sequence having with no more than 4 amino acid differences, or no more than 3 amino acid differences, or no more than 2 amino acid differences, or no more than 1 amino acid difference.

76. The monoclonal antibody or antigen-binding fragment thereof according to Embodiment 75 comprising a light chain variable region comprising the CDRs of SEQ ID NOs 3, 4 and 5.

77. The monoclonal antibody or antigen-binding fragment thereof according the preceding embodiments 75 or 76 comprising a heavy chain variable region comprising the following CDRs:

SEQ ID NO: 6 or an amino acid sequence having no more than 4 amino acid differences, or no more than 3 amino acid differences, or no more than 2 amino acid differences, or no more than 1 amino acid difference;

SEQ ID NO: 7 or an amino acid sequence having no more than 4 amino acid differences, or no more than 3 amino acid differences, or no more than 2 amino acid differences, or no more than 1 amino acid difference; and SEQ ID NO: 17 or an amino acid sequence having no more than 4 amino acid differences, or no more than 3 amino acid differences, or no more than 2 amino acid differences, or no more than 1 amino acid difference.

78. The monoclonal antibody or antigen-binding fragment thereof according to Embodiment 77 comprising a heavy chain variable region comprising the CDRs of SEQ ID NOs 6, 7 and 17.

79. The monoclonal antibody or antigen-binding fragment thereof according to Embodiments 75 or 76 comprising a light chain variable region comprising or consisting of the amino acid sequence of SEQ ID NO: 31.

80. The antibody or antigen-binding fragment thereof according to Embodiments 77 or 78 comprising a heavy chain variable region comprising or consisting of the amino acid sequence of SEQ ID NO:32.

81. The monoclonal antibody or antigen-binding fragment thereof according embodiments 79 or 80 comprising a light chain variable region comprising or consisting of the amino acid sequence of SEQ ID NO:31 and heavy a chain variable region comprising or consisting of the amino acid sequence of SEQ ID NO:32 82. The monoclonal antibody or antigen-binding fragment thereof according to any one of the preceding embodiment comprising an Fc region.

83. The monoclonal antibody or antigen-binding fragment thereof according to any one of the preceding embodiment further comprising a moiety for increasing the in vivo half-life of the agent.

84. The monoclonal antibody or antigen-binding fragment thereof according to Embodiment 83 wherein the moiety for increasing the in vivo half-life is selected from the group consisting of polyethylene glycol (PEG), human serum albumin, glycosylation groups, fatty acids and dextran.

85. The monoclonal antibody or antigen-binding fragment thereof according to any one of the preceding embodiments wherein the antibody polypeptide further comprises a detectable moiety.

86. The monoclonal antibody or antigen-binding fragment thereof according to Embodiment 85 wherein the detectable moiety is a fluorescent label, a chemiluminescent label, a paramagnetic label, a radioisotopic label or an enzyme label.

87. The monoclonal antibody or antigen-binding fragment thereof according to Embodiment 85 or 86 wherein the detectable moiety comprises or consists of a radioisotope.

88. The monoclonal antibody or antigen-binding fragment thereof according to Embodiment 87 wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$TI.

89. The monoclonal antibody or antigen-binding fragment thereof according to Embodiment 87 wherein the detectable moiety comprises or consists of a paramagnetic isotope.

90. The monoclonal antibody or antigen-binding fragment thereof according to Embodiment 89 wherein the paramagnetic isotope is selected from the group consisting of $^{157}$Gd, $^{55}$Mn, $^{162}$Dy, $^{52}$Cr and $^{56}$Fe.

91. The monoclonal antibody or antigen-binding fragment thereof according to any of Embodiments 85 to 90 wherein the detectable moiety is detectable by an imaging technique such as SPECT, PET, MRI, optical or ultrasound imaging.

92. The monoclonal antibody or antigen-binding fragment thereof according to any of Embodiments 85 to 91 wherein the detectable moiety is joined to the antibody or antigen-binding fragment thereof indirectly, via a linking moiety.

93. The monoclonal antibody or antigen-binding fragment thereof according to Embodiment 92 wherein the linking moiety is selected from the group consisting of derivatives of 1,4,7,10-tetraazacyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA).

94. An isolated nucleic acid molecule encoding an antibody or antigen-binding fragment thereof according to any one of the preceding embodiments or a component polypeptide chain thereof.

95. A nucleic acid molecule according to Embodiment 94 wherein the molecule is a cDNA molecule.

96. A nucleic acid molecule according to Embodiment 94 or 95 encoding an antibody heavy chain or variable region thereof.

97. A nucleic acid molecule according to any one of Embodiments 94 to 96 encoding an antibody light chain or variable region thereof.

98. A vector comprising a nucleic acid molecule according to any one of Embodiments 94 to 97.

99. A recombinant host cell comprising a nucleic acid molecule according to any one of Embodiments 94 to 97 or a vector according to Embodiment 98.

100. A method for producing an antibody or antigen-binding fragment according to any one of the Embodiments 1 to 63, the method comprising culturing a host cell as defined in Embodiment 81 under conditions which permit expression of the encoded antibody or antigen-binding fragment thereof.

101. A pharmaceutical composition comprising the monoclonal antibody or antigen-binding fragment according to any one of Embodiments 1 to 81 and a pharmaceutical acceptable carrier.

102. The monoclonal antibody or antigen-binding fragment thereof of embodiments 1-81 for use in medicine.

103. The monoclonal antibody or antigen-binding fragment thereof of embodiments 1-81 for use in treating, diagnosing or imaging synucleinopathies.

104. The monoclonal antibody or antigen-binding fragment thereof according to embodiment 103 for use in treating Parkinson's disease (including idiopathic Parkinson's disease), Diffuse Lewy Body Disease (DLBD), Lewy body variant of Alzheimer's disease (LBV), Combined Alzheimer's and Parkinson disease, pure autonomic failure and multiple system atrophy.

105. Use of a monoclonal antibody or antigen-binding fragment thereof of embodiments 1-81 in the manufacturing of a medicament for treating, diagnosing or imaging synucleinopathies.

106. The use of a monoclonal antibody or antigen-binding fragment thereof according to embodiment 105 in the manufacturing of a medicament for treating Parkinson's disease (including idiopathic Parkinson's disease), Diffuse Lewy Body Disease (DLBD), Lewy body variant of Alzheimer's disease (LBV), Combined Alzheimer's and Parkinson disease, pure autonomic failure, multiple system atrophy as well as people at risk of developing PD based on their genetic profile and/or non-PD core-symptoms that will make them likely to develop PD in the future.

107. A method of treating, diagnosing or imaging synucleinopathies in a subject, said method comprising administering the pharmaceutical composition of embodiment 101 to said subject in an effective amount.

108. The antibody, or antigen-binding fragment thereof, for use according to Embodiment 103, or the use according to Embodiment 105, or the method according to Embodiment 107 for treating Parkinson's disease (including idiopathic Parkinson's disease), Diffuse Lewy Body Disease (DLBD), Lewy body variant of Alzheimer's disease (LBV), Combined Alzheimer's and Parkinson disease, pure autonomic failure and multiple system atrophy as well as people at risk of developing PD based on their genetic profile and/or non-PD core-symptoms that will make them likely to develop PD in the future.

109. The antibody, or antigen-binding fragment thereof, for use; or the use; or the method according to embodiment 103, 105 or 107, wherein the treatment is chronic 110. The antibody, or antigen-binding fragment thereof, for use; or the use; or the method according to embodiment 109, wherein the chronic treatment is for at least 2 weeks, such as at least for 1 month, 6, months, 1 year or more.
111. The antibody, or antigen-binding fragment thereof, for use; or the use; or the method according to any one of embodiments 102 to 110, wherein the subject is human.
112. A kit comprising the antibody or antigen-binding fragment thereof according to embodiments 1-81 for use in medicine.
113. The monoclonal antibody or antigen-binding fragment thereof of embodiments 85-93 for use in detecting or measuring the presence or amount of said alpha-synuclein in the brain or any other organ or body fluid of a subject.
114. The monoclonal antibody or antigen-binding fragment thereof of embodiments 113, wherein said detection or measurement comprises in vivo imaging of said anti-synuclein antibody bound to said alpha-synuclein.
115. The monoclonal antibody or antigen-binding fragment thereof of embodiments 85-93 wherein said detection or measurement comprises ex vivo imaging of said anti-synuclein antibody bound to said alpha-synuclein.

EXAMPLES

Example 1: Antibody Discovery

A. Immunization/Hybridoma Screening

Figure 7:
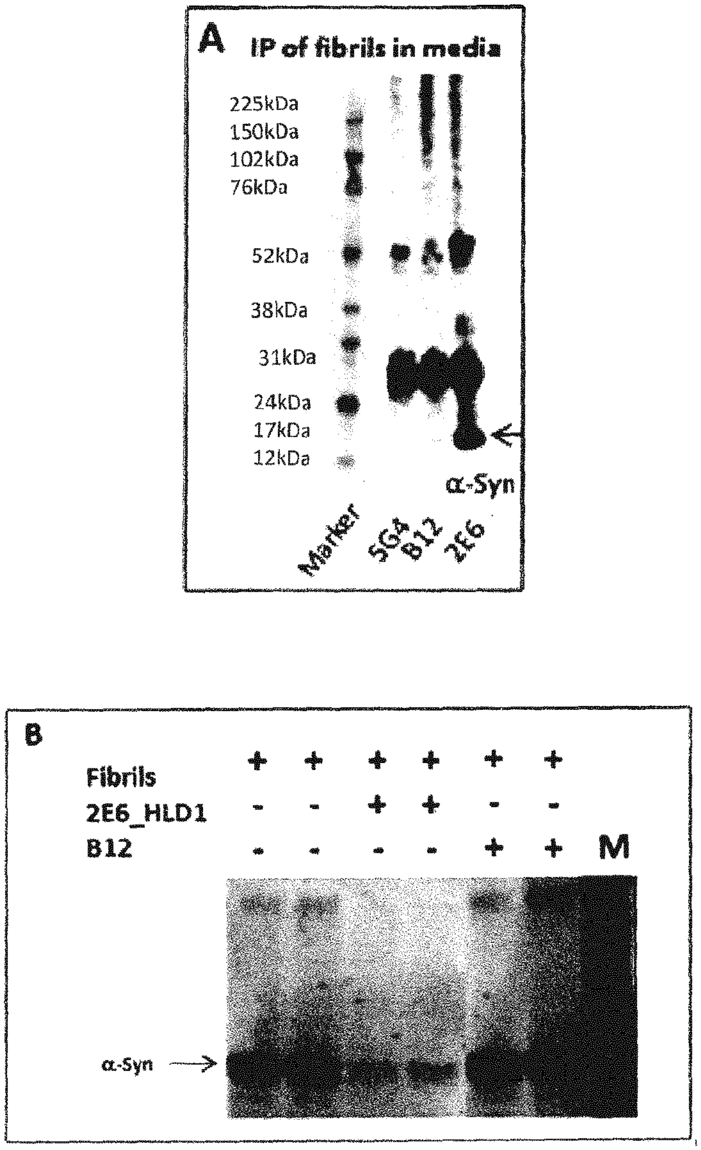
FIG. 7 shows that m2E6 binds to alpha-synuclein fibrils in media and inhibits their accumulation in non-phagocytic cells. A) Immunoprecipitation of alpha-synuclein fibrils added to cell culture media. This showed that m2E6 was able to recognize and pull down the alpha-synuclein fibrils from the media, whereas control antibodies B12 (non-reactive human IgG) and another alpha-synuclein antibody 5G4 (from Roboscreen) were not.
Figure 7:
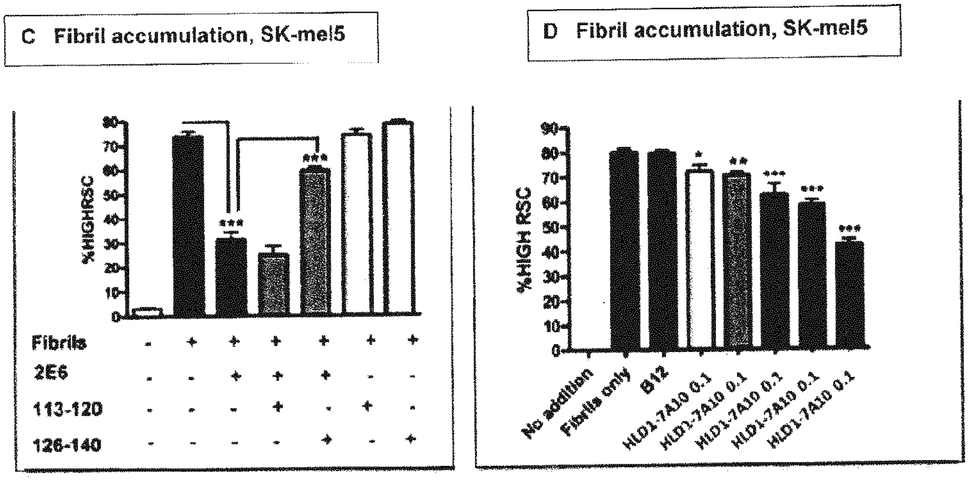

Monoclonal antibodies against alpha-synuclein were generated by immunizing mice with different synuclein aggregates cross linked with for example reactive aldehydes. The first antigen was made of recombinant lyophilized alpha-synuclein from Rpeptide (4241 Mars Hill Road, Bogart, Ga. 30622, USA). It was made by dissolving the protein in PBS to give a solution of 70 uM alpha-synuclein (1 mg/ml). The solution was incubated 18 hours at 37 degrees C. and frozen in 100 ul aliquots. The second antigen was made similarly from recombinant alpha-synuclein (Rpeptide) by dissolving it at 70 microM in 20 mM Tris (pH=7.4), 0.15 M NaCl. Reactive aldehyde ONE (4-oxo-2-Nonenal, Cat #10185 from Cayman Chemicals, Ann Arbor, Mich.) was added in a molar ratio of 20:1 to covalently cross link oligomers of alpha-synuclein. The solution was incubated for 18 hours at 37 C (without shaking). The unreacted ONE was removed by Vivaspin500 spin column (10 kDa MWCO) and the samples were dialyzed against 20 mM Tris, pH 7.4, 0.15 M NaCl, and frozen in aliquots. The third antigen was recombinant alpha-synuclein fragment amino acids 1-60 (Rpeptide) which was sent to as lyophilized powder (original material from Rpeptide). Briefly, three female mice (4-7 weeks old) were immunized and boosted up to three times. Tail-bleeds were taken and screened for anti-synuclein antibodies by enzyme-linked immunosorbent assay (ELISA) against the antigen. Titer is defined by the serum dilutions to achieve OD reading of 3-times the base line in an ELISA. Mice showing a titer greater than 1:50,000 over control were selected for fusion. Harvested splenocytes were fused to SP2/0 mouse myeloma cells, diluted and plated from single cell fusions. Supernatants were harvested 14 days post-fusion and screened for antibody production. Using the synuclein ELISA 50 positive clones were recovered from 1000 wells. A Clonotyping System/AP kit was used for immunoglobulin isotyping (Southern Biotechnology, Birmingham, Ala.). The 50 anti-alpha-synuclein supernatants were screened for reduction of accumulation of atto-labelled alpha-synuclein aggregates in the SKMEL5 cell assay as described in example 6 (FIG. 7C). The commercial antibody LB509 was included as positive control. It was found that out of the 50 antisera, only 4 antisera reduced the intracellular accumulation of alpha-synuclein and these antibodies were taken forward for cloning. These four antibodies were then tested in dose response in the assay. The antibody with largest effect, 2E6, was selected for further characterization in PD relevant models.

B. Synuclein ELISA

Antibody-positive fusions were analysed for binding using an antigen-specific ELISA assay. Corning 96 well high binding plates were coated with 100 ng of aggregated synuclein. Wells were blocked using 5% milk in PBS for 1 hour (hr) at room temperature (RT). Plates were washed 3 times using PBS+1% Tween 20. One hundred microliters of hybridoma supernatant were added to each well and plates were incubated at RT. Subsequently, HRP-conjugated goat anti-mouse IgG (H&L chain-specific or y-chain specific) secondary was added to each well to detect the presence of bound anti-synuclein antibody. For quantification substrate, One component TMB, was added and plates were measured at OD620

C. Determining the DNA Sequence of Antibody HC and LC Variable Domains

Four anti-alpha synuclein positive hybridomas were selected and mRNA was extracted from cell pellets. cDNAs from each mRNA prep were generated by reverse-transcriptase using oligo(dT) primers. Subsequently, PCR reactions were performed using variable domain primers to amplify both the VH and VL regions of the HC and LC genes. Amplified DNA was separated on an agarose gel and both the VH and VL products were isolated, purified from the gel, cloned into pCR2.1 (Invitrogen) and transformed into TOP10 cells. A minimum of 6 positive colonies were selected and analysed by DNA sequencing to determine the sequence of the VH and VL regions.

Example 2: Antibody Engineering

Expression of Monoclonal Antibodies

Cultures of hybridoma clones were expanded and mouse monoclonal antibodies were purified from the cultured supernatants using protein G chromatography. Recombinant mouse, human and chimeric antibodies were produced using transient co-transfection of heavy and light chain genes into HEK293 cells, expansion of the cultures, harvesting the supernatants and purification by protein chromatography. Instances where there was repeated need for gram quantities of antibodies stable cell lines were created in CHO cells. These stable cell lines could be expanded as needed and antibody purification was performed as before.

Cloning of Recombinant Antibodies

Recombinant monoclonal antibodies were generated by gene synthesis of the heavy and light chain genes (Geneart A/G). Synthesized genes were subsequently cloned into standard expression vectors (e.g. pcDNA3.1) for expression in mammalian cell culture.

Humanization

Humanization of m2E6 was carried out by structure based CDR grafting. The amino acid sequences of the 2E6 VL and VH domains were screened for homology against all human antibody VL and VH framework amino acid sequences found in the PDB and IMGT databases. Structural modeling was performed on the m2E6 Fv region using 20SL antibody from the PDB database. The 20SL amino acid sequences are 82.7% and 83.2% homologous to the 2E6 VH and VL domains, respectively. Importantly the structure for 20SL was determined at a resolution of 2.1A. Structural alignment of the 2E6 humanized framework with 20SL enabled determination of important residues in the framework regions that could potentially influence folding or local structure via steric hindrance or steric force. Theoretical antibody structural modeling of the humanized antibody was employed to instruct on the potential importance of maintaining specific residues as the original mouse amino acid in the humanized version of 2E6 in order to maintain binding specificity and affinity. The structural modeling was employed to optimize the activity of humanized 2E6.

Humanization of the 2E6 VH region was performed by grafting the VH CDRs onto the framework of the human germline gene, IGHV1-46*01 (69% homology). There are 23 amino acid differences between the mouse 2E6 and the selected human framework regions. Structural modeling identified 7 amino acid positions where the change to the human residue had the potential to negatively impact the activity of 2E6. These residues were back-mutated to the original mouse amino acids. Three different versions of the humanized heavy chain were produced. Humanized HLD-1 contains all 7 back mutations, M37V, 148M, A68V, L70M, V72R, K74T, A79V, HLD-2 contains 148M, A68V, L70M, V72R, K74T, A79V, and HLD-3 contains M37V, 148M, L70M, V72R, K74T, A79V.

Humanization of the 2E6 VL region was performed by grafting the VL CDRs onto the framework of the human germline gene, IGKV3-11*01 (64% homology). There are 26 amino acid differences between the mouse 2E6 and the selected human framework regions. Structural modeling identified 4 amino acid positions, R45L, W46L, V571, Y70F, where the change to the human residue had the potential to negatively impact the activity of 2E6. For HLD-1, HLD-2 and HLD-3 all 4 residues were back-mutated to the original mouse amino acids.

HLD-1, HLD-2 and HLD-3 were expressed transiently in HEK 293 cells. Antibodies were purified from cultured supernatants and subsequently analyzed for binding to synuclein by SPR (Biacore 3000) using the synuclein ligand format (Table 5).

TABLE 5

Kinetic binding analysis of different humanized 2E6 clones and chimeric 2E6

| | ka (1/Ms) | kd (1/s) | KA (1/M) | KD (nM) | Chi2 | KD improvement |
|---|---|---|---|---|---|---|
| Ch2E6 | 6.29E+04 | 2.65E−04 | 2.38E+08 | 4.21E−09 | 3.57 | 1 |
| HLD1 | 1.23E+05 | 2.12E−04 | 5.81E+08 | 1.72E−09 | 4.56 | 2 |
| HLD2 | 5.80E+04 | 2.85E−04 | 2.04E+08 | 4.91E−09 | 4.34 | 1 |
| HLD3 | 4.89E+04 | 2.60E−04 | 1.88E+08 | 5.32E−09 | 2.79 | 1 |

Affinity maturation of HLD1 was done by randomized mutations in the light chain CDR3 by codon based degenerated PCR primers, and similarly randomized mutations in the heavy chain CDR3 by codon based degenerated PCR primers and using in vitro evolution with error-prone PCR. Antibodies were purified from cultured supernatants and subsequently analyzed for binding to synuclein by SPR (Biacore 3000) using IgGs captured using anti human IgG Ab immobilized on the CM5 chip (Table 6).

TABLE 6

Kinetic binding analysis of different affinity matured versions of humanized 2E6 clone HLD1-after first round of affinity maturation

| | ka (1/Ms) | kd (1/s) | KA (1/M) | KD (M) | Chi2 | KD improvement |
|---|---|---|---|---|---|---|
| Ch2E6 | 2.45E+04 | 1.39E−03 | 1.76E+07 | 5.67E−08 | 0.22 | 1 |
| HLD1 | 4.16E+04 | 9.44E−04 | 4.40E+07 | 2.27E−08 | 0.164 | 2.5 |
| L3-11 | 1.45E+05 | 3.16E−04 | 4.60E+08 | 2.18E−09 | 0.285 | 26 |
| 7A10 | 5.17E+04 | 2.85E−04 | 1.81E+08 | 5.52E−09 | 0.297 | 10.3 |
| 9C12 | 4.95E+04 | 2.78E−04 | 1.78E+08 | 5.62E−09 | 0.631 | 10 |
| 8D9 | 7.41E+04 | 4.83E−04 | 1.53E+08 | 6.52E−09 | 0.301 | 8.7 |
| 7C4 | 1.23E+05 | 9.97E−04 | 1.23E+08 | 8.12E−09 | 1.04 | 7 |

After first round of affinity maturation we constructed 4 mutations (A, B, C, D): A) combined the two mutations in heavy chain CDR2 (mutate KYNVNFKT to KYNVNIKT) and heavy chain CDR3 (mutate LGHYGNLYAMDY to LGHYGNLYAKDY); B) incorporated light chain CDR1 mutation (mutate SASSSVSYMH to SASSSVSYIH) into the L3-11 light chain; C) incorporated light chain framework mutation (mutate PRRWIY to PRRLIY, immediately upstream CDR2) into the L3-11 light chain; and D) incorporated light chain CDR1 mutation (mutate SASSSVSYMH to SASSSVSYIH) and light chain framework mutation (mutate PRRWIY to PRRLIY) into the L3-11 light chain. Based on the Biacore data and antibody sequence, we tested co-expression of light chain and heavy chain with various combinations:

1. L3-11 light chain+9C12 heavy chain
2. L3-11 light chain+8D9 heavy chain
3. 7A10 light chain+9C12 heavy chain
4. L3-11 light chain+A
5. 7A10 light chain+A
9. B+9C12 heavy chain
10. C+9C12 heavy chain
11. D+9C12 heavy chain
12. B+8D9 heavy chain
13. C+8D9 heavy chain
14. D+8D9 heavy chain
15. B+heavy chain
16. C+heavy chain
17. D+heavy chain Antibodies were purified from cultured supernatants and subsequently analyzed for binding to synuclein by SPR (Biacore 3000) using IgGs captured using anti human IgG Ab immobilized on the CM5 chip (Table 7).

TABLE 7

Kinetic binding analysis of different affinity matured versions of humanized 2E6 clone HLD1-after combination of mutations

| | ka (1/Ms) | kd (1/s) | KA (1/M) | KD (M) | Chi2 | KD improvement |
|---|---|---|---|---|---|---|
| Ch2E6 | 2.45E+04 | 1.39E−03 | 1.76E+07 | 5.67E−08 | 0.22 | 1 |
| HLD1 | 4.16E+04 | 9.44E−04 | 4.40E+07 | 2.27E−08 | 0.164 | 2.5 |

TABLE 7-continued

Kinetic binding analysis of different affinity matured versions of humanized 2E6 clone HLD1-after combination of mutations

| | ka (1/Ms) | kd (1/s) | KA (1/M) | KD (M) | Chi2 | KD improvement |
|---|---|---|---|---|---|---|
| HDL1-14 | 1.35E+05 | 5.60E−05 | 2.42E+09 | 4.14E−10 | 0.03 | 137.0 |
| HDL1-12 | 2.47E+05 | 1.12E−04 | 2.21E+09 | 4.51E−10 | 0.12 | 125.7 |
| HDL1-13 | 1.46E+05 | 7.07E−05 | 2.07E+09 | 4.83E−10 | 0.11 | 117.4 |
| HDL1-15 | 2.58E+09 | 1.25E−04 | 2.06E+09 | 4.85E−10 | 0.09 | 116.9 |
| HDL1-9 | 2.60E+05 | 1.33E−04 | 1.94E+09 | 5.14E−10 | 0.06 | 110.3 |
| HLD1-16 | 1.53E+09 | 8.97E−05 | 1.71E+09 | 5.85E−10 | 0.14 | 96.9 |
| HDL1-2 | 2.38E+05 | 1.52E−04 | 1.57E+09 | 6.36E−10 | 0.06 | 89.2 |
| HDL1-3 | 9.99E+04 | 1.26E−04 | 7.94E+08 | 1.26E−09 | 0.06 | 45.0 |
| HDL1-5 | 9.29E+04 | 1.28E−04 | 7.27E+08 | 1.38E−09 | 0.03 | 41.1 |

Example 3: Epitope Mapping

Epitope mapping of the antibodies to alpha-synuclein was done with arrays of overlapping linear peptides at Pepscan (Pepscan Zuidersluisweg 2 8243 RC Lelystad The Netherlands). The binding of antibody to each of the synthesized 20 mer peptides was tested in a Pepscan based ELISA. The linear peptide array covering the entire coding sequence of alpha-synuclein, as well as all peptides with oxidized methionines or nitrosylated tyrosines, were incubated with primary antibody solution (overnight at 4° C.). After washing, the peptide arrays were incubated with a 1/1000 dilution of an antibody peroxidase conjugate (SBA,cat.nr.2010-05) for one hour at 25° C. After washing, the peroxidase substrate 2,2'-azino-di-3-ethylbenzthiazoline sulfonate (ABTS) and 2 μl/ml of 3 percent $H_2O_2$ were added. After one hour, the color development was measured. The color development was quantified with a charge coupled device (CCD)—camera and an image processing system. For data processing the values were obtained from the CCD camera range from 0 to 3000 mAU, similar to a standard 96-well plate ELISA-reader. The results were quantified and stored into the Peplab database. Occasionally a well contains an air-bubble resulting in a false-positive value, the cards are manually inspected and any values caused by an air-bubble are scored as 0.

Figure 1:
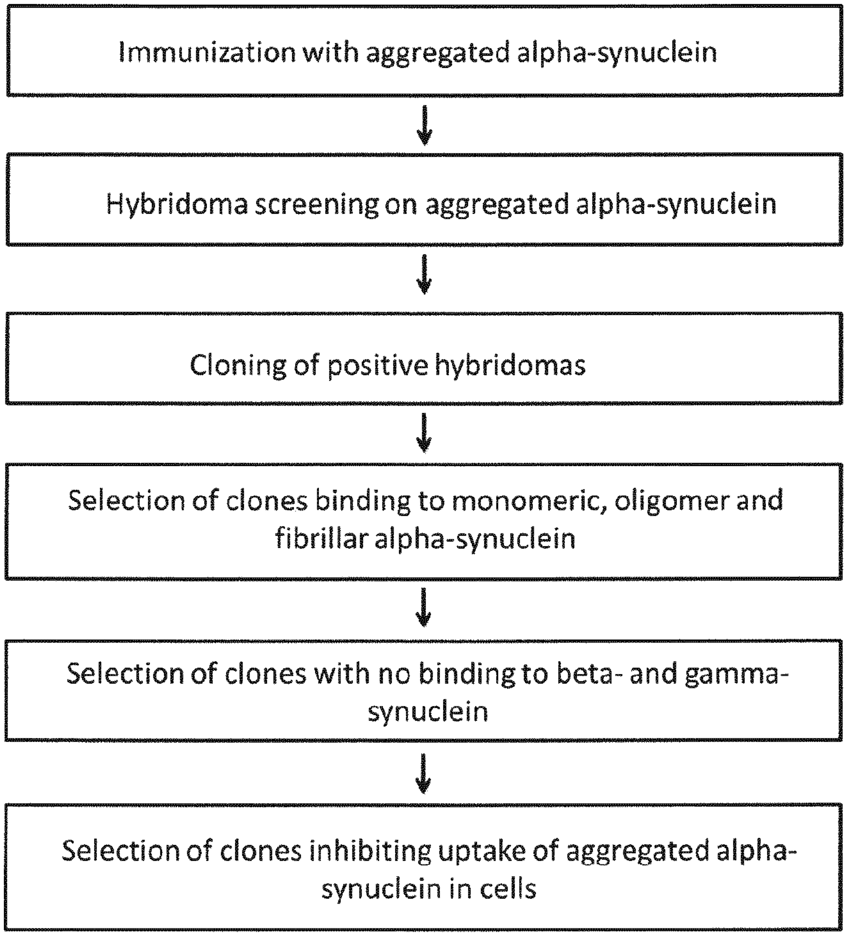
FIG. 1 shows the screenings cascade. Three mice were immunised with different aggregated forms of alpha-synuclein. The mice were screened for high titers and monoclonal cell lines were generated. Using an alpha-synuclein ELISA 50 positive clones were recovered from ~1000 wells. The fifty monoclonal antibodies recognising alpha-synuclein were screened for their ability to prevent accumulation of fibrillated alpha-synuclein in SK-mel5 cells (Example 1). Surprisingly only very few (four out of 50) alpha-synuclein antibodies were able to inhibit accumulation of fibrillated alpha-synuclein. m2E6 was selected as the most efficient antibody and further profiled in cellular and animal models of PD. Furthermore, m2E6 was humanized to 2E6-HLD-1, 2 and 3 (Example 2) and 2E6-HLD1 further affinity matured to HLD1-7A10. Kinetic binding data on all variants towards alpha-synuclein is listed in Table 5, 6 and 7) (Example 2).
Figure 2:
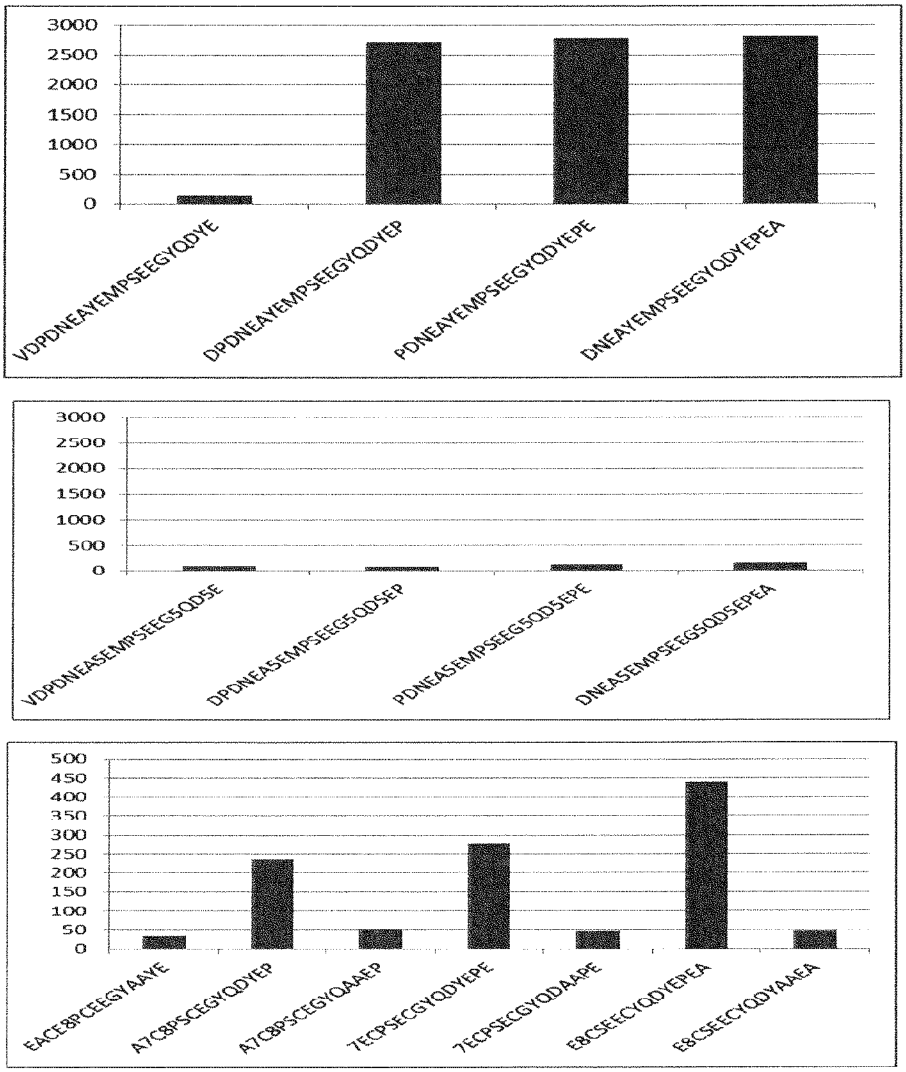
FIG. 2 shows ELISA data from epitope mapping of antibody m2E6 to peptides from alpha-synuclein amino acid sequence 136-140 (the other nonbinding peptides are not shown). Upper panel shows that peptide sequence YEPEA is required for full binding of antibody m2E6. Middle panel shows the same peptides where the tyrosine residue is replaced with nitro-tyrosine (shown as number 5 in the sequence). Nitration of tyrosine 136 abolished binding of the antibody to the peptide. The bottom panel shows double alanine scanning mutagenesis of selected amino acids. The Double Alanine replacements present in the array points towards a critical role for the penultimate amino acids P138, E139, and A 140. (Example 3).

Results can be seen in FIG. 2 for m2E6.

Example 4: Immunoprecipitation of Alpha-Synuclein from Human Brain Homogenates of Cingulate Cortex from Patients with Dementia with Lewy Bodies and Healthy Controls Alpha-Synuclein and Phosphorylated (Ser129) Alpha-Synuclein Levels in Brain Homogenates from Dementia with Lewy Body Patients (DLB) and Age Matched Healthy Controls (CTR).

Cingulate cortex samples from five brains from dementia with Lewy body patients (DLB) and five brain samples from age matched healthy controls (CTR) were used. Tissue blocks of app. 50-100 mg was homogenized in a CelLytic™ M cell lysis buffer (Sigma) with a Precellys CK-14 tissue homogenizer followed by a 30 min spin 3000 g, resulting in S1 and P1 fractions. Supernatant (S1) fraction contains the total detergent soluble alpha-synuclein, the pellet (P1) fraction contains the detergent insoluble alpha-synuclein (Lewy bodies). An additional centrifugation of the S1 fraction 30 min 20.000 g (P2) contains detergent soluble aggregated forms of alpha-synuclein and a 186.000 g spin (P3) contains detergent soluble smaller aggregated forms of alpha-synuclein and the remaining supernatant (S2) contains the monomeric alpha-synuclein.

Figure 3:
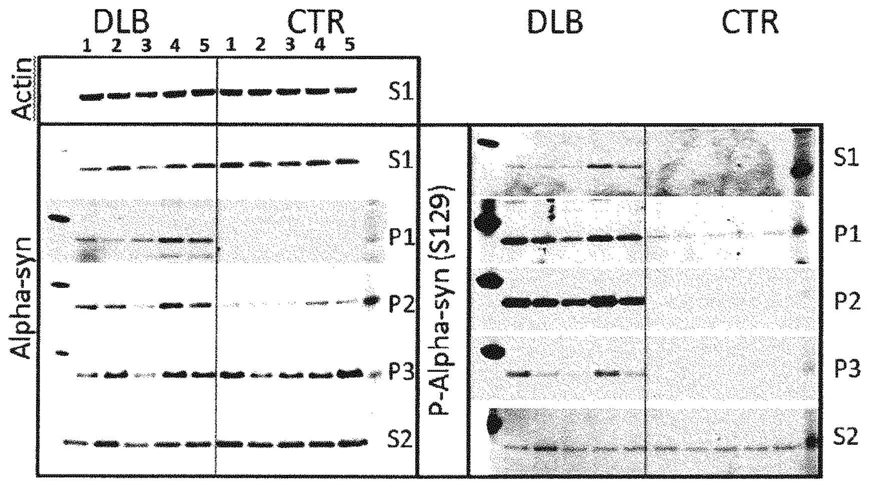
FIG. 3 shows the difference in the content of alpha-synuclein and phosphorylated (Ser129) alpha-synuclein between five brain homogenates from dementia with Lewy body patients (DLB) and age matched healthy controls (CTR). These homogenates are used for further fractionations to enrich for pathological forms of alpha-synuclein i.e. aggregated and phosphorylated at Ser129 (Example 4).

FIG. 3 shows the difference in the content of alpha-synuclein in the five brain homogenates from patients with dementia with Lewy body (DLB) and five age matched healthy controls (CTR). (Five lanes in the "alpha-syn" and "P-Alpha-syn(S129)" box represent the five different patients and the five controls) in the S1, P1, P2, P3 and S2 fractions. The level of soluble alpha-synuclein is similar in DLB and CTR (FIG. 3, left panel, "alpha-syn" in S1 and S2) whereas there is increased amount of insoluble alpha-synuclein in DLB (P1 fraction) as detected with a mouse monoclonal anti human alpha-synuclein (4B12, Thermo Scientific). The level of insoluble alpha-synuclein phosphorylated on serine 129 (FIG. 3, right panel "P-Alpha-syn (S129)" is increased in DLB (P1, P2 and P3 fraction) as detected with anti Ser-129-phosphorylated monoclonal antibody (ab51253, abcam)

Immunoprecipitation of Alpha-Synuclein from Fractions Enriched in Pathological Forms of Alpha-Synuclein The ability of the antibodies to bind to and pull down alpha-synuclein from the fractions S1, P1 and P2 from the combined fractions of human brain cingulate cortex from all five DLB patients was analyzed by immunoprecipitation. For immunoprecipitation, 2 μg of antibody was immobilized on magnetic Dynabeads protein G followed by immunoprecipitation 90 min at room temperature. The yield of the immunoprecipitation was visualized by Western blotting with detection antibody, mouse monoclonal anti human alpha-synuclein, (4B12, Thermo Scientific). The amount of alpha-synuclein pulled down differs between the mouse m2E6, the humanized 2E6-HLD-1 and the 9E4 antibody (SEQ ID NO 47 and 48). Also, the patterns of bands representing different molecular weight forms of alpha-synuclein being pulled down differ between the 2E6 antibodies and the comparator antibody 9E4, FIG. 4.

Figure 4:
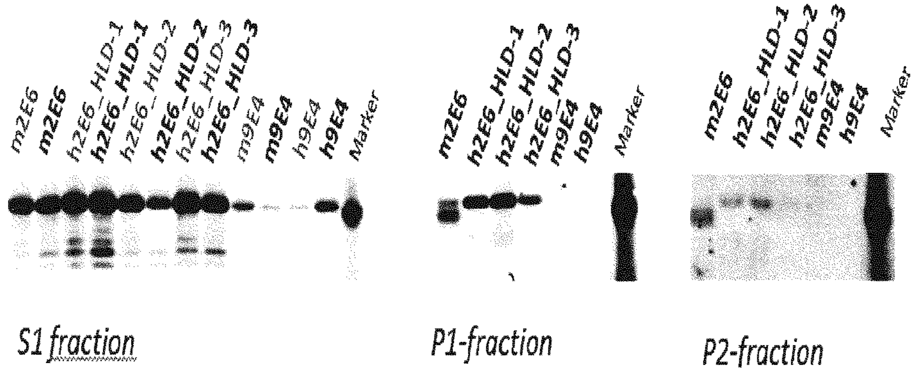
FIG. 4 shows immunoprecipitation of alpha-synuclein from soluble fraction (S1) and fractions enriched in pathological forms (P1 and P2) of alpha-synuclein from DLB patients (lanes with bold text) and age matched healthy controls (CTR) (lanes with grey text) with m2E6 and the humanized versions of m2E6; 2E6-HLD1, 2 and 3 antibodies. The figure shows that m2E6 and the humanized variants 2E6-HLD1-3 are markedly different from the comparator alpha-synuclein antibody 9E4 (both mouse and humanized form). m2E6 and humanized variants are able to immunoprecipitate truncated or alternatively spliced versions of alpha-synuclein whereas 9E4 does not. Furthermore m2E6 and the humanized variants recognize the pathological aggregated forms of alpha-synuclein in the P1 and P2 fractions whereas 9E4 does not (Example 4).

Immunoprecipitation of alpha-synuclein from human brains demonstrates that m2E6 and the humanized variants 2E6-HLD1-3 are markedly different from 9E4. 2E6 and humanized variants are able to immunoprecipitate lower molecular weight, alternatively spliced or truncated versions of alpha-syn whereas 9E4 do not. Furthermore, 2E6 and the humanized variants recognize the pathological aggregated forms of alpha-synuclein in the P1 and P2 fractions whereas 9E4 does not (FIG. 4).

Figure 5:
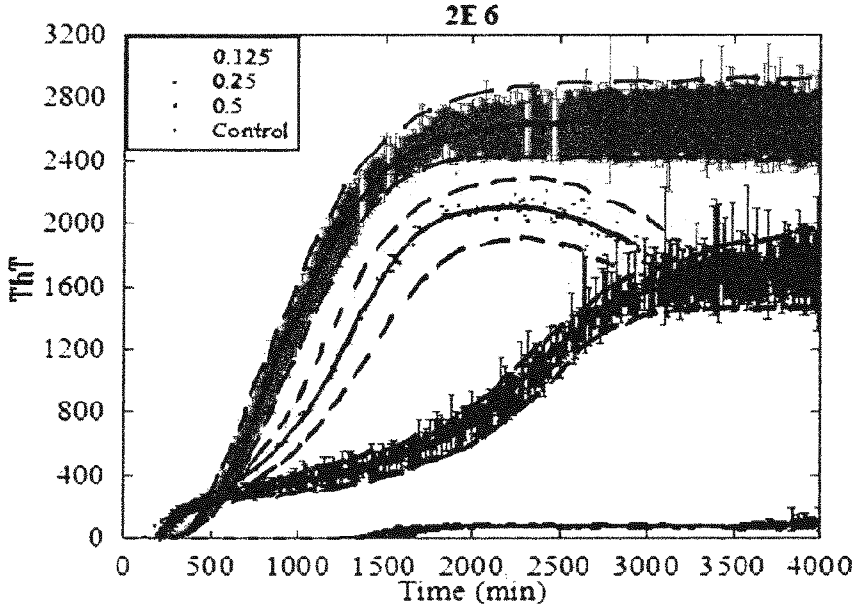
FIG. 5 shows inhibition of alpha-synuclein aggregation in vitro by m2E6. When monomeric alpha-synuclein is incubated shaking at 37 C for several days, there is an increase in thioflavin fluorescence indicating aggregation of alpha-synuclein into amyloid (control curve). Increasing amount of m2E6 mixed with monomeric alpha-synuclein shows a dose dependent inhibition in increase of the thioflavin fluorescence (example 5).

Example 5: In-Vitro Inhibition of Alpha-Synuclein Aggregation and Dissociation of Pre-Formed Alpha-Synuclein Fibrils Inhibition of Alpha-Synuclein Aggregation In Vitro Aggregation of alpha-synuclein into fibrillary assemblies, Lewy bodies and Lewy neurites (LNs), is a major hallmark of Parkinson's disease. Fibril formation is a complex polymerization process, characterized by a sigmoidal growth profile. The Thioflavin T (ThT) method was used to detect aggregation of alpha-synuclein in vitro (Giehm & Otzen, 2010, Anal Biochem. 15; 400(2):270-81; Giehm et al. 2011, Methods; 53(3):295-305). In this assay we tested the effect of m2E6 for reduction of alpha-synuclein aggregation when co-incubated with alpha-synuclein monomers at different ratios. Briefly, 96 well plates were loaded with the mixture of alpha-synuclein, ThT and antibody, sealed with Crystal Clear sealing tape (Hampton Research, Aliso Viejo, Calif., USA) to avoid evaporation. The plates were loaded into an Infinite 200 fluorescence plate reader (Tecan, Männedorf, Switzerland) or a Genios Pro (Tecan) and incubated at 37° C. Agitated samples were shaken with orbital or linear agitation (300 rpm) for a period of approximately 50 min/h. ThT fluorescence was measured with excitation at 450 nm and emission at 485 nm. For agitated samples, ThT emission was measured at 10 min intervals in a 96 well plate. The buffer signal was subtracted from all data. The results showed that m2E6 inhibited fibrillation of alpha-synuclein almost completely at higher molar ratio (antibody:alpha-synuclein) (FIG. 5).

Dissociation of Alpha-Synuclein Fibrils

Figure 6:
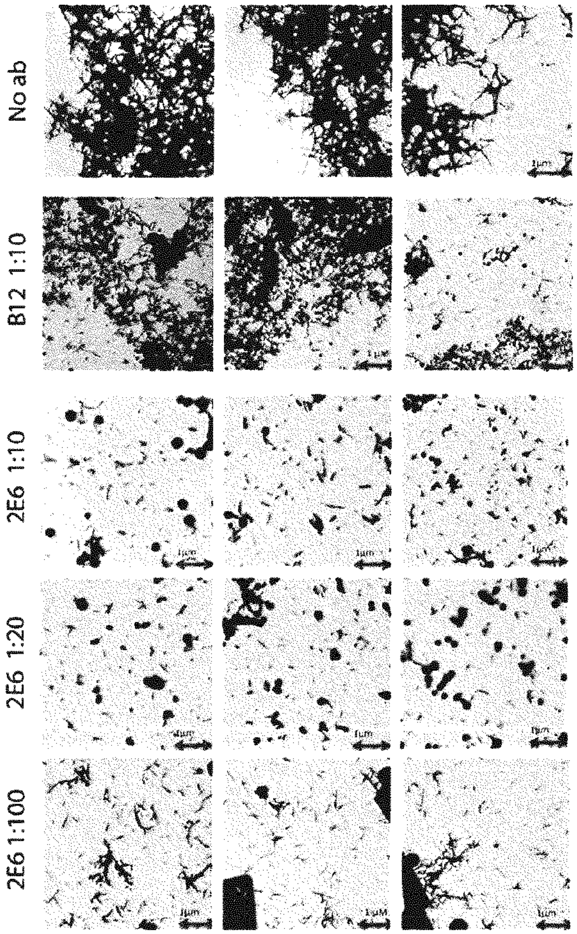
FIG. 6 shows dissociation of alpha-synuclein fibrils by m2E6. Preformed alpha-synuclein fibrils were sonicated to break them into smaller microfibrils. Antibody m2E6 was added at different molar ratios to the sonicated fibrils. Control fibrils without antibody (no ab) or fibrils incubated with a isotype control antibody not binding to alpha-synuclein (B12) show extensive fibrillary network visualized by electron microscopy. Fibrils incubated with different concentrations of m2E6 show a dose dependent decrease in larger fibrils.

The Mouse-alpha-synuclein preformed fibrils (Mo-PFFs) were generated from monomeric mouse alpha-synuclein using the Virginia Lee/Kelvin Luk protocol (Luk et al, Science, 2012, 16; 338(6109):949-53). These Mo-PFFs have been characterized for their physico-chemical properties (by Western Blot and Electron microscopy) and biological properties (by uptake and toxicity in cells). An important step in the preparation of the preformed fibrils (PFFs) is sonication shortly before injection or use in e.g. cells to dissociate larger aggregates of PFFs that cannot be taken up by the cells. In order to decide the optimal sonication protocol (intensity/strength and time) different sonication paradigms was tested. Sonicated preformed fibrils were incubated with antibody (ab) at different molar ratios room temperature for 24 hours. All samples were following stored on dry ice before analysis by negative staining and transmission Electron Microscopy. By incubation of α-synuclein PFFs with increasing concentrations of m2E6 in molar ratios of ab:Synuclein at 1:100, 1:20 and 1:10 the remaining microfibrils were small, linear and singular. All concentrations of ab tested were able to keep the microfibrils from re-associating into large networks of fibrils and possibly even dissociate them further. The results showed that increasing concentrations of m2E6 show increasing effects in keeping the fibrils as microfibrils. (FIG. 6)

Example 6: Cell Model Data

2E6 Binds Alpha-Synuclein Fibrils in Media and Inhibits their Accumulation in Human, Neuroblastoma and Melanoma, Cell Lines Description of Fibril Preparation Recombinant alpha-synuclein was ordered from rPeptide (catalog #S-1001-2) and dissolved according to the manufacturers recommendation in double-distilled water resulting in a 1 mg/ml solution in 20 mM Tris-HCL/100 mM NaCl, pH=7.4. The alpha-synuclein was fluorescently labelled with Atto488 by using the Atto488 Protein Labeling Kit from Sigma (#38371). A mixture of 30% Atto488-labelled and 70% unlabeled alpha-synuclein was made and this mixture was then incubated at 37° C. with agitation (300 rpm) for 2 days, then a pause for 3 days, then 1 day of agitation, then 1 day pause, then 4 days of agitation. After that the fibrils were harvested at kept at −20° C. until use. When fibrils were used in cellular assays, they were always sonicated at 5 min, setting 5.50% cycle, with horn probe sonicator, immediately prior to addition.

Immunoprecipitation of Alpha-Synuclein Fibrils in Media

The ability of the antibodies to bind and pull down alpha-synuclein fibrils dissolved in DMEM media (as used in cellular assays) was analyzed by immunoprecipitaion. 2 μg of antibody was immobilized on magnetic Dynabeads protein G followed by immunoprecipitation at 90 min at room temperature. The yield of the immunoprecipitation was visualized by Western blotting with detection ab anti-human alpha-synuclein, Ab1904. This showed that m2E6 was able to pull down alpha-synuclein fibrils from the media, whereas B12 (non-reactive human IgG) and 5G4 (anti-alpha-synuclein from Roboscreen) was not, FIG. 7A.

Antibody-Mediated Inhibition of Accumulation in SHSY-5Y Cells

SH-SY5Y (ATCC® CRL-2266™) was ordered from ATCC and cultured according with the ATCC-guidelines. The cells were plated on Collagen-coated plates at a density of 40.000 cells/well. After one day of attachment, the cells were treated with alpha-synuclein fibrils and antibodies (both at 10 μg/ml) added directly to the media. The cells were then left to incubate for 24 hours, after which they were washed and lysed. Western Blot was run on the cytoplasmic fraction with antibody 1904 from Abcam. This showed that 2E6-HLD1 reduced the amount of fibrils accumulated in the cells, whereas an antibody without affinity towards alpha-synuclein B12 did not, FIG. 7B.

Antibody-Mediated Inhibition of Accumulation in SK-Mel5 Cells

The human melanoma cell line SK-mel5 (ATCC, HTB-70) was grown in accordance with the ATCC-guidelines. Cells were plated at a density of 3000 cells per well in Falcon BD 96-well plates and left to adhere overnight. Atto488-labelled alpha-synuclein fibrils were added to the cells (0.01 mg/ml) together with m2E6 antibody (0.01 mg/ml) and alpha-synuclein peptides 113-125 or 126-140 (0.01 mg/ml). After 24 hours of incubation, the cells were washed twice in PBS and fixed by 4% paraformaldehyde. The cells were then stained with Hoechst and read in Cellomics ArrayScan. Nuclei were detected in one channel and defined the number of valid objects. Atto488-labelled fibrils were detected in another channel in a pre-defined ring-formed area surrounding the nucleus, thus representing the cytoplasm of the cells. The percent of the cells containing alpha-synuclein spots was quantified. The result shows that in cells not given fibrils, there was only a very low background of spot-containing cells (background was probably due to autofluorescence) FIG. 7C. In the cells given fibrils only, 75% of the cells had accumulated intracellular spots. In the cells co-incubated with fibrils and m2E6 antibody, there were only around 30% spot-positive cells. When the cells were co-incubated with fibrils, m2E6 and the 126-140 peptide, there were around 60% positive cells, thus the peptide significantly inhibited the effect of m2E6. Co-incubation of the 113-120 peptide with fibrils and 2E6 did not change the effect of m2E6. Incubation of fibrils together with either of the peptides 113-120 or 126-140 had no effect on the accumulation of fibrils in the cells. Thus, the m2E6 binds to the alpha-synuclein fibrils in solution and inhibits their accumulation in the cells. This effect is specific as it could be inhibited by the peptide 126-140, but not 113-120 (FIG. 7C).

Treatment with increasing doses of 2E6-HLD1-7A10 showed a dose-dependent reduction in the percentage of cells with spots. Cells treated with irrelevant control antibody (B12) showed no effect (FIG. 7D).

m2E6 Binds Mammalian Produced, Oligomerized Alpha-Synuclein in Media and Inhibits it Accumulation in Primary Cortical Neurons The ability of the antibodies to bind and pull down alpha-synuclein oligomers dissolved in DMEM media was analyzed by immunoprecipitaion. 2 μg of antibody was immobilized on magnetic Dynabeads protein G followed by immunoprecipitation 90 min at room temperature. The yield of the immunoprecipitation was visualized by Western blotting with detection antibody, anti-human alpha Synuclein Antibody Monoclonal (4B12) (MA1-90346, Pierce). This showed that all of the 2E6-variants pulled down the alpha-synuclein oligomers from the media (FIG. 8A). The comparator m9E4 and h9E4 did also pull down the oligomers, but the h9E4 seems to less efficient (much weaker band at 14 kDa). Another comparator alpha-synuclein antibody (12F4 from Biogen) gave only a weak band that was not much different from the control antibody B12 (FIG. 8A).

Mouse primary cortical neurons were prepared from E14 embryos by dissecting the cortical region and homogenizing these in a trypsin-solution. The cells were then washed and resuspended in DMEM-media, counted and plated at 60000 cells per well in 96-well plates pre-coated with Poly-lysine. After 4 hours, the media was changed to Neurobasal with B27 supplement. After 2 days of culturing, Cytoarabinoside was added to inhibit astrocyte growth. At DIV7, the cells were treated with Syn-BAP PFFs (DIV=days in vitro culture—asyn-BAP PFFs=alpha-synuclein biotin acceptor peptide tag preformed fibrils), 10 μg/ml together with antibodies at 25 μg/ml and incubation was performed for 24 hours. After that, the cells were washed and fixed by addition of 100 μl 8% paraformaldehyde directly to the 100 μl media in the wells. Detection of intracellular Syn-BAP PFF aggregates was done either by immunocytochemistry with 15G7-antibody (Enzo) and a secondary FITC-labelled anti-rat antibody on the cells after permeabilization and blocking with BSA (1%) or with Streptavidin-Atto488 (Sigma) added to permebilized cells (the Syn-BAP has a biotin-tag and can therefore be detected by the Streptavidin). Nuclei were detected by Hoechst-staining. Quantification of the staining was done by Cellomics ArrayScan. Nuclei were detected in one channel and defined the number of valid objects. Green spots were detected in another channel in a pre-defined ring-formed area surrounding the nucleus, thus representing the cytoplasm of the cells. The average number of spots per cell was calculated. An example of the cells is shown in FIG. 8B. There was some background staining with the Strepativin-Atto488-based detection of the Syn-BAP PFF aggregates (untreated cells showed to have on average one spot per cell), but there was still a significant difference to the cells treated with Syn-BAP PFFs alone (they had around 1.8 spots per cell), FIG. 8C. Co-incubation of the Syn-BAP PFFs with either non-reactive B12 or the 9E4 antibody did not change the accumulation of Syn-BAP PFFs in the cells, whereas treatment with m2E6 or 2E6-HLD1 reduced the level of accumulation to background level (FIG. 8C). In the other experiment cells treated with Syn-BAP PFFs alone showed around 4.5 spots per cell; again B12 or 9E4 did not change this significantly. Treatment with m2E6, 2E6-HLD2 or 2E6-HLD3 reduced the level of accumulation significantly (to around 3 spots per cell) (FIG. 8D).

Antibody-Mediated Inhibition of Transfer of Alpha-Synuclein Fibrils from Cell to Cell in a Human Melanoma Cell Line To investigate if our antibodies also have an effect on transfer of alpha-synuclein fibrils from cell to cell, we have developed an assay as follows: The human melanoma cell line SK-mel5 (ATCC, HTB-70) was grown in accordance with the ATCC-guidelines. Cells were plated at a density of 3000 cells per well in Falcon BD 96-well plates and left to adhere overnight. On one plate (named the 'Feeder plate'), cells were given sonicated Atto488-labelled alpha-synuclein fibrils at a final concentration of 0.01 mg/ml for 24 hours. The cells were then washed twice with fresh media and then antibodies were added to the cells in the media. After 24 hours of incubation, the media from the individual wells were then transferred directly onto a new plate of SK-mel5 cells (the 'Recipient plate'). The 'Feeder plate' was then fixed immediately by adding 4% paraformaldehyde, whereas the 'Recipient plate' was left another 24 hours before fixation (by addition of 8% paraformaldehyde directly into the media). Both plates were kept in the dark and stained with Hoechst and then read in Cellomics ArrayScan. Nuclei were detected in one channel and defined the number of valid objects. Atto488-labelled fibrils were detected in another channel in a pre-defined ring-formed area surrounding the nucleus, thus representing the cytoplasm of the cells. The percent of the cells containing alpha-synuclein aggregates (spots) in the ring-area defining the cells were quantified.

The idea is that the alpha-synuclein fibrils that are internalized by the cells on the 'feeder' plate to some degree is omitted again and thus transferred via the conditioned media to the cells on the 'recipient' plate. Thus, we can measure the effect of antibodies on the clearance process in the 'feeder' cells (an intracellular effect) and on the inhibition of transfer to the cells on the 'recipient' plate. We can show that a significant amount of alpha-synuclei fibrils are actually transferred from the cells on the 'feeder' plate to the cells on the 'recipient' plate (60% cells positive on 'feeder'—37% positive on the 'recipient').

It was shown that m2E6—compared to fibrils—significantly reduces the number of cells with alpha-synuclein spots in both the 'feeder' and the 'recipient' plate (FIG. 9). The comparator antibody 1H7 (WO2007021255) had no effect on either plate. A control antibody (B12) did likewise have no effect. The commercial antibody LB509 (Abcam) was able to reduce the intracellular levels of alpha-synuclein on the 'feeder' plate, but did not reduce the amount of transferred alpha-synuclein significantly. FIG. 9.

Antibody-Mediated Inhibition of Seeding of Alpha-Synuclein

In order to show the effect of antibody mediated inhibition of seeding of intracellular alpha synuclein, a HEK293 cell based seeding assay was setup. In this assay, on day 1, HEK293 cells are transfected with control (pcDNA) or alpha-synuclein (WT, with HA tag) cDNA expressing plasmid and plated into 6 well plates. On day 2, alpha-synuclein fibrils (seeds) are mixed with different concentrations of antibodies and transfected into cells using lipofectamine. On day 3, the cells are trypsinized, split and re-plated in 6 wells. On day 4, the cells are harvested and lysed in triton buffer. Cell lysates are ultracentrifuged and supernatant are saved as the Triton or soluble fraction. Pellets are resuspended in SDS buffer and ultracentrifuged and supernatant are labelled as SDS soluble or insoluble fraction. Both the fractions, soluble and insoluble fractions, are run on SDS gel and total alpha-synuclein and phosphorylated alpha synuclein (S129P) are detected by 4B12/1904 antibody (total human synuclein) and S129P-asyn antibody (abcam 51253), respectively. The ratio of phosphorylated alpha synuclein/beta actin in the SDS soluble fraction is used to calculate levels of insoluble aggregated alpha-synuclein that is formed in response to addition of seeds plus minus 2E6-HLD1.

Transfection with alpha-synuclein plasmid followed by transfection of alpha-synuclein fibrils promotes aggregation and phosphorylation of alpha synuclein which is indicated by the presence of higher molecular weight alpha synuclein aggregates in the insoluble fraction on the western blot. Due to the presence of HA tag, transfected alpha synuclein runs higher and is differentiated from the endogenous alpha synuclein or the transfected fibrils that run at around 17 kD.

Mixing humanized version of m2E6, 2E6-HLD1, with the alpha synuclein fibrils decreases alpha synuclein aggregation and phosphorylation as compared to isotype control antibody B12. (FIG. 10A). There is a dose dependent inhibition with HLD1 in alpha synuclein phosphorylation (FIG. 10B).

Example 7: Acute In Vivo Data in F28-Snca Transgenic Mice

Acute Electrophysiological Effects of α-Synuclein Antibodies In Vivo

High expression levels of human α-synuclein are present in the hippocampus of F28-snca transgenic mice. In vivo electrophysiological assessment of synaptic transmission and plasticity in the CA1 area of the hippocampus in 4 to 6 months old male F28 snca transgenic and age-matched control mice showed that i) basal synaptic transmission is significantly impaired in F28 snca transgenic compared to age-matched control mice, and ii) paired-pulse facilitation is significantly enhanced in F28 snca transgenic compared to age-matched control mice (FIG. 11).

All experiments were carried out in accordance with the European Communities Council Directive (86/609/EEC) for the care and use of laboratory animals and the Danish legislation regulating animal experiments.

F28-snca transgenic and age-matched control male mice (Taconic Europe A/S) aged 4 to 6 months were used in the present studies. Mice were single-housed in controlled temperature (22±1.5° C.) and humidity conditions (55-65%) and kept in a 12:12 hour light/dark cycle (lights on at 06:00 h). Food and water were available ad libitum.

Animals were anesthetized with an intraperitoneal (i.p.) injection of urethane (1.2 g/kg). Mice were then mounted in a stereotaxic frame, their temperature adjusted to 37.5° C. via a heating pad, and the skull was exposed. A platinum wire was placed in the frontal bone to act as a reference, and an additional hole was drilled for insertion of the recording and stimulating electrodes in the hippocampus, at the following coordinates according to the atlas of Paxinos and Franklin (Paxinos and Franklin, 2001): recording, 1.5-1.7 mm posterior to Bregma, 1.0-1.2 mm lateral to the midline, 1.4-1.7 mm below the surface of the brain; stimulation, 1.8-2.0 mm posterior to Bregma, 1.5-1.7 mm lateral to the midline, 1.5-1.7 mm below the surface of the brain. Animals were left in the stereotaxic frame through the whole duration of the recordings and their level of anesthesia was regularly checked.

Field potentials (fEPSP) were evoked in the CA1 by electrical stimulation of the Schaffer collateral every 30 second (s), and the depth of the recording electrode was adjusted until a negative fEPSP was recorded in response to a unipolar square pulse. The slope of the evoked fEPSP was measured between 30 and 70% of the maximum amplitude of the fEPSP.

Once an optimal fEPSP was induced, basal synaptic transmission was assessed by the relationship between stimulation intensity and slope of the evoked fEPSP (input-output relationship). The different intensities of stimulation were 0, 25, 50, 75, 100, 150, 200, 300, 400, and 500 μA, and were applied successively in increasing order, with 2 to 3 repeats for each intensity. Basal synaptic transmission was found to be significantly impaired in F28 snca transgenic compared to age-matched control mice (see FIG. 11*a*).

Paired-pulse facilitation, a short-term synaptic plasticity believed to rely on presynaptic mechanisms, was further measured in F28 snca transgenic and age-matched control mice. Briefly, a pair of stimuli with an interstimulus interval (ISI) varying from 25 to 1000 ms was applied to the Schaffer collateral, and the slope of the second fEPSP was compared to the slope of the first fEPSP. Facilitation was observed at all ISIs, with a maximum facilitation at ISIs of 50 and 75 ms. Interestingly, a significantly stronger PPF was observed in F28 snca transgenic mice at ISIs of 25, 50 and 75 ms when compared to age-matched control mice (FIG. 11*b*). Since Schaffer collaterals characteristically show facilitation due to residual $Ca^{2+}$ in the terminal, it has been suggested that manipulations that inhibit glutamate release may lead to an increased PPF. Therefore, our findings in F28 transgenic mice suggest that the impaired basal synaptic transmission is likely due to impaired vesicular release as a result of α-synuclein overexpression.

The identified impairments in basal synaptic transmission and paired-pulse facilitation in F28 snca transgenic mice were further used as readout to test alpha-synuclein antibody efficacies. Recordings were performed in all experiments 3 to 6 h following administration of a single dose of antibody (i.p.). Basal synaptic transmission and paired-pulse facilitation were recorded in both hippocampi in each animal when possible, and further used as individual experiments.

Acute treatment with h9E4 (15 mg/kg i.p.) induced a significant reversal of the impairment in basal synaptic transmission in F28-snca transgenic mice (Tg-snca+h9E4 vs. Tg-snca+PBS, p=0.002, FIG. 12). However, the reversal by h9E4 was only partial, as indicated by a significantly lower basal synaptic transmission compared to littermates treated with PBS (p=0.007).

A significant increase in PPF was confirmed in Tg-snca treated with PBS compared to littermates treated with PBS (p=0.044, FIG. 13). Treatment with h9E4 did not have any significant effect on the PPF compared to PBS treated transgenic mice (FIG. 13).

Basal synaptic transmission in F28-snca transgenic mice treated with a control mouse IgG (5C9) was significantly lower than in age-matched mice treated with the control mouse IgG (5C9) (p<0.001, FIG. 10). Acute treatment with m2E6 at a dose of 15 mg/kg induced a significant reversal of the impairment in basal synaptic transmission in F28-snca transgenic mice (Tg-snca+m2E6 vs. Tg-snca+control IgG, p=0.004, FIG. 14). Basal synaptic transmission in m2E6-treated transgenic mice was not significantly different from basal synaptic transmission in control mIgG-treated age-matched mice, indicating a full reversal of the impairment. Treatment with m2E6 had no effect on basal synaptic transmission in non-transgenic age-matched mice.

A significant impairment in PPF was confirmed in control mouse IgG-treated F28-snca transgenic mice compared to control mouse IgG-treated age-matched mice (p=0.023). Treatment with m2E6 did not have any significant effect on the PPF impairment in F28-snca transgenic mice when compared to control mouse IgG-treated transgenic mice (FIG. 15).

Since 15 mg/kg m2E6 induced full reversal of the impairment in basal synaptic transmission in F28-snca transgenic mice, lower doses were tested in order to establish a dose-response relationship. The impairment in basal synaptic transmission in F28-snca transgenic mice was significantly reversed by m2E6 at a dose of 5 mg/kg i.p. to a level not significantly different to age-matched control mice (FIG. 16). By contrast, m2E6 at a dose of 2.5 mg/kg i.p. did not significantly reverse the impairment in basal synaptic transmission, although a strong trend was observed at high stimulation intensities (p=0.066, 0.010 and 0.050 at 300, 400 and 500 μA, respectively) (FIG. 17).

The chimeric 2E6, ch2E6 antibody was tested at a dose of 2.5 mg/kg i.p., and partially reversed the impairment in basal synaptic transmission in F28-snca transgenic mice when compared to PBS treatment (p=0.042, FIG. 18). This effect was not significantly different from the reversal obtained with m2E6 at the dose of 2.5 mg/kg in the present series of experiments (not shown). As observed with m2E6, chimeric 2E6 did not have any significant effect on the impaired PPF in F28-snca transgenic mice (FIG. 19).

The affinity matured, humanized version of 2E6, the antibody 2E6-HDL1, was significantly more efficient than the chimeric 2E6 to reverse the impairment in basal synaptic transmission in F28-snca transgenic mice, and induced a full reversal to a level not significantly different from PBS-treated littermates (FIG. 18). No significant reversal of the impaired PPF in F28-snca transgenic mice was observed with 2E6-HLD1 (FIG. 19).

Example 8: Microdialysis to Assess Human Alpha-Synuclein in the Brain of Awake, Freely Moving Animals Push-pull microdialysis was used to assess brain interstitial fluid (ISF) human α-synuclein from awake and freely moving F28 snca transgenic mice. Mice were single-housed in controlled temperature (22±1.5° C.) and humidity conditions (55-65%) and kept in a 12:12 hour light/dark cycle (lights on at 06:00 h). Food and water were available ad libitum. To enable microdialysis in the hippocampus, mice were anaesthetized with isoflurane and an intracerebral guide cannula was stereotaxically implanted into the brain, positioning the microdialysis probe in the hippocampus (co-ordinates of probe tip: 3.1 mm posterior and 2.8 mm lateral from bregma, and 1.3 mm relative dura mater) according to the atlas of Paxinos and Franklin 2001. Anchor screws and acrylic cement were used for the fixation of the guide cannulas. After implantation of the cannula mice were allowed to recover from the surgery for 2-3 days before dialysis. A probe was connected to a microdialysis peristaltic pump with two channels (MAB20; Microbiotech), which was operated in a push-pull mode. The inlet tubing of the microdialysis probe was connected to a peristaltic pump perfusing the probe with artificial CSF. The peristaltic pump was also connected to the outlet tubing in order to prevent perfusion fluid loss from the probe, by pulling the fluid through the tubing. The actual flow rate of the pump was determined without having the probe connected. The sample tubes were weighed before and after sampling for a given time period and the flow rate was calculated. Slightly different methods were used to investigate the effect of mouse 2E6 and human 9E4 on extracellular human α-synuclein levels.

a. Mouse 2E6: Performed in the hippocampus of F28 snca transgenic mice (app 30 weeks old). In the day of the experiment, a 2-mm, 3000 kDa cut-off brainlink probe was inserted through the guide cannula. As a perfusion buffer, 25% bovine serum albumin (Sigma) was diluted to 2% with artificial CSF (aCSF; in mM: 147 NaCl, 2.7 KCl, 1.2 $CaCl_2$, 0.85 $MgCl_2$) on the day of use and filtered through a 0.1-μm membrane. The pump was to have a constant flow of 0.5 μL/min. A 60-min sampling regimen was used throughout the experiment period. To avoid tissue damage, the experimental window was set from 14 to 48 h after probe implantation. 14-16 h after the start of the experiments, 2 baseline samples were collected and then mouse 2E6 or control isotype 5C9 were injected i.p at 15 mg/kg, and further 6 samples (6 h of collection) were collected. The dialysates were stored at −80° C. until human alpha-synuclein determination by ELISA (Covance ELISA kit). The average of the two basal values (2 h) prior to antibody treatment was taken as baseline and set to 100% for each animal. Differences were analyzed using two-way analysis of variance (ANOVA) with repeated measures. The basal levels of human alpha-synuclein in hippocampus were 11.9±2.4 ng/ml (mean±SEM, n=11, not corrected for the in vitro dialysis probe recovery). In control-5C9-antibody-treated animals, the level of human alpha-synuclein in hippocampus did not significantly change over time (FIG. 20). The administration of m2E6 (15 mg/kg, i.p.) caused a significant reduction in human alpha-synuclein in hippocampus (FIG. 20).

b. Human 9E4: Performed in the hippocampus of F28 snca transgenic mice (app 50 weeks old). In the day of the experiment, a 2-mm, 1000 kDa cut-off CMA probe was inserted through the guide cannula. As a perfusion buffer, 25% bovine albumin fraction V (Sigma) was diluted to 0.2% with artificial CSF (aCSF; in mM: 147 NaCl, 2.7 KCl, 1.2 $CaCl_2$), 0.85 MgCl2) on the day of use and filtered through a 0.1-μm membrane. The pump was set to have a constant flow of 1 μL/min. A 120-min sampling regimen was used throughout the experiment period. To avoid tissue damage, the experimental window was set from 14 to 48 h after probe implantation. 14-16 h after the start of the experiments, 2-3 baseline samples were collected and then human 9E4 or control isotype anti-hel were injected i.p at 15 mg/kg, and further 6 samples (12 h of collection) were collected. The dialysates were stored at −80° C. until human α-synuclein determination by ELISA (Covance ELISA kit). The average of the two-three basal values (4 h-6 h) prior to antibody treatment was taken as baseline and set to 100% for each animal. No differences were observed between the effect of human 9E4 or control isotype anti-hel on extracellular human α-synuclein levels (FIG. 21). Differences were analyzed using two-way analysis of variance (ANOVA) with repeated measures. The basal levels of human α-synuclein in hippocampus were 7.8±1.2 ng/ml (mean±SEM, n=16, not corrected for the in vitro dialysis probe recovery).

Example 9

Chronic Effects of α-Synuclein Antibodies In Vivo m2E6 Effects in a Rat Model of Human α-Synuclein Overexpression Targeted to Dopaminergic Neurons and in a Transgenic Mouse Model of Human α-Synuclein Overexpression.

Targeted overexpression of human α-synuclein to dopaminergic neurons in the rat midbrain can be achieved using a recombinant adeno-associated viral vector (rAAV) and is associated with a progressive loss of dopaminergic cells in the substantia nigra and motor impairments. In this rat AAV-based model of α-synuclein overexpression, basal ganglia neuronal firing activity was shown to be altered in a similar way to what has been described in Parkinson's disease patients, namely an increased firing irregularity in both the subthalamic nucleus and substantia *nigra reticulata*.

All experiments were carried out in accordance with the European Communities Council Directive (86/609/EEC) for the care and use of laboratory animals and the Danish legislation regulating animal experiments.

Adult female Sprague-Dawley rats (225-250 g) were used. Antibody treatment was initiated 2 to 4 days prior to viral injections, and continued until the end of the study. PBS administration at the same volume (5 ml/kg) was used as a control. Antibodies were dosed intraperitonally twice per week at a dose of 15 mg/kg (FIG. 22). The viral (rAAV2/5) containing human wt α-syn or GFP were injected unilaterally in the substantia nigra (SN). Animals were anaesthetized with a combination of Hypnorm® and Dormicum® at 2.0 ml/kg s.c. and placed in a stereotaxic frame. Their temperature was adjusted at 37.5° C. via a heating pad, and their skull was exposed. A hole was drilled above the right SN at the following coordinates, according to the atlas of Paxinos and Watson (Paxinos & Watson, 1998): 5.5 mm posterior and 2.0 mm lateral from Bregma. A single injection of 3 μL of rAAV2/5-α-syn or rAAV2/5-GFP was performed at a depth of 7.2 mm below the dura matter, and a flow rate of 0.2 μL/min using a Hamilton syringe connected to a stereotaxic injector. The needle was left in place an additional 5 min to allow diffusion of the vector in the SN. Following surgery the animals were returned to their home cage, and placed in a heated environment where they were allowed to recover from anesthesia.

Eight to 10 weeks following AAV injections, extracellular single unit recordings were performed in the subthalamic nucleus (STN) under urethane anesthesia. All recordings were done 2 to 4 days following the last antibody injection. A glass electrode was lowered into the STN (3.8±0.2 mm posterior and +2.4±0.2 mm lateral to Bregma) using a motorized micromanipulator. Extracellular action potentials were amplified, discriminated and monitored on an oscilloscope and an audiomonitor. Neurons were recorded and analyzed using Spike 2 software. In the STN, presumed glutamatergic neurons were found between 7.0-7.6 mm below the cortical surface. They typically exhibited a firing rate ranging between 0.5 and 40 spikes/s, and a narrow action potential. At least 200 consecutive spikes were used for analysis. The average firing rate and coefficient of variation of the interspike interval (CV ISI), defined as the ratio between the standard deviation of the ISI and the average ISI×100, were calculated for each neuron. Spike density histograms and autocorrelograms were constructed for each neuron and used to qualitatively classify the firing pattern into regular, irregular or bursty, as described previously (Kaneoke & Vitek, 1996; Tepper et al., 1995).

AAV-α-synuclein rats displayed an altered firing pattern of STN neurons compared to AAV-GFP rats, as indicated by a significant increase in the coefficient of variation of the interspike interval (CV ISI) (FIG. 23) and the significant change in the proportion of cells firing in a regular, irregular and bursty pattern (FIG. 24). Interestingly, treatment with m2E6 induced a significant normalisation of the proportion of neurons exhibiting the 3 distinct firing patterns (FIG. 24), as well as a non-significant trend for a decrease in their CV ISI (FIG. 23).

m2E6 Effects after Chronic Treatment in a Transgenic Mouse Model of Human α-Synuclein Overexpression.

The identified impairments in paired-pulse facilitation in F28 snca transgenic mice were further used as readout to test antibody efficacy after chronic treatment.

Animals were dosed twice weekly with either m2E6 or a control mIgG1 at a dose of 15 mg/kg i.p. for 16-18 weeks. All recordings were performed similarly as before in Example 7, but now the recordings were made 2 to 4 days following administration of the last dose of antibody instead of 3-6 hours, as was done for the acute experiment. Paired-pulse facilitation were recorded in both hippocampi in each animal when possible, and further used as individual experiments.

Paired-pulse facilitation was not significantly different in 2E6-treated age-matched control mice compared to 5C9-treated mice. As reported previously, enhancement of PPF was observed in F28 snca Tg mice treated with 5C9 compared to age-matched control mice treated with 5C9. Interestingly, treatment with 2E6 at a dose of 15 mg/kg i.p. normalized PPF in F28 snca Tg mice (FIG. 25).

Paired-pulse facilitation (PPF), is a short-term synaptic plasticity believed to rely on presynaptic mechanisms, Since Schaffer collaterals characteristically show facilitation due to residual $Ca^{2+}$ in the terminal, it has been suggested that manipulations that inhibit glutamate release may lead to an increased PPF. Therefore, our findings in F28 transgenic mice suggest that the impaired basal synaptic transmission is likely due to impaired vesicular release as a result of α-synuclein overexpression. Since only chronic treatment with antibody 2E6 is able to reverse the deficit in PPF, it suggests that long term antibody treatment can reduce the effect of alpha-synuclein overexpression on impaired vesicular release. This effect may translate to improved synaptic transmission in human PD patients treated with antibody therapy.

The invention claimed is:

1. A monoclonal antibody, or antigen-binding fragment thereof, capable of specifically binding to an epitope within amino acids 126-140 on alpha-synuclein (SEQ ID NO: 2), said monoclonal antibody or antigen-binding fragment thereof comprising: a light chain variable region comprising the CDRs of:

(i) light chain CDR1 comprising the amino acid sequence of SEQ ID NO: 3;

(ii) light chain CDR2 comprising the amino acid sequence of SEQ ID NO: 4; and (iii) light chain CDR3 comprising the amino acid sequence of SEQ ID NO: 5; and a heavy chain variable region comprising the CDRs of:

(i) heavy chain CDR1 comprising the amino acid sequence of SEQ ID NO: 6;

(ii) heavy chain CDR2 comprising the amino acid sequence of SEQ ID NO: 7; and (iii) heavy chain CDR3 comprising the amino acid sequence of SEQ ID NO: 8.

2. The monoclonal antibody or antigen-binding fragment thereof according to claim 1 wherein the antibody comprises or consists of an intact antibody.

3. The monoclonal antibody, or antigen-binding fragment thereof, according to claim 1 comprising or consisting of an antigen-binding fragment selected from the group consisting of Fv fragments Fab-like fragments and domain antibodies.

4. The monoclonal antibody, or antigen-binding fragment thereof, according to claim 1 wherein the monoclonal antibody is selected from the group consisting of antibodies of subtype IgG1, IgG2, IgG3 and IgG4.

5. The monoclonal antibody or antigen-binding fragment thereof according to claim 1 that is humanized.

6. The monoclonal antibody or antigen-binding fragment thereof according to claim 1 comprising:

(i) a light chain variable region comprising or consisting of the amino acid sequence of SEQ ID NO:19; and (ii) a heavy a chain variable region comprising or consisting of the amino acid sequence of SEQ ID NO:20.

7. The monoclonal antibody, or antigen-binding fragment thereof, according to claim 1 comprising:

(i) a light chain variable region comprising or consisting of the amino acid sequence of SEQ ID NO:21; and (ii) a heavy a chain variable region comprising or consisting of the amino acid sequence of SEQ ID NO:22.

8. The monoclonal antibody or antigen-binding fragment thereof according to claim 1 comprising:

(i) a light chain variable region comprising or consisting of the amino acid sequence of SEQ ID NO:23; and (ii) a heavy a chain variable region comprising or consisting of the amino acid sequence of SEQ ID NO:24.

9. The monoclonal antibody or antigen-binding fragment thereof according to claim 1 comprising:

(i) a light chain variable region comprising or consisting of the amino acid sequence of SEQ ID NO:25; and (ii) a heavy a chain variable region comprising or consisting of the amino acid sequence of SEQ ID NO:26.

* * * * *

UNITED STATES PATENT AND TRADEMARK OFFICE

CERTIFICATE OF CORRECTION

PATENT NO. : 11,325,968 B2
APPLICATION NO. : 16/469482
DATED : May 10, 2022
INVENTOR(S) : Pekka Kallunki et al.

It is certified that error appears in the above-identified patent and that said Letters Patent is hereby corrected as shown below:

In the Claims

In Claim 3, at Column 97, Line 67:
The text "of Fv fragments Fab-like fragments and domain antibodies." should be replaced with -- of Fv fragments, Fab-like fragments and domain antibodies. --

Signed and Sealed this
Twentieth Day of September, 2022

Katherine Kelly Vidal

Katherine Kelly Vidal
*Director of the United States Patent and Trademark Office*

SEQUENCE LISTING

```
<160> NUMBER OF SEQ ID NOS: 48

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15
```

-continued

```
Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140


<210> SEQ ID NO 2
<211> LENGTH: 15
<212> TYPE: PRT
<213> ORGANISM: artificial
<220> FEATURE:
<223> OTHER INFORMATION: Epitope 126-140

<400> SEQUENCE: 2

Glu Met Pro Ser Glu Glu Gly Tyr Gln Asp Tyr Glu Pro Glu Ala
1               5                   10                  15


<210> SEQ ID NO 3
<211> LENGTH: 10
<212> TYPE: PRT
<213> ORGANISM: artificial
<220> FEATURE:
<223> OTHER INFORMATION: CDR1 VL

<400> SEQUENCE: 3

Ser Ala Ser Ser Ser Val Ser Tyr Met His
1               5                   10


<210> SEQ ID NO 4
<211> LENGTH: 7
<212> TYPE: PRT
<213> ORGANISM: artificial
<220> FEATURE:
<223> OTHER INFORMATION: CDR2 VL

<400> SEQUENCE: 4

Asp Thr Ser Lys Leu Ala Ser
1               5


<210> SEQ ID NO 5
<211> LENGTH: 9
<212> TYPE: PRT
<213> ORGANISM: artificial
<220> FEATURE:
<223> OTHER INFORMATION: CDR3 VL

<400> SEQUENCE: 5

Gln Gln Trp Ser Ser Asn Pro Pro Thr
1               5


<210> SEQ ID NO 6
```

-continued

<211> LENGTH: 5
<212> TYPE: PRT
<213> ORGANISM: artificial
<220> FEATURE:
<223> OTHER INFORMATION: CDR1 VH

<400> SEQUENCE: 6

Ser Tyr Trp Met His
1 5

<210> SEQ ID NO 7
<211> LENGTH: 17
<212> TYPE: PRT
<213> ORGANISM: artificial
<220> FEATURE:
<223> OTHER INFORMATION: CDR2 VH

<400> SEQUENCE: 7

Arg Ile Asp Pro Asn Ser Gly Thr Thr Lys Tyr Asn Val Asn Phe Lys
1 5 10 15

Thr

<210> SEQ ID NO 8
<211> LENGTH: 12
<212> TYPE: PRT
<213> ORGANISM: artificial
<220> FEATURE:
<223> OTHER INFORMATION: CDR3 VH

<400> SEQUENCE: 8

Leu Gly His Tyr Gly Asn Leu Tyr Ala Met Asp Tyr
1 5 10

<210> SEQ ID NO 9
<211> LENGTH: 10
<212> TYPE: PRT
<213> ORGANISM: artificial
<220> FEATURE:
<223> OTHER INFORMATION: CDR1 VL 7C4

<400> SEQUENCE: 9

Ser Ala Ser Ser Ser Val Ser Phe Met His
1 5 10

<210> SEQ ID NO 10
<211> LENGTH: 10
<212> TYPE: PRT
<213> ORGANISM: artificial
<220> FEATURE:
<223> OTHER INFORMATION: CDR1 VL 7A10/8D9

<400> SEQUENCE: 10

Ser Ala Ser Ser Ser Val Ser Tyr Ile His
1 5 10

<210> SEQ ID NO 11
<211> LENGTH: 9
<212> TYPE: PRT
<213> ORGANISM: artificial
<220> FEATURE:
<223> OTHER INFORMATION: CDR3 VL L3

<400> SEQUENCE: 11

Gln Gln Trp Thr Ser Asn Pro Pro Phe
1 5

-continued

<210> SEQ ID NO 12
<211> LENGTH: 5
<212> TYPE: PRT
<213> ORGANISM: artificial
<220> FEATURE:
<223> OTHER INFORMATION: CDR1 VH 7C4

<400> SEQUENCE: 12

Arg Tyr Trp Met His
1 5

<210> SEQ ID NO 13
<211> LENGTH: 17
<212> TYPE: PRT
<213> ORGANISM: artificial
<220> FEATURE:
<223> OTHER INFORMATION: CDR2 VH 5A1

<400> SEQUENCE: 13

Arg Val Asp Pro Asn Ser Gly Thr Thr Lys Tyr Asn Val Asn Phe Lys
1 5 10 15

Thr

<210> SEQ ID NO 14
<211> LENGTH: 17
<212> TYPE: PRT
<213> ORGANISM: artificial
<220> FEATURE:
<223> OTHER INFORMATION: CDR2 VH 9G11

<400> SEQUENCE: 14

Arg Ile Asp Pro Asn Ser Gly Thr Thr Lys Tyr Asn Val His Phe Lys
1 5 10 15

Thr

<210> SEQ ID NO 15
<211> LENGTH: 17
<212> TYPE: PRT
<213> ORGANISM: artificial
<220> FEATURE:
<223> OTHER INFORMATION: CDR2 VH 9C12

<400> SEQUENCE: 15

Arg Ile Asp Pro Asn Ser Gly Thr Thr Lys Tyr Asn Val Asn Ile Lys
1 5 10 15

Thr

<210> SEQ ID NO 16
<211> LENGTH: 12
<212> TYPE: PRT
<213> ORGANISM: artificial
<220> FEATURE:
<223> OTHER INFORMATION: CDR3 VH 5A1

<400> SEQUENCE: 16

Leu Gly His Tyr Gly Asn Leu Asn Ala Met Asp Tyr
1 5 10

<210> SEQ ID NO 17
<211> LENGTH: 12
<212> TYPE: PRT
<213> ORGANISM: Artificial
<220> FEATURE:
<223> OTHER INFORMATION: CDR3 VH 9D7

<400> SEQUENCE: 17

```
Leu Gly His Tyr Ser Lys Val Leu Ala Met Asp Tyr
1               5                   10


<210> SEQ ID NO 18
<211> LENGTH: 12
<212> TYPE: PRT
<213> ORGANISM: artificial
<220> FEATURE:
<223> OTHER INFORMATION: CDR3 VH 7A10/8D9

<400> SEQUENCE: 18

Leu Gly His Tyr Gly Asn Leu Tyr Ala Lys Asp Tyr
1               5                   10


<210> SEQ ID NO 19
<211> LENGTH: 106
<212> TYPE: PRT
<213> ORGANISM: artificial
<220> FEATURE:
<223> OTHER INFORMATION: m2E6 VL

<400> SEQUENCE: 19

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Thr Arg Phe Ser Gly Ser
    50                  55                  60

Gly Ser Gly Thr Ser Tyr Ser Leu Thr Ile Ser Ser Met Asp Thr Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105


<210> SEQ ID NO 20
<211> LENGTH: 118
<212> TYPE: PRT
<213> ORGANISM: artificial
<220> FEATURE:
<223> OTHER INFORMATION: m2E6 VH

<400> SEQUENCE: 20

Gln Val Gln Leu Gln Gln Pro Gly Ala Glu Leu Val Lys Pro Gly Ala
1               5                   10                  15

Ser Val Lys Leu Ser Cys Thr Ala Ser Gly Tyr Thr Phe Thr Ser Tyr
            20                  25                  30

Trp Met His Trp Met Lys Gln Arg Pro Gly Arg Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Lys Ala Thr Leu Thr Val Asp Lys Pro Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Leu Gly His Tyr Gly Asn Leu Tyr Ala Met Asp Tyr Trp Gly
            100                 105                 110
```

-continued

Gln Gly Thr Ser Val Thr
        115

<210> SEQ ID NO 21
<211> LENGTH: 106
<212> TYPE: PRT
<213> ORGANISM: artificial
<220> FEATURE:
<223> OTHER INFORMATION: ch2E6 VL

<400> SEQUENCE: 21

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Thr Arg Phe Ser Gly Ser
    50                  55                  60

Gly Ser Gly Thr Ser Tyr Ser Leu Thr Ile Ser Ser Met Asp Thr Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105

<210> SEQ ID NO 22
<211> LENGTH: 118
<212> TYPE: PRT
<213> ORGANISM: artificial
<220> FEATURE:
<223> OTHER INFORMATION: ch2E6 VH

<400> SEQUENCE: 22

Gln Val Gln Leu Gln Gln Pro Gly Ala Glu Leu Val Lys Pro Gly Ala
1               5                   10                  15

Ser Val Lys Leu Ser Cys Thr Ala Ser Gly Tyr Thr Phe Thr Ser Tyr
            20                  25                  30

Trp Met His Trp Met Lys Gln Arg Pro Gly Arg Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Lys Ala Thr Leu Thr Val Asp Lys Pro Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Leu Gly His Tyr Gly Asn Leu Tyr Ala Met Asp Tyr Trp Gly
            100                 105                 110

Gln Gly Thr Ser Val Thr
        115

<210> SEQ ID NO 23
<211> LENGTH: 107
<212> TYPE: PRT
<213> ORGANISM: artificial
<220> FEATURE:
<223> OTHER INFORMATION: 2E6-HLD1 VL

<400> SEQUENCE: 23

Glu Ile Val Leu Thr Gln Ser Pro Ala Thr Leu Ser Leu Ser Pro Gly

-continued

```
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys Arg
            100                 105


<210> SEQ ID NO 24
<211> LENGTH: 118
<212> TYPE: PRT
<213> ORGANISM: artificial
<220> FEATURE:
<223> OTHER INFORMATION: 2E6-HLD1 VH

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Met Asp Tyr Trp Gly
            100                 105                 110

Gln Gly Thr Leu Val Thr
        115


<210> SEQ ID NO 25
<211> LENGTH: 107
<212> TYPE: PRT
<213> ORGANISM: artificial
<220> FEATURE:
<223> OTHER INFORMATION: 2E6-HLD2 VL

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80
```

```
Asp Phe Ala Val Tyr Tyr Cys Gln Gln Trp Ser Ser Asn Pro Pro Thr
                85                  90                  95

Phe Gly Gln Gly Thr Lys Leu Glu Ile Lys Arg
            100                 105


<210> SEQ ID NO 26
<211> LENGTH: 118
<212> TYPE: PRT
<213> ORGANISM: Artificial
<220> FEATURE:
<223> OTHER INFORMATION: 2E6-HLD2 VH

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Met Asp Tyr Trp Gly
            100                 105                 110

Gln Gly Thr Leu Val Thr
        115


<210> SEQ ID NO 27
<211> LENGTH: 107
<212> TYPE: PRT
<213> ORGANISM: artificial
<220> FEATURE:
<223> OTHER INFORMATION: 2E6-HLD 3 VL

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Thr Ser Asn Pro Pro Asn
                85                  90                  95

Phe Gly Gln Gly Thr Lys Leu Glu Ile Lys Arg
            100                 105


<210> SEQ ID NO 28
<211> LENGTH: 118
<212> TYPE: PRT
<213> ORGANISM: artificial
<220> FEATURE:
<223> OTHER INFORMATION: 2E6-HLD 3  VH
```

<400> SEQUENCE: 28

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Met Arg Gln Ala Pro Gly Gln Gly Leu Glu Trp Ile
35 40 45

Gly Arg Ile Asp Pro Asn Ser Gly Thr Thr Lys Tyr Asn Val Asn Phe
50 55 60

Lys Thr Arg Val Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Gly His Tyr Gly Asn Leu Tyr Ala Met Asp Tyr Trp Gly
100 105 110

Gln Gly Thr Leu Val Thr
115

<210> SEQ ID NO 29
<211> LENGTH: 106
<212> TYPE: PRT
<213> ORGANISM: artificial
<220> FEATURE:
<223> OTHER INFORMATION: 5A1 VL

<400> SEQUENCE: 29

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Tyr Met
20 25 30

His Trp Tyr Gln Gln Lys Pro Gly Gln Ala Pro Arg Arg Trp Ile Tyr
35 40 45

Asp Thr Ser Lys Leu Ala Ser Gly Val Pro Ala Arg Phe Ser Gly Ser
50 55 60

Gly Ser Gly Thr Asp Tyr Thr Leu Thr Ile Ser Arg Leu Glu Pro Glu
65 70 75 80

Asp Phe Ala Val Tyr Tyr Cys Gln Gln Trp Ser Ser Asn Pro Pro Thr
85 90 95

Phe Gly Gln Gly Thr Lys Leu Glu Ile Lys
100 105

<210> SEQ ID NO 30
<211> LENGTH: 118
<212> TYPE: PRT
<213> ORGANISM: artificial
<220> FEATURE:
<223> OTHER INFORMATION: 5A1 VH

<400> SEQUENCE: 30

Gln Val Gln Leu Val Gln Ser Gly Ala Glu Val Lys Lys Gln Gly Ala
1 5 10 15

Ser Val Lys Val Ser Cys Lys Ala Ser Gly Tyr Thr Phe Thr Ser Tyr
20 25 30

Trp Met His Tyr Met Arg Gln Ala Pro Gly Gln Gly Leu Glu Trp Ile
35 40 45

Gly Arg Val Asp Pro Asn Ser Gly Thr Thr Lys Tyr Asn Val Asn Phe
50 55 60

-continued

```
Lys Thr Arg Ala Thr Leu Thr Val Asp Lys Thr Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Asn Ala Met Asp Tyr Trp Gly
            100                 105                 110

Gln Gly Thr Leu Val Thr
        115


<210> SEQ ID NO 31
<211> LENGTH: 106
<212> TYPE: PRT
<213> ORGANISM: artificial
<220> FEATURE:
<223> OTHER INFORMATION: 9D7 VL

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105


<210> SEQ ID NO 32
<211> LENGTH: 118
<212> TYPE: PRT
<213> ORGANISM: artificial
<220> FEATURE:
<223> OTHER INFORMATION: 9D7 VH

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Ser Lys Val Leu Ala Met Asp Tyr Trp Gly
            100                 105                 110

Gln Gly Thr Leu Val Thr
        115


<210> SEQ ID NO 33
```

<211> LENGTH: 106
<212> TYPE: PRT
<213> ORGANISM: artificial
<220> FEATURE:
<223> OTHER INFORMATION: 9G11 VL

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Gln Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 34
<211> LENGTH: 118
<212> TYPE: PRT
<213> ORGANISM: artificial
<220> FEATURE:
<223> OTHER INFORMATION: 9G11 VH

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val His Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Thr Asp Tyr Trp Gly
            100                 105                 110

Gln Gly Thr Leu Val Thr
        115

<210> SEQ ID NO 35
<211> LENGTH: 106
<212> TYPE: PRT
<213> ORGANISM: artificial
<220> FEATURE:
<223> OTHER INFORMATION: 7C4 VL

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Phe Met
            20                  25                  30

His Trp Tyr Gln Gln Lys Pro Gly Gln Ala Pro Arg Arg Trp Ile Tyr
35 40 45

Asp Thr Ser Lys Leu Ala Ser Gly Val Pro Ala Arg Phe Ser Gly Ser
50 55 60

Gly Ser Gly Thr Asp Tyr Thr Leu Thr Ile Ser Ser Leu Glu Pro Glu
65 70 75 80

Asp Phe Ala Val Tyr Tyr Cys Gln Gln Trp Ser Ser Asn Pro Pro Thr
85 90 95

Phe Gly Gln Gly Thr Lys Leu Glu Ile Lys
100 105

<210> SEQ ID NO 36
<211> LENGTH: 118
<212> TYPE: PRT
<213> ORGANISM: artificial
<220> FEATURE:
<223> OTHER INFORMATION: 7C4 VH

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Arg Tyr
20 25 30

Trp Met His Trp Met Arg Gln Ala Pro Gly Gln Gly Pro Glu Trp Ile
35 40 45

Gly Arg Ile Asp Pro Asn Ser Gly Thr Thr Lys Tyr Asn Val Asn Phe
50 55 60

Lys Thr Arg Ala Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Gly His Tyr Gly Asn Leu Tyr Ala Met Asp Tyr Trp Gly
100 105 110

Gln Gly Thr Leu Val Thr
115

<210> SEQ ID NO 37
<211> LENGTH: 106
<212> TYPE: PRT
<213> ORGANISM: artificial
<220> FEATURE:
<223> OTHER INFORMATION: L3 VL

<400> SEQUENCE: 37

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Tyr Met
20 25 30

His Trp Tyr Gln Gln Lys Pro Gly Gln Ala Pro Arg Arg Trp Ile Tyr
35 40 45

Asp Thr Ser Lys Leu Ala Ser Gly Val Pro Ala Arg Phe Ser Gly Ser
50 55 60

Gly Ser Gly Thr Asp Tyr Thr Leu Thr Ile Ser Ser Leu Glu Pro Glu
65 70 75 80

Asp Phe Ala Val Tyr Tyr Cys Gln Gln Trp Ser Ser Asn Pro Pro Thr
85 90 95

Phe Gly Gln Gly Thr Lys Leu Glu Ile Lys
100 105

<210> SEQ ID NO 38
<211> LENGTH: 118
<212> TYPE: PRT
<213> ORGANISM: artificial
<220> FEATURE:
<223> OTHER INFORMATION: L3 VH

<400> SEQUENCE: 38

```
Gln Val Gln Leu Val Gln Gln Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Met Asp Tyr Trp Gly
            100                 105                 110

Gln Gly Thr Leu Val Thr
        115
```

<210> SEQ ID NO 39
<211> LENGTH: 106
<212> TYPE: PRT
<213> ORGANISM: artificial
<220> FEATURE:
<223> OTHER INFORMATION: 7A10 VL

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Ile
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Thr Ser Asn Pro Pro Asn
                85                  90                  95

Phe Gly Gln Gly Thr Lys Leu Glu Ile Lys
            100                 105
```

<210> SEQ ID NO 40
<211> LENGTH: 118
<212> TYPE: PRT
<213> ORGANISM: artificial
<220> FEATURE:
<223> OTHER INFORMATION: 7A10 VH

<400> SEQUENCE: 40

```
Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Lys Asp Tyr Trp Gly
            100                 105                 110

Gln Gly Thr Leu Val Thr
        115

<210> SEQ ID NO 41
<211> LENGTH: 106
<212> TYPE: PRT
<213> ORGANISM: artificial
<220> FEATURE:
<223> OTHER INFORMATION: 8D9 VL

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Ile
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105

<210> SEQ ID NO 42
<211> LENGTH: 118
<212> TYPE: PRT
<213> ORGANISM: artificial
<220> FEATURE:
<223> OTHER INFORMATION: 8D9 VH

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Phe
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Leu Gly His Tyr Gly Asn Leu Tyr Ala Lys Asp Tyr Trp Gly
            100                 105                 110

Gln Gly Thr Leu Val Thr
        115


<210> SEQ ID NO 43
<211> LENGTH: 106
<212> TYPE: PRT
<213> ORGANISM: artificial
<220> FEATURE:
<223> OTHER INFORMATION: 9C12 VL

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gln Gly Thr Lys Leu Glu Ile Lys
            100                 105


<210> SEQ ID NO 44
<211> LENGTH: 118
<212> TYPE: PRT
<213> ORGANISM: artificial
<220> FEATURE:
<223> OTHER INFORMATION: 9C12 VH

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Met Arg Gln Ala Pro Gly Gln Gly Leu Glu Trp Ile
        35                  40                  45

Gly Arg Ile Asp Pro Asn Ser Gly Thr Thr Lys Tyr Asn Val Asn Ile
    50                  55                  60

Lys Thr Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly His Tyr Gly Asn Leu Tyr Ala Met Asp Tyr Trp Gly
            100                 105                 110

Gln Gly Thr Leu Val Thr
        115


<210> SEQ ID NO 45
<211> LENGTH: 106
<212> TYPE: PRT
<213> ORGANISM: artificial
<220> FEATURE:
<223> OTHER INFORMATION: 6B6 VL
```

<400> SEQUENCE: 45

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Tyr Met
20 25 30

His Trp Tyr Gln Gln Lys Pro Gly Gln Ala Pro Arg Arg Leu Ile Tyr
35 40 45

Asp Thr Ser Lys Leu Ala Ser Gly Val Pro Ala Arg Phe Ser Gly Ser
50 55 60

Gly Ser Gly Thr Asp Tyr Thr Leu Thr Ile Ser Ser Leu Glu Pro Glu
65 70 75 80

Asp Phe Ala Val Tyr Tyr Cys Gln Gln Trp Ser Ser Asn Pro Pro Thr
85 90 95

Phe Gly Gln Gly Thr Lys Leu Glu Ile Lys
100 105

<210> SEQ ID NO 46
<211> LENGTH: 118
<212> TYPE: PRT
<213> ORGANISM: artificial
<220> FEATURE:
<223> OTHER INFORMATION: 6B6 VH

<400> SEQUENCE: 46

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met His Trp Met Arg Gln Ala Pro Gly Gln Gly Leu Glu Trp Ile
35 40 45

Gly Arg Ile Asp Pro Asn Ser Gly Thr Thr Lys Tyr Asn Val Asn Phe
50 55 60

Lys Thr Arg Ala Thr Leu Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Gly His Tyr Gly Asn Leu Tyr Ala Met Asp Tyr Trp Gly
100 105 110

Gln Gly Thr Leu Val Thr
115

<210> SEQ ID NO 47
<211> LENGTH: 446
<212> TYPE: PRT
<213> ORGANISM: Artificial
<220> FEATURE:
<223> OTHER INFORMATION: 9E4 LC

<400> SEQUENCE: 47

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Lys Gly Leu Glu Trp Val
35 40 45

Ala Ser Ile Ser Ser Gly Gly Gly Ser Thr Tyr Tyr Pro Asp Asn Val
50 55 60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 48
<211> LENGTH: 220
<212> TYPE: PRT
<213> ORGANISM: Artificial
<220> FEATURE:

-continued

```
<223> OTHER INFORMATION: 9E4 HC

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```